(12) United States Patent
Gomez et al.

(10) Patent No.: US 9,963,435 B2
(45) Date of Patent: May 8, 2018

(54) COMPOUNDS FOR THERAPEUTIC USE

(71) Applicant: Dart NeuroScience, LLC, San Diego, CA (US)

(72) Inventors: Laurent Gomez, San Diego, CA (US); Mark Eben Massari, Ramona, CA (US)

(73) Assignee: Dart NeuroScience, LLC, San Diego, CA (US)

( * ) Notice: Subject to any disclaimer, the term of this patent is extended or adjusted under 35 U.S.C. 154(b) by 0 days. days.

(21) Appl. No.: 15/253,645

(22) Filed: Aug. 31, 2016

(65) Prior Publication Data

US 2018/0057470 A1   Mar. 1, 2018

(51) Int. Cl.
C07D 265/16 (2006.01)
C07D 413/04 (2006.01)
C07D 413/06 (2006.01)
C07D 413/12 (2006.01)
C07F 11/00 (2006.01)

(52) U.S. Cl.
CPC ......... *C07D 265/16* (2013.01); *C07D 413/04* (2013.01); *C07D 413/06* (2013.01); *C07D 413/12* (2013.01); *C07F 11/00* (2013.01)

(58) Field of Classification Search
None
See application file for complete search history.

(56) References Cited

U.S. PATENT DOCUMENTS

| 8,785,500 B2 | 7/2014 | Charney et al. |
| 2009/0197297 A1 | 8/2009 | Murray et al. |
| 2014/0296241 A1 | 10/2014 | Wainer et al. |

FOREIGN PATENT DOCUMENTS

| EP | 0 623 343 A1 | 11/1994 |
| WO | WO 97/07750 A1 | 3/1997 |
| WO | WO 2004/045601 A1 | 6/2004 |
| WO | WO 2009/131794 A1 | 10/2009 |
| WO | WO 2013/056229 A1 | 4/2013 |

OTHER PUBLICATIONS

Adams, J. D. et al., Studies on the biotransformation of ketamine 1—Identification of metabolites produced in vitro from rat liver microsomal preparations, Biological Mass Spectrometry, Nov. 1, 1981, pp. 527-538, vol. 8, No. 11.
Desta, Zeruesenay et al., Stereoselective and regiospecific hydroxylation of ketamine and norketamine, Xenobiotica, Nov. 2012, pp. 1076-1087, vol. 42, No. 11.
Leung, Louis Y. et al., Comparative Pharmacology in the Rat of Ketamine and Its Two Principal Metabolites, Norketamine and (Z)-6-Hydroxynorketamine, Journal of Medicinal Chemistry, 1986, pp. 2396-2399, vol. 29, American Chemical Society.
Moaddel, et al., A parallel chiral-achiral liquid chromatography method for the determination of the stereoisomers of ketamine and ketamine metabolites in the plasma and urine of patients with complex regional pain syndrome, Talanta, Oct. 15, 2010, pp. 1892-1904, vol. 82, No. 5.
Shimoyama, M. et al., Oral ketamine is antinociceptive in the rat formalin test: Role of the metabolite, norketamine, Pain, May 1, 1999, pp. 85-93, vol. 81, No. 1-2, Elsevier Science Publishers, Amsterdam, NL.
Turfus, S. C. et al., Use of human microsomes and deuterated substrates: an alternative approach for the identification of novel metabolites of ketamine by mass spectrometry, Drug Metab Dispos., Aug. 2009, pp. 1769-1778, vol. 37, No. 8.
Woolf, Thomas et al., Synthesis of (Z)- and (E)-6-Hydroxyketamine, J. Org. Chem., 1984, pp. 3305-3310., vol. 49, No. 18, American Chemical Society.
Woolf, T. F. et al., Biotransformation of ketamine, (Z)-6-hydroxyketamine, and (E)-6-hydroxyketamine by rat, rabbit, and human liver microsomal preparations, Xenobiotica, Jul. 1987, pp. 839-847, vol. 17, No. 7.
Zanos, Panos et al., NMDAR inhibition—independent antidepressant actions of ketamine metabolites, Nature, 2016, pp. 1-18, vol. 000, Macmillan Publishers Limited.
Zhao, X. et al., Simultaneous population pharmacokinetic modelling of ketamine and three major metabolites in patients with treatment-resistant bipolar depression, Br J Clin Pharmacol, Aug. 2012, pp. 304-314, vol. 74, No. 2.
PCT, International Preliminary Report on Patentability and Written Opinion, for International Application No. PCT/US2012/060256, dated Apr. 15, 2014.
Morris P.J. et al., "Synthesis and N-Methyl-o-aspartate (NMDA) Receptor Activity of Ketamine Metabolites", Organic Lttrs. (Aug. 22, 2017) 19(17): 4572-4575.
International Search Report and Written Opinion dated Oct. 17, 2017 for Application No. PCT/US2017/049129, filed Aug. 29, 2017.

*Primary Examiner* — Kortney L. Klinkel
*Assistant Examiner* — William Y Lee
(74) *Attorney, Agent, or Firm* — Knobbe, Martens, Olson & Bear LLP

(57) ABSTRACT

Chemical entities of Formula (I):

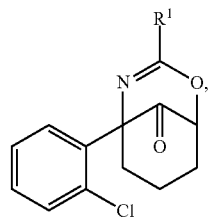

Formula (I)

Including enantiomers thereof, wherein $R^1$ has any of the values described herein, and compositions comprising such chemical entities; their preparation; and their use in various methods, including the treatment of depression, pain, cognitive disorders, neurodegenerative disorders, and other neurological and peripheral disorders.

10 Claims, No Drawings

COMPOUNDS FOR THERAPEUTIC USE

FIELD OF THE DISCLOSURE

This disclosure relates to chemical entities, including compounds, as described herein; compositions containing them; methods of making them; and their use in various methods, including the treatment of depression, pain, dementia, and other neurological and peripheral disorders.

BACKGROUND

Discovered more than 50 years ago, ketamine is an anesthetic that is thought to act primarily by antagonizing the glutamatergic NMDAR (N-methyl-D-aspartate receptor). It is typically administered intramuscularly or intravenously for starting and maintaining general anesthesia in humans and other animals, and has also been used for anti-anxiety, sedation, and analgesic purposes. See, e.g., Costi et al., *Curr. Behav. Neurosci. Rep.* 2015, 4. 216-225; Oddo et al., *Crit. Care* 2016, 20, 128-138. In addition, ketamine has shown potent efficacy in treating depression and pain when administered at sub-anesthetic doses; even single infusions of such doses appear to show rapid action in treating bipolar depression and treatment-resistant major depression. Iadarola et al., *Ther. Adv. Chronic Dis.* 2015, 6, 97-114; Zarate et al., *Arch. Gen. Psychiatry* 2006, 63, 856-864; Lally et al. *Transl. Psychiatry* 2014, 4, e469; Murrough et al., *Am. J. Psychiatry* 2013, 170, 1134-1142.

Clinical use of ketamine is limited, however, by its poor oral bioavailability, abuse liability, and undesirable psychological reactions, such as dissociative effects and hallucinations observed at even low doses. See, e.g., Strayer and Nelson, *Am. J. Emerg. Med.* 2008, 26, 985-1028; Morgan and Curran, *Addiction* 2010, 107, 27-38. In addition, ketamine action is complicated by multiple metabolites arising after its administration, many of which do not have anesthetic properties. See, e.g., Leung et al., *J. Med. Chem.* 1986, 29, 2396-2399.

Recent studies have shown that a ketamine metabolite, (2R,6R)-hydroxynorketamine, has antidepressant activity in mice. Zanos et al., *Nature* 2016, 533, 481-486. In addition, hydroxynorketamine (HNK) metabolites have been implicated in the analgesic efficacy of ketamine in treating pain. Moaddel et al., *Talanta* 2010, 15, 1892-1904. In contrast to ketamine, HNK is not known to inhibit NMDAR, but is thought to modulate a different glutamate receptor, the AMPA (α-amino-3-hydroxy-5-methyl-4-isoxazole propionic acid) receptor. Furthermore, the action of HNK does not appear to be associated with undesired effects that can result from ketamine therapy, such as abuse liability and anesthetic effects.

These observations highlight the need for alternative ketamine therapeutics useful in treating depression, pain, and other CNS disorders. The present disclosure meets these and other needs in the art by disclosing chemical entities, including compounds, which can act through HNK-mediated pathways.

SUMMARY

Disclosed are chemical entities of Formula (I):

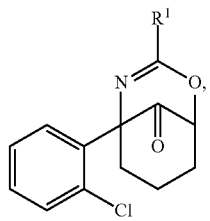

Formula (I)

including the various stereoisomers and enantiomers, wherein $R^1$ is as described herein. Also disclosed are compositions comprising the compounds of Formula (I); methods of making the compounds and compositions; and their use in a wide range of methods that include treating pain, depression, and other neurological disorders, as well as enhancing cognitive function.

DETAILED DESCRIPTION

The embodiments may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art.

ABBREVIATIONS

The specification includes numerous abbreviations, whose meanings are listed in the following Table:

| Abbreviation | Definition |
| --- | --- |
| AcCl | Acetyl Chloride |
| ACN | Acetonitrile |
| BSTFA | N,O-Bis(trimethylsilyl)trifluoroacetamide |
| CELITE ® | Diatomaceous earth |
| DBN | 1,5-Diazabicyclo[4.3.0]non-5-ene |
| DBU | 1,8-diazabicyclo[5.4.0]undec-7-ene |
| DCM | Dichloromethane |
| DIPEA, DIEA | N,N-ethyl-diisopropylamine or N,N-Diisopropyl-ethyl amine |
| DMA | N,N-Dimethylacetamide |
| DMF | N,N-Dimethylformamide |
| DMSO | Dimethylsulfoxide |
| EtOAc, or EA | Ethyl acetate |
| EtOH | Ethanol |
| Et$_2$O | Diethyl ether |
| HATU | 1-[Bis(dimethylamino)methylene]-1H-1,2,3-triazolo[4,5-b] |
| HBr | Hydrobromic acid |
| HCl | Hydrochloric acid |
| HPLC | High-performance liquid chromatography |

-continued

| Abbreviation | Definition |
|---|---|
| LCMS, LC/MS | Liquid chromatography-mass spectrometry |
| LiHMDS, LHMDS | Lithium bis(trimethylsilyl)amide |
| LDA | Lithium diisopropylamide |
| mCPBA | meta-Chloroperoxybenzoic acid |
| MeOH | Methanol |
| TMSCl or Me$_3$SiCl | Trimethylsilyl chloride |
| TMSI or Me$_3$SiI | Trimethylsilyl iodide |
| MgSO$_4$ | Magnesium sulfate |
| Na$_2$CO$_3$ | Sodium carbonate |
| NaHCO$_3$ | Sodium bicarbonate |
| NaOH | Sodium hydroxide |
| Na$_2$SO$_3$ | Sodium sulfite |
| Na$_2$SO$_4$ | Sodium sulfate |
| NIS | N-Iodosuccinimide |
| i-PrOH | Isopropanol |
| i-Pr$_2$O | Diisopropyl ether |
| SiO$_2$ | Silica |
| TEA, Et$_3$N | Triethylamine |
| TFA | Trifluoroacetic acid |
| THF | Tetrahydrofuran |

Terms and Definitions

The use of headings and subheadings provided in the sections of this specification is solely for convenience of reference and does not limit the various embodiments herein, which are to be construed by reference to the specification as a whole.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. Thus, the term "example" is used to provide exemplary instances of the item in discussion, not an exhaustive or limiting list thereof. Similarly, adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances should not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "substituted," as used herein, means that at least one hydrogen on the designated atom or group is replaced with a selection from the indicated group, provided that the designated atom's normal valence is not exceeded. When a substituent is keto (i.e., =O), then 2 hydrogen atoms on the atom are replaced.

A dash ("-") that is not between two letters or symbols is used to indicate a point of covalent attachment for a substituent. For example, —(CH$_2$)C$_3$-C$_7$cycloalkyl is attached through carbon of the methylene (CH$_2$) group.

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "—"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, halo, hydroxyl, alkoxy, thioalkoxy, amino, and aminoalkyl.

The term "alkenyl" refers to optionally substituted unsaturated aliphatic moieties having at least one carbon-carbon double bond and including E and Z isomers of said alkenyl moiety. Examples of alkenyl radicals include ethenyl, propenyl, butenyl, 1,4-butadienyl, cyclopentenyl, cyclohexenyl and the like.

The term "alkynyl" refers to optionally substituted unsaturated aliphatic moieties having at least one carbon-carbon triple bond and includes straight and branched chain alkynyl groups. Examples of alkynyl radicals include ethynyl, propynyl, butynyl and the like.

The term "haloalkyl" refers to a straight- or branched-chain alkyl group having from 1 to 12 carbon atoms in the chain, substituting one or more hydrogens with halogens.

Examples of haloalkyl groups include, but are not limited to, —CF$_3$, —CHF$_2$, —CH$_2$CF$_3$, —CH$_2$CHF$_2$, —CH$_2$CH$_2$F, —CH$_2$CH$_2$Cl, —CH$_2$CF$_2$CF$_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl," "thioalkyl," and "sulfonylalkyl" are analogous to alkoxy, replacing the terminal oxygen atom of alkoxy with, respectively, NH (or NR), S (sulfur), and SO$_2$.

The term "haloalkoxy" refer to alkoxy groups substituting one or more hydrogens with halogens. Examples of haloalkoxy groups include, but are not limited to, —OCF3, —OCH2CF3, —OCH2CHF2, —OCH2CH2Cl, —OCH2CF2CF3, —OCH(CH3)CHF2 and other groups that in light of the ordinary skill in the art and the teachings provided herein, would be considered equivalent to any one of the foregoing examples.

The term "amino" refers to the —NH2 group.

The term "heteroatom" used herein refers to, for example, O (oxygen), S (sulfur), N (nitrogen), and Selenium (Se).

The term "aryl" refers to a monocyclic, or fused or spiro polycyclic, aromatic carbocycle (ring structure having ring atoms that are all carbon), having from 3 to 12 ring atoms per ring (carbon atoms in aryl groups are sp2 hybridized). Illustrative examples of aryl groups include the following moieties:

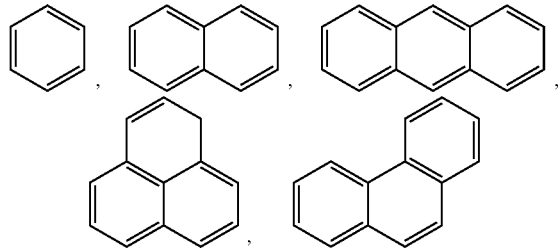

and the like.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

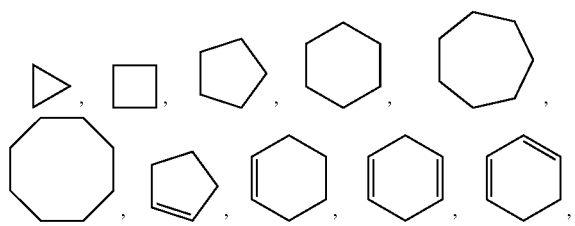

-continued

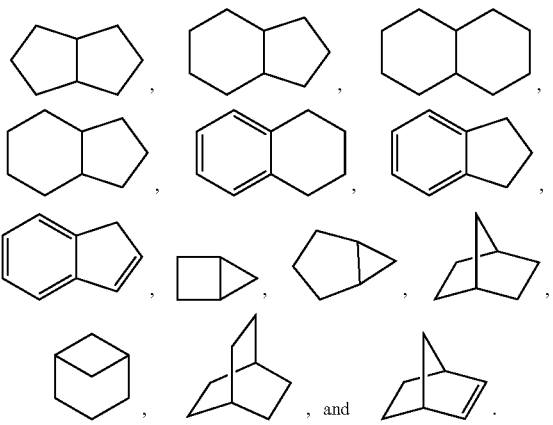

, and

"Heterocycloalkyl" means a saturated cyclic group containing from 1 to about 3 heteroatoms chosen from N, O, S, and Se with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized. A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, selenium, and sulfur. The ring structure may optionally contain up to two oxo groups on carbon or sulfur ring members. Illustrative (but not limiting) entities, in the form of properly bonded moieties, include:

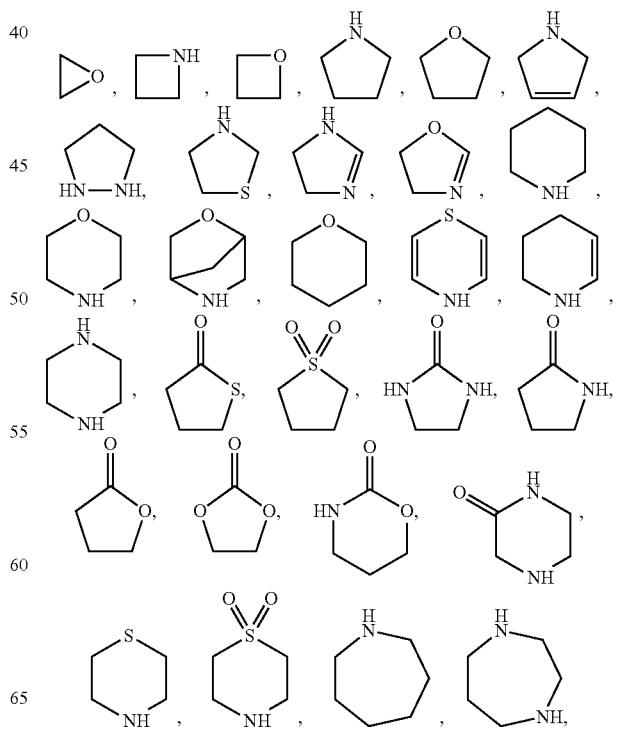

-continued

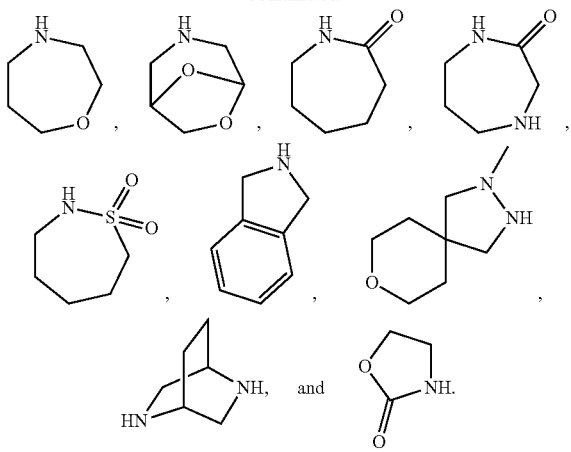

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

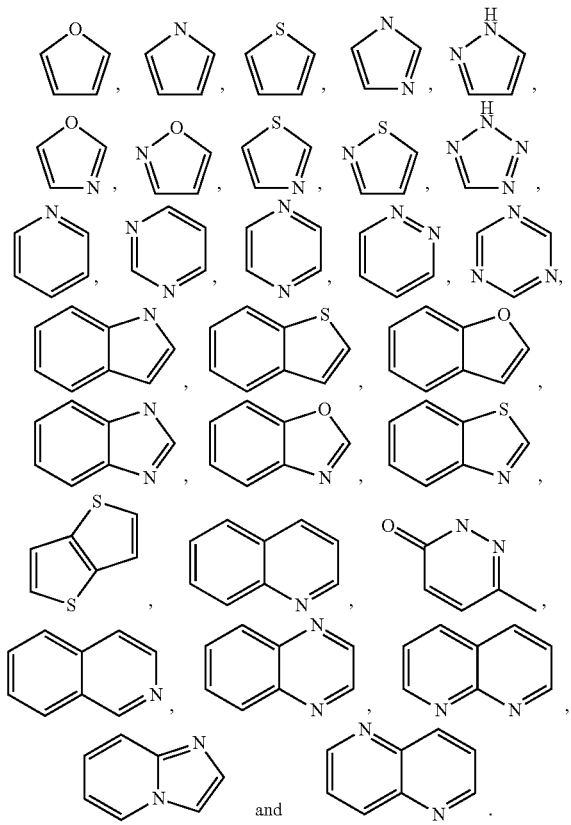

Those skilled in the art will recognize that the species of cycloalkyl, aryl, heterocycloalkyl, and heteroaryl groups listed or illustrated above are not exhaustive, and that additional species within the scope of these defined terms may also be selected.

The term "halogen" represents chlorine, fluorine, bromine or iodine; and the term "halo" represents chloro, fluoro, bromo or iodo.

The terms "optional" and "optionally" refer to the subsequently described event or circumstance and mean that it may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

Formulas

Certain compounds are described herein using a general formula that includes variables, e.g. $R^1$-$R^{12}$.

Any formula disclosed herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. The symbols are used as meaning the same spatial arrangement in chemical structures shown herein. Analogously, the symbols are used as meaning the same spatial arrangement in chemical structures shown herein.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Chemical Entities

As used herein, the term "chemical entity" collectively refers to a compound, along with its salts, chelates, solvates, conformers, non-covalent complexes, metabolites, and pro-drugs.

Compounds disclosed herein are described using standard nomenclature. Unless defined otherwise, all technical and scientific terms used herein have the same meaning as is commonly understood by one of skill in the art to which this disclosure belongs.

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the un-dissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion+ $H_3NCH_2COO-$. Zwitterions, zwitterionic compounds, inner salts, and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine, such as $^2H$ (deuterium), $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

When referring to any formula given herein, the selection of a particular moiety from a list of possible species for a specified variable is not intended to define the same choice of the species for the variable appearing elsewhere. That is, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$ and "$S^2_{example}$ is one of $S_3$ and $S_4$ is accordingly used herein for the sake of brevity but not by way of limitation.

The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $R^6$, $R^7$, $R^8$, $R^9$, $R^{10}$, $R^{12}$, and $R^{13}$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $R^6$, $R^7$, $R^8$, $R^9$, $R^{10}$, $R^{11}$, $R^{12}$, and $R^{13}$, and any other generic substituent symbol used herein.

The nomenclature "$C_{i\text{-}j}$" with $j>i$, when applied herein to a class of substituents, is meant to refer to embodiments of this invention for which each and every one of the number of carbon members, from i to j including i and j, is independently realized. By way of example, the term $C_{1\text{-}3}$ refers independently to embodiments that have one carbon member ($C_1$), embodiments that have two carbon members ($C_2$), and embodiments that have three carbon members ($C_3$).

The term $C_{n\text{-}m}$alkyl refers to an aliphatic chain, whether straight or branched, with the total number N of carbon members in the chain that satisfies $n \leq N \leq m$, with $m > n$.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "therapeutically effective amount" or "effective amount" means an amount effective, when administered to a human or non-human patient, to provide any therapeutic benefit. A therapeutic benefit may be an amelioration of symptoms, e.g., an amount effective to decrease the symptoms of a depressive disorder, cognitive disorder, or pain. A therapeutically effective amount of a compound is also an amount sufficient to provide a significant positive effect on any indicia of a disease, disorder, or condition e.g. an amount sufficient to significantly reduce the frequency and severity of depressive symptoms or pain. A significant effect on an indicia of a disorder or condition includes a statistically significant in a standard parametric test of statistical significance such as Student's T-test, where $p<0.05$; though the effect need not be significant in some embodiments.

A "pharmaceutical compositions" is a composition comprising at least one active agent, such as a compound, or pharmaceutically acceptable salt thereof, of Formula (I), and at least one other substance, such as a carrier, excipient, or diluent.

The term "carrier" applies to pharmaceutical compositions of the disclosure and refers to a diluent, adjuvant, excipient, or vehicle with which an active compound is administered.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., *J. Med. Chem.* 2007, 50, 6665-6672; Berge et al., *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition". For example, a neurological disorder also means a neurological disease or a neurological condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). In some embodiments, an "effective amount" also means an amount or dose of a compound or composition effective to modulate an HNK-associated signaling pathway, such as a glutamatergic pathway. The "effective amount" will vary, depending on the compound, the disease, the type of treatment desired, and its severity, and age, weight, of the subject, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human. Medical treatment can include treatment of an existing condition, such as a disease or disorder, prophylactic or preventative treatment, or diagnostic treatment. In some embodiments the patient is a human patient.

As used herein, a "control animal" or a "normal animal" is an animal that is of the same species as, and otherwise comparable to (e.g., similar age, sex), the animal that is trained under conditions sufficient to induce transcription-dependent memory formation in that animal.

A "patient" means any human or non-human animal in need of medical treatment. Medical treatment can include treatment of an existing condition, such as a disease or disorder, prophylactic or preventative treatment, or diagnostic treatment. In some embodiments the patient is a human patient.

"Administering" means introducing into the body of a subject a chemical entity, such as a compound or pharmaceutically acceptable salt thereof, or a composition containing such a chemical entity, for use via any appropriate route, for example, oral administration in either solid or liquid dosage form.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to (or "compared to") the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the terms "training protocol," or "training," refer to either "cognitive training" or "motor training."

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds and Chemical Entities

The disclosure relates to compounds and chemical entities of Formula (I), and their use in the disclosed methods.

In some embodiments, the disclosure provides a chemical entity of Formula (I):

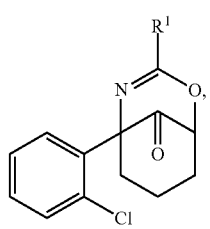

Formula (I)

wherein:
R¹ is —H; or
R¹ is —C$_{1-6}$alkyl, optionally substituted with one or more members, each independently selected from the group consisting of: -halo, -hydroxy, -alkoxy, -amino and -carboxyl; or
R¹ is —C$_{3-8}$alkenyl or —C$_{3-8}$alkynyl, each optionally substituted with one or more members, each independently selected from the group consisting of: -halo, -hydroxy, —C$_{1-4}$ alkyl, —C$_{1-4}$alkoxy, and amino; or
R¹ is —(CH$_2$)$_n$aryl, —(CH$_2$)$_n$heteroaryl, —(CH$_2$)$_n$cycloalkyl, or —(CH$_2$)$_n$heterocycloalkyl, each optionally substituted with one or more members, each independently selected from the group consisting of: -halo, -hydroxy, —C$_{1-4}$ alkyl, —C$_{1-4}$alkoxy, and -amino, wherein n is independently an integer selected from 0, 1, 2, 3, and 4; or
R¹ is —COR², —CONR³R⁴, —CR⁵R⁶NR⁷R⁸, —CHR⁹R¹⁰, or —C(OH)R¹¹R¹²,
wherein R², R³, R⁴, R⁷ and R⁸ are each independently selected from the group consisting of: —H, —C$_{1-8}$alkyl, and —C$_{1-8}$haloalkyl;
R⁵ and R⁶ are each independently selected from the group consisting of: —H, -halo, —NH$_2$, —C$_{1-8}$alkyl, —C$_{1-8}$haloalkyl, —(CH$_2$)$_n$CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, —(CH$_2$)$_n$CONR$^{14}$R$^{1B}$, —(CH$_2$)$_n$ NHC(=O)R$^{1A}$, —(CH$_2$)$_n$NR$^{14}$R$^{1B}$, —(CH$_2$)$_n$OR$^{1C}$, —(CH$_2$)$_n$SR$^{1C}$ and —(CH$_2$)$_n$SeR$^{1C}$, wherein n is independently an integer selected from 0, 1, 2, 3, and 4;
each R$^{1A}$ is independently selected from the group consisting of: —H—C$_{1-8}$alkyl, —C$_{1-8}$haloalkyl, —(CH$_2$)$_n$CONH$_2$, —(CH$_2$)$_n$COOH, —(CH$_2$)$_n$aryl, —(CH$_2$)$_n$heteroaryl, —(CH$_2$)$_n$cycloalkyl, and —(CH$_2$)$_n$heterocycloalkyl, said —(CH$_2$)$_n$aryl, —(CH$_2$)$_n$heteroaryl, —(CH$_2$)$_n$cycloalkyl, and —(CH$_2$)$_n$heterocycloalkyl each optionally substituted with one or more members, each independently selected from the group consisting of: -halo, -hydroxy, —C$_{1-4}$ alkyl, —C$_{1-4}$alkoxy, and -amino, wherein n is independently an integer selected from 0, 1, 2, 3, and 4;
each R$^{1B}$ is independently selected from the group consisting of: —H—C$_{1-8}$alkyl, —C$_{1-8}$haloalkyl, —(CH$_2$)$_n$CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, wherein n is independently an integer selected from 0, 1, 2, 3, and 4;
each R$^{1C}$ is independently selected from the group consisting of: —H—C$_{1-8}$alkyl, —C$_{1-8}$haloalkyl, —(CH$_2$)$_n$CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, wherein n is independently an integer selected from 0, 1, 2, 3, and 4;
R⁹ and R¹⁰ are each independently selected from the group consisting of: —H, —C$_{1-8}$alkyl, and —C$_{1-8}$haloalkyl, said alkyl optionally substituted with up to 3 members, each independently selected from the group consisting of: -amino, -hydroxy and -carboxyl; or optionally R⁹ and R¹⁰ taken together with the carbon to which they are attached can form an optionally substituted five membered heteroaryl or heterocycloalkyl ring; and
R¹¹ and R¹² are each independently selected from the group consisting of: —H, —C$_{1-6}$alkyl, and —C$_{1-6}$haloalkyl, said —C$_{1-6}$alkyl, and —C$_{1-6}$haloalkyl optionally substituted with up to 3 members, each independently selected from the group consisting of: -hydroxy and amino.

In some embodiments, a chemical entity corresponds to the (1R,5R) enantiomer of Formula (I):

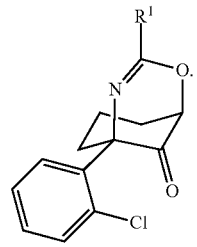

In some embodiments, a chemical entity corresponds to the (1S,5S) enantiomer of Formula (I):

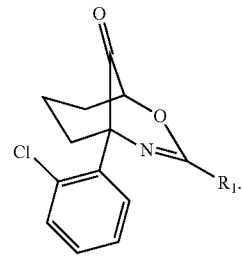

In some embodiments, 1e is —H; or
R¹ is —C$_{1-6}$alkyl, optionally substituted with one or more members, each independently selected from the group consisting of: -halo, -hydroxy, -alkoxy, -amino and -carboxyl; or
R¹ is —C$_{3-8}$alkenyl or —C$_{3-8}$alkynyl, each optionally substituted with one or more members, each independently selected from the group consisting of: -halo, -hydroxy, —C$_{1-4}$ alkyl, —C$_{1-4}$alkoxy, and amino; or
R¹ is —(CH$_2$)$_n$aryl, —(CH$_2$)$_n$heteroaryl, —(CH$_2$)$_n$cycloalkyl, or —(CH$_2$)$_n$heterocycloalkyl, each optionally substituted with one or more members, each independently selected from the group consisting of: -halo, -hydroxy, —C$_{1-4}$ alkyl, —C$_{1-4}$alkoxy, and -amino, wherein n is independently an integer selected from 0, 1, 2, 3, and 4; or
R¹ is —CR⁵R⁶NR⁷R⁸, —CHR⁹R¹⁰, or —C(OH)R¹¹R¹²,
wherein R⁷ and R⁸ are independently selected from the group consisting of: —H, —C$_{1-8}$alkyl, and —C$_{1-8}$haloalkyl;
R⁵ and R⁶ are each independently selected from the group consisting of: —H, -halo, —NH$_2$, —C$_{1-8}$alkyl, —C$_{1-8}$haloalkyl, —(CH$_2$)$_n$ CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, wherein n is independently an integer selected from 0, 1, 2, 3, and 4;
R⁹ and R¹⁰ are each independently selected from the group consisting of: —H, —C$_{1-8}$alkyl, and —C$_{1-8}$haloalkyl, said alkyl optionally substituted with up to 3 members, each independently selected from the group consisting of -amino, -hydroxy, and -carboxyl; or optionally R⁹ and R¹⁰ taken together with the carbon to which they are attached can form an optionally substituted five membered heteroaryl or heterocycloalkyl ring; and
R¹¹ and R¹² are independently selected from the group consisting of: —H, —C$_{1-6}$alkyl, and —C$_{1-6}$haloalkyl, said —C$_{1-6}$alkyl, and —C$_{1-6}$haloalkyl optionally substituted with up to 3 members, each independently selected from the group consisting of: -hydroxy and -amino.

In some embodiments, $R^1$ is —H; or

—$C_{1-6}$alkyl, optionally substituted with one or more members, each independently selected from the group consisting of: -halo, -hydroxy, -alkoxy, -amino and -carboxyl; or —$C_{3-8}$alkenyl or —$C_{3-8}$alkynyl, each optionally substituted with one or more members, each independently selected from the group consisting of: -halo, -hydroxy, —$C_{1-4}$ alkyl, —$C_{1-4}$alkoxy, and amino; or —$(CH_2)_n$aryl, —$(CH_2)_n$heteroaryl, —$(CH_2)_n$cycloalkyl, or —$(CH_2)_n$heterocycloalkyl, each optionally substituted with one or more members, each independently selected from the group consisting of: -halo, -hydroxy, —$C_{1-4}$ alkyl, —$C_{1-4}$alkoxy, and -amino, wherein n is independently an integer selected from 0, 1, 2, 3, and 4; or —$COR^2$, —$CONR^3R^4$, —$CR^5R^6NR^7R^8$, —$CHR^9R^{10}$, and —$C(OH)R^{11}R^{12}$, wherein $R^2$, $R^3$, $R^4$, $R^7$ and $R^8$ are independently selected from the group consisting of: —H, —$C_{1-8}$alkyl, and —$C_{1-8}$haloalkyl;

$R^5$ and $R^6$ are independently selected from the group consisting of: —H, -halo, —$NH_2$, —$C_{1-8}$alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, wherein n is independently an integer selected from 0, 1, 2, 3, and 4;

$R^9$ and $R^{10}$ are independently selected from the group consisting of: —H, —$C_{1-8}$alkyl, and —$C_{1-8}$haloalkyl, said alkyl optionally substituted with up to 3 members, each independently selected from the group consisting of: -amino, -hydroxy and -carboxyl; or optionally $R^9$ and $R^{10}$ taken together with the carbon to which they are attached can form a five membered heteroaryl or heterocycloalkyl ring; and $R^{11}$ and $R^{12}$ are independently selected from the group consisting of: —H, —$C_{1-6}$alkyl, and —$C_{1-6}$haloalkyl, optionally substituted with up to 3 members, each independently selected from the group consisting of: -hydroxy and amino.

In some embodiments, $R^1$ is —$CR^5R^6NR^7R^8$ or —$CR^9R^{10}$, wherein $R^5$ and $R^6$ are independently selected from the group consisting of: —H, —F, —Cl, —Br, —$NH_2$, -methyl, -ethyl, -n-propyl, -isopropyl, -butyl, -pentyl, —$NH_2$, —$C_{1-8}$haloalkyl, —$(CH_2)_n$ $CONH_2$, —$(CH_2)_n$ COOH, —$(CH_2)_n$ aryl, —$(CH_2)_n$benzyl, —$(CH_2)_n$heteroaryl, —$(CH_2)$indole, —$(CH_2)$imidazole, —$(CH_2)_n$cycloalkyl, —$(CH_2)_n$heterocycloalkyl, —$(CH_2)_n$pyrrolidine, —$(CH_2)$furan, and —$(CH_2)_n$thiophene, optionally substituted with up to 3 members, each independently selected from the group consisting of: -guanidyl, -urea, -halo, -alkyl, -hydroxy, -amino, -alkoxy, -2,3-dihydro-1H-pyrrole-1-carboxamide, —$(CH_2)_n$ $NR^{1A}R^{1B}$, —$(CH_2)_nOR^{1C}$, —$(CH_2)_nSR^{1C}$ and —$(CH_2)_n$ $SeR^{1C}$, wherein n is independently an integer selected from 0, 1, 2, 3, and 4;

each $R^{1A}$ is independently selected from the group consisting of: —H—$C_{1-8}$alkyl, —$C_{1-8}$haloalkyl, —$(CH_2)_n$aryl, —$(CH_2)_n$heteroaryl, —$(CH_2)_n$cycloalkyl, and —$(CH_2)_n$heterocycloalkyl, wherein n is independently an integer selected from 0, 1, 2, 3, and 4;

each $R^{1B}$ is independently selected from the group consisting of: —H—$C_{1-8}$haloalkyl, —$(CH_2)_n$aryl, —$(CH_2)_n$heteroaryl, —$(CH_2)_n$cycloalkyl, and —$(CH_2)_n$heterocycloalkyl, wherein n is independently an integer selected from 0, 1, 2, 3, and 4;

each $R^{1C}$ is independently selected from the group consisting of: —H—$C_{1-8}$alkyl, —$C_{1-8}$haloalkyl, —$(CH_2)_n$aryl, —$(CH_2)_n$heteroaryl, —$(CH_2)_n$cycloalkyl, and —$(CH_2)_n$heterocycloalkyl, wherein n is independently an integer selected from 0, 1, 2, 3, and 4;

$R^7$ and $R^8$ are —H; and $R^9$ and $R^{10}$ are independently selected from the group consisting of: —H, —$C_{1-8}$alkyl, and —$C_{1-8}$haloalkyl; or optionally $R^9$ and $R^{10}$ taken together with the carbon to which they are attached can form an optionally substituted five membered heteroaryl or heterocycloalkyl ring.

In some embodiments, $R^1$ includes —H.

In some embodiments, $R^1$ includes —$C_{1-6}$alkyl, optionally substituted with one or more members, each independently selected from the group consisting of: -halo, -hydroxy, -alkoxy, -amino and -carboxyl.

In some embodiments, $R^1$ includes —$C_{3-8}$alkenyl, optionally substituted with one or more members, each independently selected from the group consisting of: -halo, -hydroxy, —$C_{1-4}$ alkyl, —$C_{1-4}$alkoxy, and -amino.

In some embodiments, $R^1$ includes —$C_{3-8}$alkynyl, each optionally substituted with one or more members, each independently selected from the group consisting of: -halo, -hydroxy, —$C_{1-4}$ alkyl, —$C_{1-4}$alkoxy, and -amino.

In some embodiments, $R^1$ includes —$(CH_2)_n$aryl, optionally substituted with one or more members, each independently selected from the group consisting of: -halo, -hydroxy, —$C_{1-4}$ alkyl, —$C_{1-4}$alkoxy, and -amino, wherein n is independently an integer selected from 0, 1, 2, 3, and 4;

In some embodiments, $R^1$ includes —$(CH_2)_n$heteroaryl, optionally substituted with one or more members, each independently selected from the group consisting of: -halo, -hydroxy, —$C_{1-4}$ alkyl, —$C_{1-4}$alkoxy, and -amino; wherein n is independently an integer selected from 0, 1, 2, 3, and 4;

In some embodiments, $R^1$ includes —$(CH_2)_n$cycloalkyl, optionally substituted with one or more members, each independently selected from the group consisting of: -halo, -hydroxy, —$C_{1-4}$ alkyl, —$C_{1-4}$alkoxy, and -amino; wherein n is independently an integer selected from 0, 1, 2, 3, and 4;

In some embodiments, $R^1$ includes —$(CH_2)_n$heterocycloalkyl, optionally substituted with one or more members, each independently selected from the group consisting of: -halo, -hydroxy, —$C_{1-4}$ alkyl, —$C_{1-4}$alkoxy, and -amino; wherein n is independently an integer selected from 0, 1, 2, 3, and 4.

In some embodiments, $R^1$ includes —$COR^2$, wherein $R^2$ is selected from the group consisting of: —H, —$C_{1-8}$alkyl, and —$C_{1-8}$haloalkyl.

In some embodiments, $R^1$ includes —$CONR^3R^4$, wherein $R^3$ and $R^4$ are independently selected from the group consisting of: —H, —$C_{1-8}$alkyl, and —$C_{1-8}$haloalkyl.

In some embodiments, $R^1$ includes —$CR^5R^6NR^7R^8$, wherein $R^7$ and $R^8$ are independently selected from the group consisting of: —H, —$C_{1-8}$alkyl, and —$C_{1-8}$haloalkyl; and $R^5$ and $R^6$ are independently selected from the group consisting of: —H, -halo, —$NH_2$, —$C_{1-8}$alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, wherein n is independently an integer, selected from 0, 1, 2, 3, and 4.

In some embodiments, $R^1$ includes —$CR^5R^6NR^7R^8$, wherein $R^7$ and $R^8$ are independently selected from the group consisting of: —H, —$C_{1-8}$alkyl, and —$C_{1-8}$haloalkyl; and $R^5$ and $R^6$ are each independently selected from the group consisting of: —H, -halo, —$NH_2$, —$C_{1-8}$alkyl, —$C_{1-8}$ haloalkyl, —$(CH_2)_n$ $CONH_2$, —$(CH_2)_n$ COOH, —$(CH_2)_n$ aryl, —$(CH_2)_n$heteroaryl, —$(CH_2)_n$cycloalkyl, and —$(CH_2)_n$ heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, —$(CH_2)_n$ $CONR^{1A}R^{1B}$, —$(CH_2)_n$ $NHC(=O)R^{1A}$, —$(CH_2)_n$ $NR^{1A}R^{1B}$, —$(CH_2)_nOR^{1C}$, —$(CH_2)_n$ $SR^{1C}$ and —$(CH_2)_n$ $SeR^{1C}$, wherein n is independently an integer selected from 0, 1, 2, 3, and 4;

each $R^{1A}$ is independently selected from the group consisting of: —H—$C_{1-8}$alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, said —$(CH_2)_n$aryl, —$(CH_2)_n$heteroaryl, —$(CH_2)_n$ cycloalkyl, and —$(CH_2)_n$heterocycloalkyl each optionally substituted with one or more members, each independently selected from the group consisting of: -halo, -hydroxy, —$C_{1-4}$ alkyl, —$C_{1-4}$alkoxy, and -amino, wherein n is independently an integer selected from 0, 1, 2, 3, and 4;

each $R^{1B}$ is independently selected from the group consisting of: —H—$C_{1-8}$alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, wherein n is independently an integer selected from 0, 1, 2, 3, and 4; and each $R^{1C}$ is independently selected from the group consisting of: —H—$C_{1-8}$alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, wherein n is independently an integer selected from 0, 1, 2, 3, and 4.

In some embodiments, $R^1$ includes —$CHR^9R^{10}$, wherein $R^9$ and $R^{10}$ are independently selected from the group consisting of: —H, —$C_{1-8}$alkyl, —$C_{1-8}$haloalkyl, said alkyl optionally substituted with up to 3-amino, -hydroxy, and -carboxyl groups; or optionally $R^9$ and $R^{10}$ taken together with the carbon to which they are attached can form an optionally substituted five-membered heteroaryl or heterocycloalkyl ring.

In some embodiments, $R^1$ includes —$C(OH)R^{11}R^{12}$, wherein $R^{11}$ and $R^{12}$ are independently selected from the group consisting of: —H, —$C_{1-6}$alkyl and —$C_{1-6}$haloalkyl, optionally substituted with up to 3 members, each independently selected from the group consisting of: -hydroxy and -amino.

In some embodiments, the heteroatom is selected from the group consisting of N (nitrogen), O (oxygen), and S (sulfur).

In some embodiments, the heteroatom is selected from the group consisting of N (nitrogen), O (oxygen), Se (selenium), and S (sulfur).

In some embodiments, the heteroatom includes N (nitrogen).

In some embodiments, the heteroatom includes O (oxygen).

In some embodiments, the heteroatom includes S (sulfur).

In some embodiments, the heteroatom includes Se (selenium).

In some embodiments, the disclosure provides a chemical entity of Formula (I), wherein $R^1$ includes an analog of a naturally occurring amino acid.

In some embodiments, the disclosure provides a chemical entity of Formula (I), wherein $R^1$ includes an analog of a known, non-naturally occurring amino acid. Such known, non-naturally occurring, amino acids include β-amino acids (β3 and β2), homo-amino acids, proline- and pyruvic acid derivatives, triple-substituted alanine derivatives, glycine derivatives, ring-substituted phenylalanine and tyrosine derivatives, linear core amino acids, and N-methyl amino acids.

In some embodiments, the chemical entity is selected from the group consisting of compounds of Formula (I), pharmaceutically acceptable salts of compounds of Formula (I), pharmaceutically acceptable chelates of compounds of Formula (I), pharmaceutically acceptable solvates of compounds of Formula (I), pharmaceutically acceptable metabolites of compounds of Formula (I), and pharmaceutically acceptable prodrugs of compounds of Formula (I).

In some embodiments, the chemical entity is selected from the group consisting of compounds of Formula (I) and pharmaceutically acceptable salts of compounds of Formula (I).

In some embodiments, the disclosure provides a compound selected from the group consisting of:

(1R,5R)-5-(2-chlorophenyl)-2-oxa-4-azabicyclo[3.3.1]non-3-en-9-one;

(1R,5R)-5-(2-chlorophenyl)-3-methyl-2-oxa-4-azabicyclo [3.3.1]non-3-en-9-one;

(1R,5R)-5-(2-chlorophenyl)-3-(1-hydroxyethyl)-2-oxa-4-azabicyclo[3.3.1]non-3-en-9-one;

(1R,5R)-3-((S)-1-amino-2-methylpropyl)-5-(2-chlorophenyl)-2-oxa-4-azabicyclo[3.3.1]non-3-en-9-one;

(1R,5R)-3-(aminomethyl)-5-(2-chlorophenyl)-2-oxa-4-azabicyclo[3.3.1]non-3-en-9-one;

(1R,5R)-5-(2-chlorophenyl)-3-fluorocarbonyl-2-oxa-4-azabicyclo[3.3.1]non-3-en-9-one;

(1R,5R)-5-(2-chlorophenyl)-3-((S)-1,5-diaminopentyl)-2-oxa-4-azabicyclo[3.3.1]non-3-en-9-one;

(1R,5R)-3-((S)-1-aminoethyl)-5-(2-chlorophenyl)-2-oxa-4-azabicyclo[3.3.1]non-3-en-9-one;

(1R,5R)-5-(2-chlorophenyl)-3-phenyl-2-oxa-4-azabicyclo [3.3.1]non-3-en-9-one;

(1R,5R)-3-((1S,2R)-1-amino-2-methylbutyl)-5-(2-chlorophenyl)-2-oxa-4-azabicyclo[3.3.1]non-3-en-9-one;

(1R,5R)-3-((S)-1-amino-3-methylbutyl)-5-(2-chlorophenyl)-2-oxa-4-azabicyclo[3.3.1]non-3-en-9-one;

(1R,5R)-3-((S)-1-amino-2-phenylethyl)-5-(2-chlorophenyl)-2-oxa-4-azabicyclo[3.3.1]non-3-en-9-one;

(1R,5R)-3-((S)-1-amino-2-(4-hydroxyphenyl)ethyl)-5-(2-chlorophenyl)-2-oxa-4-azabicyclo[3.3.1]non-3-en-9-one;

(1R,5R)-3-((S)-1-amino-2-(1H-indol-3-yl)ethyl)-5-(2-chlorophenyl)-2-oxa-4-azabicyclo[3.3.1]non-3-en-9-one;

(1R,5R)-3-((S)-1-amino-2-(1H-imidazol-4-yl)ethyl)-5-(2-chlorophenyl)-2-oxa-4-azabicyclo[3.3.1]non-3-en-9-one;

(1R,5R)-5-(2-chlorophenyl)-3-(pyrrolidin-2-yl)-2-oxa-4-azabicyclo[3.3.1]non-3-en-9-one;

(S)-3-amino-3-((1R,5R)-5-(2-chlorophenyl)-9-oxo-2-oxa-4-azabicyclo[3.3.1]non-3-en-3-yl)propanoic acid;

(S)-4-amino-4-((1R,5R)-5-(2-chlorophenyl)-9-oxo-2-oxa-4-azabicyclo[3.3.1]non-3-en-3-yl)butanoic acid;

(S)-4-amino-4-((1R,5R)-5-(2-chlorophenyl)-9-oxo-2-oxa-4-azabicyclo[3.3.1]non-3-en-3-yl)butanamide;

(S)-3-amino-3-((1R,5R)-5-(2-chlorophenyl)-9-oxo-2-oxa-4-azabicyclo[3.3.1]non-3-en-3-yl)propanamide;

(1R,5R)-3-((S)-1-amino-3-(methylthio)propyl)-5-(2-chlorophenyl)-2-oxa-4-azabicyclo[3.3.1]non-3-en-9-one;

(1R,5R)-3-((R)-1-amino-2-mercaptoethyl)-5-(2-chlorophenyl)-2-oxa-4-azabicyclo[3.3.1]non-3-en-9-one;

(1R,5R)-3-((S)-1-amino-2-hydroxyethyl)-5-(2-chlorophenyl)-2-oxa-4-azabicyclo[3.3.1]non-3-en-9-one;
(1R,5R)-3-((S)-1-amino-2-methoxyethyl)-5-(2-chlorophenyl)-2-oxa-4-azabicyclo[3.3.1]non-3-en-9-one;
1-((S)-4-amino-4-((1R,5R)-5-(2-chlorophenyl)-9-oxo-2-oxa-4-azabicyclo[3.3.1]non-3-en-3-yl)butyl)guanidine;
(1R,5R)-5-(2-chlorophenyl)-3-ethyl-2-oxa-4-azabicyclo[3.3.1]non-3-en-9-one;
3-((1R,5R)-5-(2-chlorophenyl)-9-oxo-2-oxa-4-azabicyclo[3.3.1]non-3-en-3-yl)-2-hydroxypropanoic acid;
2-(((1R,5R)-5-(2-chlorophenyl)-9-oxo-2-oxa-4-azabicyclo[3.3.1]non-3-en-3-yl)methyl)-2-hydroxysuccinic acid;
5-((1R,5R)-5-(2-chlorophenyl)-9-oxo-2-oxa-4-azabicyclo[3.3.1]non-3-en-3-yl)pentanoic acid;
3-((1R,5R)-5-(2-chlorophenyl)-9-oxo-2-oxa-4-azabicyclo[3.3.1]non-3-en-3-yl)-2,3-dihydroxypropanoic acid;
3-((1R,5R)-5-(2-chlorophenyl)-9-oxo-2-oxa-4-azabicyclo[3.3.1]non-3-en-3-yl)propanoic acid;
(1R,5R)-5-(2-chlorophenyl)-3-heptyl-2-oxa-4-azabicyclo[3.3.1]non-3-en-9-one;
(1R,5R)-3-(1-amino-2-hydroselenoethyl)-5-(2-chlorophenyl)-2-oxa-4-azabicyclo[3.3.1]non-3-en-9-one;
(1R,5R)-5-(2-chlorophenyl)-3-(2-(methylamino)ethyl)-2-oxa-4-azabicyclo[3.3.1]non-3-en-9-one;
(1R,5R)-5-(2-chlorophenyl)-3-(1,2-diaminoethyl)-2-oxa-4-azabicyclo[3.3.1]non-3-en-9-one;
(1R,5R)-3-(2-amino-1-hydroxyethyl)-5-(2-chlorophenyl)-2-oxa-4-azabicyclo[3.3.1]non-3-en-9-one;
(1R,5R)-3-(3-aminopropyl)-5-(2-chlorophenyl)-2-oxa-4-azabicyclo[3.3.1]non-3-en-9-one;
(1R,5R)-3-(4-aminobutyl)-5-(2-chlorophenyl)-2-oxa-4-azabicyclo[3.3.1]non-3-en-9-one;
(1R,5R)-3-(3-aminopentyl)-5-(2-chlorophenyl)-2-oxa-4-azabicyclo[3.3.1]non-3-en-9-one;
(1R,5R)-3-(1-amino-3-hydroxypropyl)-5-(2-chlorophenyl)-2-oxa-4-azabicyclo[3.3.1]non-3-en-9-one;
(1R,5R)-5-(2-chlorophenyl)-3-(1,4-diaminobutyl)-2-oxa-4-azabicyclo[3.3.1]non-3-en-9-one;
4-amino-4-((1R,5R)-5-(2-chlorophenyl)-9-oxo-2-oxa-4-azabicyclo[3.3.1]non-3-en-3-yl)-N-ethylbutanamide;
(1R,5R)-5-(2-chlorophenyl)-3-(1,5-diamino-4-hydroxypentyl)-2-oxa-4-azabicyclo[3.3.1]non-3-en-9-one;
1-(4-amino-4-((1R,5R)-5-(2-chlorophenyl)-9-oxo-2-oxa-4-azabicyclo[3.3.1]non-3-en-3-yl)butyl)urea;
1-(5-amino-5-((1R,5R)-5-(2-chlorophenyl)-9-oxo-2-oxa-4-azabicyclo[3.3.1]non-3-en-3-yl)pentyl)urea;
1-(5-amino-5-((1R,5R)-5-(2-chlorophenyl)-9-oxo-2-oxa-4-azabicyclo[3.3.1]non-3-en-3-yl)pentyl)guanidine;
1-(2-((1R,5R)-5-(2-chlorophenyl)-9-oxo-2-oxa-4-azabicyclo[3.3.1]non-3-en-3-yl)ethyl)guanidine;
(1R,5R)-3-(1-amino-2-methylbutyl)-5-(2-chlorophenyl)-2-oxa-4-azabicyclo[3.3.1]non-3-en-9-one;
(1R,5R)-3-(1-amino-2-(5-hydroxy-1H-indol-3-yl)ethyl)-5-(2-chlorophenyl)-2-oxa-4-azabicyclo[3.3.1]non-3-en-9-one;
(1R,5R)-3-(1-amino-2-(5-methyl-1H-indol-3-yl)ethyl)-5-(2-chlorophenyl)-2-oxa-4-azabicyclo[3.3.1]non-3-en-9-one;
(1R,5R)-3-(2-(1H-indol-3-yl)-1-(methylamino)ethyl)-5-(2-chlorophenyl)-2-oxa-4-azabicyclo[3.3.1]non-3-en-9-one;
(1R,5R)-5-(2-chlorophenyl)-3-(4-hydroxypyrrolidin-2-yl)-2-oxa-4-azabicyclo[3.3.1]non-3-en-9-one;
(1R,5R)-3-(1-amino-2-hydroxy-3-methylbutyl)-5-(2-chlorophenyl)-2-oxa-4-azabicyclo[3.3.1]non-3-en-9-one;
(1R,5R)-5-(2-chlorophenyl)-3-(1-(methylamino)ethyl)-2-oxa-4-azabicyclo[3.3.1]non-3-en-9-one;
(1R,5R)-3-(2-aminopropyl)-5-(2-chlorophenyl)-2-oxa-4-azabicyclo[3.3.1]non-3-en-9-one;
N-(5-amino-5-((1R,5R)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;
(1R,5R)-3-(1-amino-3-hydroxy-2-methylbutyl)-5-(2-chlorophenyl)-2-oxa-4-azabicyclo[3.3.1]non-3-en-9-one;
(1R,5R)-3-(1-amino-2,2-dimethylpropyl)-5-(2-chlorophenyl)-2-oxa-4-azabicyclo[3.3.1]non-3-en-9-one;
(1R,5R)-3-(amino(3-amino-4-hydroxyphenyl)methyl)-5-(2-chlorophenyl)-2-oxa-4-azabicyclo[3.3.1]non-3-en-9-one;
(1R,5R)-3-(1-amino-2-hydroxy-2-phenylethyl)-5-(2-chlorophenyl)-2-oxa-4-azabicyclo[3.3.1]non-3-en-9-one; and
(1R,5R)-3-(1-amino-2-(4-methoxyphenyl)ethyl)-5-(2-chlorophenyl)-2-oxa-4-azabicyclo[3.3.1]non-3-en-9-one;
or
pharmaceutically acceptable salts thereof.

In some embodiments, the disclosure provides a compound selected from the group consisting of:
(1S,5S)-5-(2-chlorophenyl)-2-oxa-4-azabicyclo[3.3.1]non-3-en-9-one;
(1S,5S)-5-(2-chlorophenyl)-3-methyl-2-oxa-4-azabicyclo[3.3.1]non-3-en-9-one;
(1S,5S)-5-(2-chlorophenyl)-3-(1-hydroxyethyl)-2-oxa-4-azabicyclo[3.3.1]non-3-en-9-one;
(1S,5S)-3-((S)-1-amino-2-methylpropyl)-5-(2-chlorophenyl)-2-oxa-4-azabicyclo[3.3.1]non-3-en-9-one;
(1S,5S)-3-(aminomethyl)-5-(2-chlorophenyl)-2-oxa-4-azabicyclo[3.3.1]non-3-en-9-one;
(1S,5S)-5-(2-chlorophenyl)-3-fluorocarbonyl-2-oxa-4-azabicyclo[3.3.1]non-3-en-9-one;
(1S,5S)-5-(2-chlorophenyl)-3-((S)-1,5-diaminopentyl)-2-oxa-4-azabicyclo[3.3.1]non-3-en-9-one;
(1S,5S)-3-((S)-1-aminoethyl)-5-(2-chlorophenyl)-2-oxa-4-azabicyclo[3.3.1]non-3-en-9-one;
(1S,5S)-5-(2-chlorophenyl)-3-phenyl-2-oxa-4-azabicyclo[3.3.1]non-3-en-9-one;
(1S,5S)-3-((1S,2R)-1-amino-2-methylbutyl)-5-(2-chlorophenyl)-2-oxa-4-azabicyclo[3.3.1]non-3-en-9-one;
(1S,5S)-3-((S)-1-amino-3-methylbutyl)-5-(2-chlorophenyl)-2-oxa-4-azabicyclo[3.3.1]non-3-en-9-one;
(1S,5S)-3-((S)-1-amino-2-phenylethyl)-5-(2-chlorophenyl)-2-oxa-4-azabicyclo[3.3.1]non-3-en-9-one;
(1S,5S)-3-((S)-1-amino-2-(4-hydroxyphenyl)ethyl)-5-(2-chlorophenyl)-2-oxa-4-azabicyclo[3.3.1]non-3-en-9-one;
(1S,5S)-3-((S)-1-amino-2-(1H-indol-3-yl)ethyl)-5-(2-chlorophenyl)-2-oxa-4-azabicyclo[3.3.1]non-3-en-9-one;
(1S,5S)-3-((S)-1-amino-2-(1H-imidazol-4-yl)ethyl)-5-(2-chlorophenyl)-2-oxa-4-azabicyclo[3.3.1]non-3-en-9-one;
(1S,5S)-5-(2-chlorophenyl)-3-(pyrrolidin-2-yl)-2-oxa-4-azabicyclo[3.3.1]non-3-en-9-one;
(S)-3-amino-3-((1S,5S)-5-(2-chlorophenyl)-9-oxo-2-oxa-4-azabicyclo[3.3.1]non-3-en-3-yl)propanoic acid;
(S)-4-amino-4-((1S,5S)-5-(2-chlorophenyl)-9-oxo-2-oxa-4-azabicyclo[3.3.1]non-3-en-3-yl)butanoic acid;
(S)-4-amino-4-((1S,5S)-5-(2-chlorophenyl)-9-oxo-2-oxa-4-azabicyclo[3.3.1]non-3-en-3-yl)butanamide;
(S)-3-amino-3-((1S,5S)-5-(2-chlorophenyl)-9-oxo-2-oxa-4-azabicyclo[3.3.1]non-3-en-3-yl)propanamide;
(1S,5S)-3-((S)-1-amino-3-(methylthio)propyl)-5-(2-chlorophenyl)-2-oxa-4-azabicyclo[3.3.1]non-3-en-9-one;
(1S,5S)-3-((R)-1-amino-2-mercaptoethyl)-5-(2-chlorophenyl)-2-oxa-4-azabicyclo[3.3.1]non-3-en-9-one;
(1S,5S)-3-((S)-1-amino-2-hydroxyethyl)-5-(2-chlorophenyl)-2-oxa-4-azabicyclo[3.3.1]non-3-en-9-one;
(1S,5S)-3-((S)-1-amino-2-methoxyethyl)-5-(2-chlorophenyl)-2-oxa-4-azabicyclo[3.3.1]non-3-en-9-one;

1-((S)-4-amino-4-((1S,5S)-5-(2-chlorophenyl)-9-oxo-2-oxa-4-azabicyclo[3.3.1]non-3-en-3-yl)butyl)guanidine;
(1S,5S)-5-(2-chlorophenyl)-3-ethyl-2-oxa-4-azabicyclo[3.3.1]non-3-en-9-one;
3-((1S,5S)-5-(2-chlorophenyl)-9-oxo-2-oxa-4-azabicyclo[3.3.1]non-3-en-3-yl)-2-hydroxypropanoic acid;
2-(((1S,5S)-5-(2-chlorophenyl)-9-oxo-2-oxa-4-azabicyclo[3.3.1]non-3-en-3-yl)methyl)-2-hydroxysuccinic acid;
5-((1S,5S)-5-(2-chlorophenyl)-9-oxo-2-oxa-4-azabicyclo[3.3.1]non-3-en-3-yl)pentanoic acid;
3-((1S,5S)-5-(2-chlorophenyl)-9-oxo-2-oxa-4-azabicyclo[3.3.1]non-3-en-3-yl)-2,3-dihydroxypropanoic acid;
3-((1S,5S)-5-(2-chlorophenyl)-9-oxo-2-oxa-4-azabicyclo[3.3.1]non-3-en-3-yl)propanoic acid;
(1S,5S)-5-(2-chlorophenyl)-3-heptyl-2-oxa-4-azabicyclo[3.3.1]non-3-en-9-one;
(1S,5S)-3-(1-amino-2-hydroselenoethyl)-5-(2-chlorophenyl)-2-oxa-4-azabicyclo[3.3.1]non-3-en-9-one;
(1S,5S)-5-(2-chlorophenyl)-3-(2-(methylamino)ethyl)-2-oxa-4-azabicyclo[3.3.1]non-3-en-9-one;
(1S,5S)-5-(2-chlorophenyl)-3-(1,2-diaminoethyl)-2-oxa-4-azabicyclo[3.3.1]non-3-en-9-one;
(1S,5S)-3-(2-amino-1-hydroxyethyl)-5-(2-chlorophenyl)-2-oxa-4-azabicyclo[3.3.1]non-3-en-9-one;
(1S,5S)-3-(3-aminopropyl)-5-(2-chlorophenyl)-2-oxa-4-azabicyclo[3.3.1]non-3-en-9-one;
(1S,5S)-3-(4-aminobutyl)-5-(2-chlorophenyl)-2-oxa-4-azabicyclo[3.3.1]non-3-en-9-one;
(1S,5S)-3-(3-aminopentyl)-5-(2-chlorophenyl)-2-oxa-4-azabicyclo[3.3.1]non-3-en-9-one;
(1S,5S)-3-(1-amino-3-hydroxypropyl)-5-(2-chlorophenyl)-2-oxa-4-azabicyclo[3.3.1]non-3-en-9-one;
(1S,5S)-5-(2-chlorophenyl)-3-(1,4-diaminobutyl)-2-oxa-4-azabicyclo[3.3.1]non-3-en-9-one;
4-amino-4-((1S,5S)-5-(2-chlorophenyl)-9-oxo-2-oxa-4-azabicyclo[3.3.1]non-3-en-3-yl)-N-ethylbutanamide;
(1S,5S)-5-(2-chlorophenyl)-3-(1, 5-diamino-4-hydroxypentyl)-2-oxa-4-azabicyclo[3.3.1]non-3-en-9-one;
1-(4-amino-4-((1S,5S)-5-(2-chlorophenyl)-9-oxo-2-oxa-4-azabicyclo[3.3.1]non-3-en-3-yl)butyl)urea;
1-(5-amino-5-((1S,5S)-5-(2-chlorophenyl)-9-oxo-2-oxa-4-azabicyclo[3.3.1]non-3-en-3-yl)pentyl)urea;
1-(5-amino-5-((1S,5S)-5-(2-chlorophenyl)-9-oxo-2-oxa-4-azabicyclo[3.3.1]non-3-en-3-yl)pentyl)guanidine;
1-(2-((1S,5S)-5-(2-chlorophenyl)-9-oxo-2-oxa-4-azabicyclo[3.3.1]non-3-en-3-yl)ethyl)guanidine;
(1S,5S)-3-(1-amino-2-methylbutyl)-5-(2-chlorophenyl)-2-oxa-4-azabicyclo[3.3.1]non-3-en-9-one;
(1S,5S)-3-(1-amino-2-(5-hydroxy-1H-indol-3-yl)ethyl)-5-(2-chlorophenyl)-2-oxa-4-azabicyclo[3.3.1]non-3-en-9-one;
(1S,5S)-3-(1-amino-2-(5-methyl-1H-indol-3-yl)ethyl)-5-(2-chlorophenyl)-2-oxa-4-azabicyclo[3.3.1]non-3-en-9-one;
(1S,5S)-3-(2-(1H-indol-3-yl)-1-(methylamino)ethyl)-5-(2-chlorophenyl)-2-oxa-4-azabicyclo[3.3.1]non-3-en-9-one;
(1S,5S)-5-(2-chlorophenyl)-3-(4-hydroxypyrrolidin-2-yl)-2-oxa-4-azabicyclo[3.3.1]non-3-en-9-one;
(1S,5S)-3-(1-amino-2-hydroxy-3-methylbutyl)-5-(2-chlorophenyl)-2-oxa-4-azabicyclo[3.3.1]non-3-en-9-one;
(1S,5S)-5-(2-chlorophenyl)-3-(1-(methylamino)ethyl)-2-oxa-4-azabicyclo[3.3.1]non-3-en-9-one;
(1S,5S)-3-(2-aminopropyl)-5-(2-chlorophenyl)-2-oxa-4-azabicyclo[3.3.1]non-3-en-9-one;
N-(5-amino-5-((1S,5S)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;
(1S,5S)-3-(1-amino-3-hydroxy-2-methylbutyl)-5-(2-chlorophenyl)-2-oxa-4-azabicyclo[3.3.1]non-3-en-9-one;
(1S,5S)-3-(1-amino-2,2-dimethylpropyl)-5-(2-chlorophenyl)-2-oxa-4-azabicyclo[3.3.1]non-3-en-9-one;
(1S,5S)-3-(amino(3-amino-4-hydroxyphenyl)methyl)-5-(2-chlorophenyl)-2-oxa-4-azabicyclo[3.3.1]non-3-en-9-one;
(1S,5S)-3-(1-amino-2-hydroxy-2-phenylethyl)-5-(2-chlorophenyl)-2-oxa-4-azabicyclo[3.3.1]non-3-en-9-one; and
(1S,5S)-3-(1-amino-2-(4-methoxyphenyl)ethyl)-5-(2-chlorophenyl)-2-oxa-4-azabicyclo[3.3.1]non-3-en-9-one;
or
pharmaceutically acceptable salts thereof.

In some embodiments, the disclosure provides a compound selected from the group consisting of:
(1R,5R)-5-(2-chlorophenyl)-2-oxa-4-azabicyclo[3.3.1]non-3-en-9-one;
(1R,5R)-5-(2-chlorophenyl)-3-methyl-2-oxa-4-azabicyclo[3.3.1]non-3-en-9-one;
(1R,5R)-5-(2-chlorophenyl)-3-(1-hydroxyethyl)-2-oxa-4-azabicyclo[3.3.1]non-3-en-9-one;
(1R,5R)-3-((S)-1-amino-2-methylpropyl)-5-(2-chlorophenyl)-2-oxa-4-azabicyclo[3.3.1]non-3-en-9-one;
(1R,5R)-3-(aminomethyl)-5-(2-chlorophenyl)-2-oxa-4-azabicyclo[3.3.1]non-3-en-9-one;
(1R,5R)-5-(2-chlorophenyl)-3-fluorocarbonyl-2-oxa-4-azabicyclo[3.3.1]non-3-en-9-one;
(1R,5R)-5-(2-chlorophenyl)-3-((S)-1,5-diaminopentyl)-2-oxa-4-azabicyclo[3.3.1]non-3-en-9-one;
(1R,5R)-3-((S)-1-aminoethyl)-5-(2-chlorophenyl)-2-oxa-4-azabicyclo[3.3.1]non-3-en-9-one;
(1R,5R)-5-(2-chlorophenyl)-3-phenyl-2-oxa-4-azabicyclo[3.3.1]non-3-en-9-one;
(1R,5R)-3-((1S,2R)-1-amino-2-methylbutyl)-5-(2-chlorophenyl)-2-oxa-4-azabicyclo[3.3.1]non-3-en-9-one;
(1R,5R)-3-((S)-1-amino-3-methylbutyl)-5-(2-chlorophenyl)-2-oxa-4-azabicyclo[3.3.1]non-3-en-9-one;
(1R,5R)-3-((S)-1-amino-2-phenylethyl)-5-(2-chlorophenyl)-2-oxa-4-azabicyclo[3.3.1]non-3-en-9-one;
(1R,5R)-3-((S)-1-amino-2-(4-hydroxyphenyl)ethyl)-5-(2-chlorophenyl)-2-oxa-4-azabicyclo[3.3.1]non-3-en-9-one;
(1R,5R)-3-((S)-1-amino-2-(1H-indol-3-yl)ethyl)-5-(2-chlorophenyl)-2-oxa-4-azabicyclo[3.3.1]non-3-en-9-one;
(1R,5R)-3-((S)-1-amino-2-(1H-imidazol-4-yl)ethyl)-5-(2-chlorophenyl)-2-oxa-4-azabicyclo[3.3.1]non-3-en-9-one;
(1R,5R)-5-(2-chlorophenyl)-3-(pyrrolidin-2-yl)-2-oxa-4-azabicyclo[3.3.1]non-3-en-9-one;
(S)-3-amino-3-((1R,5R)-5-(2-chlorophenyl)-9-oxo-2-oxa-4-azabicyclo[3.3.1]non-3-en-3-yl)propanoic acid;
(S)-4-amino-4-((1R,5R)-5-(2-chlorophenyl)-9-oxo-2-oxa-4-azabicyclo[3.3.1]non-3-en-3-yl)butanoic acid;
(S)-4-amino-4-((1R,5R)-5-(2-chlorophenyl)-9-oxo-2-oxa-4-azabicyclo[3.3.1]non-3-en-3-yl)butanamide;
(S)-3-amino-3-((1R,5R)-5-(2-chlorophenyl)-9-oxo-2-oxa-4-azabicyclo[3.3.1]non-3-en-3-yl)propanamide;
(1R,5R)-3-((S)-1-amino-3-(methylthio)propyl)-5-(2-chlorophenyl)-2-oxa-4-azabicyclo[3.3.1]non-3-en-9-one;
(1R,5R)-3-((R)-1-amino-2-mercaptoethyl)-5-(2-chlorophenyl)-2-oxa-4-azabicyclo[3.3.1]non-3-en-9-one;
(1R,5R)-3-((S)-1-amino-2-hydroxyethyl)-5-(2-chlorophenyl)-2-oxa-4-azabicyclo[3.3.1]non-3-en-9-one;

(1R,5R)-3-((S)-1-amino-2-methoxyethyl)-5-(2-chlorophenyl)-2-oxa-4-azabicyclo[3.3.1]non-3-en-9-one; and
1-((S)-4-amino-4-((1R,5R)-5-(2-chlorophenyl)-9-oxo-2-oxa-4-azabicyclo[3.3.1]non-3-en-3-yl)butyl)guanidine;
or
pharmaceutically acceptable salts thereof.

In some embodiments, the disclosure provides a compound selected from the group consisting of:
(1R,5R)-5-(2-chlorophenyl)-2-oxa-4-azabicyclo[3.3.1]non-3-en-9-one;
(1R,5R)-5-(2-chlorophenyl)-3-methyl-2-oxa-4-azabicyclo[3.3.1]non-3-en-9-one;
(1R,5R)-5-(2-chlorophenyl)-3-(1-hydroxyethyl)-2-oxa-4-azabicyclo[3.3.1]non-3-en-9-one;
(1R,5R)-3-((S)-1-amino-2-methylpropyl)-5-(2-chlorophenyl)-2-oxa-4-azabicyclo[3.3.1]non-3-en-9-one;
(1R,5R)-3-(aminomethyl)-5-(2-chlorophenyl)-2-oxa-4-azabicyclo[3.3.1]non-3-en-9-one;
(1R,5R)-5-(2-chlorophenyl)-3-fluorocarbonyl-2-oxa-4-azabicyclo[3.3.1]non-3-en-9-one;
(1R,5R)-5-(2-chlorophenyl)-3-((S)-1, 5-diaminopentyl)-2-oxa-4-azabicyclo[3.3.1]non-3-en-9-one; and
(1R,5R)-3-((S)-1-aminoethyl)-5-(2-chlorophenyl)-2-oxa-4-azabicyclo[3.3.1]non-3-en-9-one;
or
pharmaceutically acceptable salts thereof.

In some embodiments, the disclosure provides a compound selected from the group consisting of:
(1R,5R)-3-(1-amino-2-hydroselenoethyl)-5-(2-chlorophenyl)-2-oxa-4-azabicyclo[3.3.1]non-3-en-9-one;
(1R,5R)-5-(2-chlorophenyl)-3-(2-(methylamino)ethyl)-2-oxa-4-azabicyclo[3.3.1]non-3-en-9-one;
(1R,5R)-5-(2-chlorophenyl)-3-(1,2-diaminoethyl)-2-oxa-4-azabicyclo[3.3.1]non-3-en-9-one; (1R,5R)-3-(2-amino-1-hydroxyethyl)-5-(2-chlorophenyl)-2-oxa-4-azabicyclo[3.3.1]non-3-en-9-one;
(1R,5R)-3-(3-aminopropyl)-5-(2-chlorophenyl)-2-oxa-4-azabicyclo[3.3.1]non-3-en-9-one;
(1R,5R)-3-(4-aminobutyl)-5-(2-chlorophenyl)-2-oxa-4-azabicyclo[3.3.1]non-3-en-9-one;
(1R,5R)-3-(3-aminopentyl)-5-(2-chlorophenyl)-2-oxa-4-azabicyclo[3.3.1]non-3-en-9-one;
(1R,5R)-3-(1-amino-3-hydroxypropyl)-5-(2-chlorophenyl)-2-oxa-4-azabicyclo[3.3.1]non-3-en-9-one;
(1R,5R)-5-(2-chlorophenyl)-3-(1,4-diaminobutyl)-2-oxa-4-azabicyclo[3.3.1]non-3-en-9-one;
4-amino-4-((1R,5R)-5-(2-chlorophenyl)-9-oxo-2-oxa-4-azabicyclo[3.3.1]non-3-en-3-yl)-N-ethylbutanamide;
(1R,5R)-5-(2-chlorophenyl)-3-(1,5-diamino-4-hydroxypentyl)-2-oxa-4-azabicyclo[3.3.1]non-3-en-9-one;
1-(4-amino-4-((1R,5R)-5-(2-chlorophenyl)-9-oxo-2-oxa-4-azabicyclo[3.3.1]non-3-en-3-yl)butyl)urea;
1-(5-amino-5-((1R,5R)-5-(2-chlorophenyl)-9-oxo-2-oxa-4-azabicyclo[3.3.1]non-3-en-3-yl)pentyl)urea;
1-(5-amino-5-((1R,5R)-5-(2-chlorophenyl)-9-oxo-2-oxa-4-azabicyclo[3.3.1]non-3-en-3-yl)pentyl)guanidine;
1-(2-((1R,5R)-5-(2-chlorophenyl)-9-oxo-2-oxa-4-azabicyclo[3.3.1]non-3-en-3-yl)ethyl)guanidine;
(1R,5R)-3-(1-amino-2-methylbutyl)-5-(2-chlorophenyl)-2-oxa-4-azabicyclo[3.3.1]non-3-en-9-one;
(1R,5R)-3-(1-amino-2-(5-hydroxy-1H-indol-3-yl)ethyl)-5-(2-chlorophenyl)-2-oxa-4-azabicyclo[3.3.1]non-3-en-9-one;
(1R,5R)-3-(1-amino-2-(5-methyl-1H-indol-3-yl)ethyl)-5-(2-chlorophenyl)-2-oxa-4-azabicyclo[3.3.1]non-3-en-9-one;

(1R,5R)-3-(2-(1H-indol-3-yl)-1-(methylamino)ethyl)-5-(2-chlorophenyl)-2-oxa-4-azabicyclo[3.3.1]non-3-en-9-one;
(1R,5R)-5-(2-chlorophenyl)-3-(4-hydroxypyrrolidin-2-yl)-2-oxa-4-azabicyclo[3.3.1]non-3-en-9-one;
(1R,5R)-3-(1-amino-2-hydroxy-3-methylbutyl)-5-(2-chlorophenyl)-2-oxa-4-azabicyclo[3.3.1]non-3-en-9-one;
(1R,5R)-5-(2-chlorophenyl)-3-(1-(methylamino)ethyl)-2-oxa-4-azabicyclo[3.3.1]non-3-en-9-one;
(1R,5R)-3-(2-aminopropyl)-5-(2-chlorophenyl)-2-oxa-4-azabicyclo[3.3.1]non-3-en-9-one;
N-(5-amino-5-((1R,5R)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;
(1R,5R)-3-(1-amino-3-hydroxy-2-methylbutyl)-5-(2-chlorophenyl)-2-oxa-4-azabicyclo[3.3.1]non-3-en-9-one;
(1R,5R)-3-(1-amino-2,2-dimethylpropyl)-5-(2-chlorophenyl)-2-oxa-4-azabicyclo[3.3.1]non-3-en-9-one;
(1R,5R)-3-(amino(3-amino-4-hydroxyphenyl)methyl)-5-(2-chlorophenyl)-2-oxa-4-azabicyclo[3.3.1]non-3-en-9-one;
(1R,5R)-3-(1-amino-2-hydroxy-2-phenyl ethyl)-5-(2-chlorophenyl)-2-oxa-4-azabicyclo[3.3.1]non-3-en-9-one; and
(1R,5R)-3-(1-amino-2-(4-methoxyphenyl)ethyl)-5-(2-chlorophenyl)-2-oxa-4-azabicyclo[3.3.1]non-3-en-9-one;
or
pharmaceutically acceptable salts thereof.

In some embodiments, the disclosure provides a compound selected from the group consisting of:
(1R,5R)-5-(2-chlorophenyl)-3-ethyl-2-oxa-4-azabicyclo[3.3.1]non-3-en-9-one;
3-((1R,5R)-5-(2-chlorophenyl)-9-oxo-2-oxa-4-azabicyclo[3.3.1]non-3-en-3-yl)-2-hydroxypropanoic acid;
2-(((1R,5R)-5-(2-chlorophenyl)-9-oxo-2-oxa-4-azabicyclo[3.3.1]non-3-en-3-yl)methyl)-2-hydroxysuccinic acid;
5-((1R,5R)-5-(2-chlorophenyl)-9-oxo-2-oxa-4-azabicyclo[3.3.1]non-3-en-3-yl)pentanoic acid;
3-((1R,5R)-5-(2-chlorophenyl)-9-oxo-2-oxa-4-azabicyclo[3.3.1]non-3-en-3-yl)-2,3-dihydroxypropanoic acid;
3-((1R,5R)-5-(2-chlorophenyl)-9-oxo-2-oxa-4-azabicyclo[3.3.1]non-3-en-3-yl)propanoic acid; and
(1R,5R)-5-(2-chlorophenyl)-3-heptyl-2-oxa-4-azabicyclo[3.3.1]non-3-en-9-one;
or
pharmaceutically acceptable salts thereof.

In some embodiments, a chemical entity of the present disclosure includes an amino acid conjugate. Preferably, the amino acids of the present technology are Generally Regarded As Safe (GRAS) or non-toxic at the concentrations released into the systemic circulation.

Amino acids suitable for use in compounds and compositions can be broadly classified into standard amino acids, non-standard amino acids, and synthetic amino acids.

Standard amino acids, or proteinogenic amino acids, include but are not limited to the currently known amino acids that make up the monomeric units of proteins that are encoded in the universal genetic code of organisms. Standard amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Non-standard amino acids are not encoded by the standard genetic code and include chemical modifications of standard amino acids already incorporated in the proteins, as well as amino acids not found in proteins but still present in living organisms. Examples of non-standard amino acids include ornithine, homoarginine, citrulline, homocitrulline, homoserine, theanine, γ-aminobutyric acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid. Non-standard amino acids also include selenocysteine and pyrrolysine, which are incorporated into proteins by unique synthetic mechanisms.

Synthetic amino acids do not occur in nature and must be synthesized. Examples of synthetic amino acids include allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-aminophenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, and 4-(dimethylamino)cinnamic acid.

In some embodiments, a chemical entity of the present disclosure includes a carboxylic acid conjugate. Preferably, the carboxylic acids of the present disclosure are Generally Regarded As Safe (GRAS) or non-toxic at the concentrations released into the systemic circulation.

In some embodiments, Formula (I) compounds are hydrolyzed chemically, enzymatically or by a combination of chemical and enzymatic processes, and release HNK upon administration to a subject. In some embodiments, Formula (I) compounds may be pharmacologically inactive or have pharmacological activity that is limited or different from HNK, and consequently, in certain embodiments, may follow a metabolic pathway that differs from HNK.

In some embodiments, the chemical entity is a salt, solvate, conformer, polymorph, or a prodrug of a compound of Formula (I).

Salts

In some embodiments, the disclosure provides pharmaceutically acceptable salts of the compounds represented by Formula (I), and the use of such salts in methods of the present invention.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Solvates

In some embodiments, the disclosure provides a solvate of a compound of Formula (I), or a solvate of a pharmaceutically acceptable salt of a compound of Formula (I), and the use of such solvates in methods of present invention.

Solvates can be formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (5)-propylene glycol, (R)-propylene glycol, 1,4-butyne-diol, and the like. Hydrates include compounds formed by an incorporation of one or more water molecules.

Polymorphs

In certain embodiments, compounds of Formula (I) may exist in crystalline form. A polymorph (or crystalline form) is a composition having the same chemical formula, but a different solid state or crystal structure. In addition, certain crystalline forms of compounds of Formula (I) or pharmaceutically acceptable salts of compounds of Formula (I) are obtainable as co-crystals.

Prodrugs

The term "prodrug" means a precursor of a designated compound that, following administration to a subject, yields the compound in vivo via one or more physiochemical or physiological processes, such as chemical hydrolysis or enzymatic cleavage. In some embodiments, more than one process may be required to yield the compound in vivo. For example, a compound of Formula (I), upon administration in vivo, may undergo both hydrolysis and enzymatic conversion.

In some embodiments, the chemical entities of Formula (I) are prodrugs designed to yield, in vivo, a suitable yield of the ketamine metabolite, HNK. That is, in some embodiments, chemical entities of Formula (I) are precursors of HNK and therefore can yield biologically available HNK upon administration to a subject.

In some embodiments, prodrugs may be obtained from further derivatization of compounds of Formula (I). Prodrugs may be generated using techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers). Prodrugs may be produced, for instance, by derivatizing free carboxyl groups of structures of Formula (I) as amides or alkyl esters, or by derivatizing free hydroxy groups using groups including hemisuccinates, phosphate esters, dimethylaminoacetates, and phosphoryloxymethyloxycarbonyls, following procedures such as those outlined in Fleisher et al., Adv. Drug Delivery Rev. 1996, 19, 115-130.

Metabolites

The present disclosure also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., J. Med. Chem. 1997, 40, 2011-2016; Shan et al., J. Pharm. Sci. 1997, 86, 765-767; Bagshawe, Drug Dev. Res. 1995, 34, 220-230; and Bodor, Adv Drug Res. 1984, 13, 224-231).

In preferred embodiments, the metabolite corresponds to HNK. Without being limited by mechanism, compounds of Formula (I) may undergo one or more physiological processes following administration, resulting in HNK and other byproducts. In some embodiments, the byproduct of such processes may include an amino acid or carboxylic acid.

Compositions

Compounds disclosed herein can be administered as the neat chemical, but are preferably administered as a composition. The term "composition," as in pharmaceutical composition, is intended to encompass a product comprising the active ingredient(s) and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients.

Accordingly, in some embodiments, the disclosure provides a pharmaceutical composition comprising a chemical entity of any of the embodiments and examples disclosed herein; and a pharmaceutically acceptable carrier. In some embodiments, a pharmaceutical composition comprises a compound, or pharmaceutically acceptable salt thereof, of any of the embodiments and examples disclosed herein; and a pharmaceutically acceptable carrier. In specific embodiments, a pharmaceutical composition comprises a compound of any one of Examples 1-61; and a pharmaceutically acceptable carrier.

The pharmaceutical composition may contain a compound or salt of Formula (I) as the only active agent, but preferably contains at least one additional active agent. In certain embodiments the pharmaceutical composition is an oral dosage form that contains from about 0.1 mg to about 1000 mg, from about 1 mg to about 500 mg, or from about 10 mg to about 200 mg of a compound of Formula (I) and optionally from about 0.1 mg to about 2000 mg, from about 10 mg to about 1000 mg, from about 100 mg to about 800 mg, or from about 200 mg to about 600 mg of an additional active agent in a unit dosage form.

In some embodiments, compounds of Formula (I), and pharmaceutically acceptable salts thereof, are used, alone or in combination with one or more additional active ingredients, to formulate pharmaceutical compositions.

Formulations and Administration

Procedures for preparing various formulations suitable for administering are known in the art. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, buccal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Some carriers may be listed in more than one class, for example vegetable oil may be used as a lubricant in some formulations and a diluent in others. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or a similar edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Carriers may include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Useful solid carriers may include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The pharmaceutical compositions can be formulated for oral administration. Preferred oral dosage forms are formulated for once a day or twice a day administration. The compositions contain between 0.1 and 99% weight of a compound of Formula (I). In some embodiments, compositions contain at least about 5% weight of a compound of Formula (I). In some embodiments, compositions contain from about 25% to about 50% weight of a compound of Formula (I), or about 5% to 75% weight of a compound of Formula (I).

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of Formula (I) can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

In certain embodiments a therapeutically effect amount is an amount that provide a plasma Cmax of HNK of about of 0.25 mcg/mL to about 125 mcg/mL, or about 1 mcg/mL to about 50 mcg/mL.

Methods and Uses

Uses of Isotopically-Labeled Compounds

In one aspect, the present invention provides a method of using isotopically labeled compounds the present invention in: (i) metabolic studies (preferably with $^{14}C$), reaction kinetic studies (with, for example $^2H$ or $^3H$); (ii) detection or imaging techniques, including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^2H$) may afford certain therapeutic advantages resulting from greater metabolic stability, for example increased in vivo half-life or reduced dosage requirements.

Recent research suggests that low-dose ketamine can act as a novel, rapid-acting antidepressant [Naughton et al. 2014]. In fact, a single subanesthetic dose infusion of ketamine has rapid and potent antidepressant effects in treatment-resistant major depression and bipolar depression [Iadarola et al. 2015]. Ketamine as an antidepressant agent is of great interest as an alternative to the delayed onset to efficacy, repeated administration and unwanted side effects of current pharmacotherapeutics, behavioral therapies and electroconvulsive therapy (ECT).

Therapeutic Methods

Generally

In some embodiments, chemical entities of the present invention are useful in methods (or in the manufacture of a medicament or composition for use in such methods) of treating certain disorders by administering to a subject in need thereof an effective amount of a chemical entity of the present invention. In some embodiments, the chemical entity is a compound of Formula (I), or a pharmaceutically acceptable salt thereof. In some embodiments, the subject is a human.

In some embodiments, a chemical entity of Formula (I) may be the only active agent administered in methods disclosed herein or may be administered together with an additional active agent.

In some embodiments, chemical entities of the present invention are useful in methods (or in the manufacture of a medicament or composition for use in such methods) of enhancing neuronal plasticity—an essential property of the brain that can be augmented in healthy animals and impaired in numerous CNS disorders. Without being limited by mechanism, such chemical entities may enhance neuronal plasticity by enhancing cyclic adenosine monophosphate (cAMP) response element binding protein (CREB) pathway function in cells, resulting in the modulation of transcription of genes involved in synaptic plasticity. See, e.g., Tully et al., *Nat. Rev. Drug Discov.* 2003, 2, 267-277; Alberini, *Physiol. Rev.* 2009, 89, 121-145. Accordingly, the present invention provides a method of enhancing neuronal plasticity, comprising administering to a subject in need thereof an effective amount of a chemical entity of the present invention. In some embodiments, the chemical entity is a compound of Formula (I), or a pharmaceutically acceptable salt thereof. In preferred embodiments, the subject is a human.

In some embodiments, chemical entities of the present invention are useful in methods (or in the manufacture of a medicament or composition for use in such methods) to augment the efficiency of training protocols, which facilitate functional reorganization in targeted "domains" (or "functions") in the brain. Training protocols can be directed to rehabilitating or enhancing a cognitive or motor function. The training protocol (cognitive or motor training) induces neuronal activity in specific brain regions and produces improved performance of a specific brain (cognitive or motor) function. In such protocols, chemical entities may act as "augmenting agents" to shorten the time that methods of rehabilitating (or enhancing) a cognitive or motor function result in improved performance or a functional gain.

Such augmented training therefore comprises a specific training protocol for a particular brain function, such as that underlying declarative memory, performance of a fine motor skill, a specific locomotor function, language acquisition, executive function, etc., and a general administration of an augmenting agent.

Neurological Disorders

In some embodiments, chemical entities of the present invention are useful in methods (or in the manufacture of a medicament or composition for use in such methods) of treating a neurological disorder, comprising administering to a subject in need thereof an effective amount of a chemical entity or composition of the present disclosure. In some embodiments, the chemical entity is a compound of Formula (I), or a pharmaceutically acceptable salt thereof. In preferred embodiments, the subject is a human.

In some embodiments, the methods are directed to a cognitive deficit ("cognitive impairment") or motor deficit ("motor impairment") associated with (or "due to") the neurological disorder. Accordingly, in some embodiments, the disclosure provides a method for treating a cognitive deficit associated with a neurological disorder, comprising administering to a subject in need thereof an effective amount of a chemical entity of Formula (I).

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

Neurodevelopmental (or "developmental" disorders), such as intellectual disability disorders (e.g., Rubinstein-Taybi syndrome, Down syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, and schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder (MDD), persistent depressive disorder (dysthymia), and other depressive disorders;

Anxiety disorders, such as specific phobia, social anxiety disorder, panic disorder, and generalized anxiety disorder (social phobia);

Obsessive-compulsive and related disorders, such as obsessive-compulsive disorder, body dysmorphic disorder, and other obsessive-compulsive and related disorders;

Dissociative disorders, such as dissociative identity disorder, dissociative amnesia, and other dissociative disorders;

Disruptive, impulse-control, and conduct disorders, such as conduct disorders, antisocial personality disorders, and other disruptive, impulse-control, and conduct disorders;

Trauma- and stressor-related disorders, such as posttraumatic stress disorder (PTSD), acute stress disorder (ASD), adjustment disorders, and other trauma- and stressor-related disorders;

Feeding and eating disorders, such as anorexia nervosa, bulimia nervosa, and binge-eating disorder;

Sleep-wake disorders, such as insomnia, narcolepsy, parasomnias, and other sleep-wake disorders;

Sexual disorders, such as arousal disorders, desire disorders, substance and medication-induced dysfunctions, and other sexual disorders;

Substance-related and addictive disorders, such as those involving alcohol, drugs, stimulants, opioids, tobacco, and non-substance-related disorders; and other substance-related and addictive disorders; and Personality disorders, such as paranoid personality disorders, antisocial and borderline personality disorders, avoidance personality disorders, and other personality disorders.

In particular embodiments, the disorder is schizophrenia.

In other embodiments, the neurological disorder is an acquired disorder, in which the primary clinical feature is impaired cognition. In other words, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

Delirium, such as substance-intoxication (or withdrawal) delirium, medication-induced delirium, and other forms of delirium;

Dementias and other cognitive impairments due to neurodegenerative diseases, such as Alzheimer's disease, Parkinson's disease, Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;

In some embodiments, the disclosure provides a method of treating a neurological disorder, comprising administering to a patient in need thereof an effective amount of a pharmaceutical composition, wherein the neurological disorder is selected from the group consisting of a depressive disorder, a pain disorder, a cognitive disorder, and a neurodegenerative disorder, and a sleep disorder.

Age-associated cognitive deficits, including age-associated memory impairment (AAMI), also referred to as age-related memory impairment (AMI) (See, e.g., Crook et al., *Devel. Neuropsychol.* 1986, 2, 261-276); and deficits affecting patients in early stages of cognitive decline, as in Mild Cognitive Impairment (MCI) (See, e.g., Arnáiz and Almkvist, *Acta Neurol. Scand. Suppl.* 2003, 179, 34-41).

Trauma-dependent losses of cognitive function, such as vascular diseases due to stroke (e.g., ischemic or hemorrhagic stroke) or ischemia; microvascular disease arising from diabetes or arthrosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia, and viral infection (e.g., encephalitis); excitotoxicity; and seizures.

Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

Migraine variants, such as chronic migraine, basilar migraine, vertebrobasilar migraine, status migrainosus, and other forms of migraine;

As used herein, the terms "Neurodevelopment disorders," "Schizophrenia spectrum and other psychotic disorders," "Mood disorders," "Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," Personality disorders," "Delirium," "Neurocognitive disorders," "Delirium," "Dementias," and "Trauma" includes treatment of those mental disorders as described in the Diagnostic and Statistical Manual of Mental Disorders (DSM-5; $5^{th}$ ed., 2013, American Psychiatric Association). The skilled artisan will recognize that there are alternative nomenclatures and classification systems for mental disorders, and that these systems evolve with medical and scientific progress. Thus the terms described in this paragraph are intended to include like disorders that are described in other diagnostic sources.

Depressive Conditions

In some embodiments, chemical entities of the present invention are useful in methods (or in the manufacture of a medicament or composition for use in such methods) of treating a depressive condition (disorder), comprising administering to a subject in need thereof an effective amount of a chemical entity or composition of the present disclosure. In one aspect, the chemical entity is a compound of Formula (I), or a pharmaceutically acceptable salt thereof. For example, anti-depressant-like effects of low ketamine doses are associated with elevated AMPA receptor function, supporting favorable physiochemical properties for HNK in disclosed methods. See, e.g., Tizabi et al., *Neuroscience* 2012, 213, 72-80.

In a specific aspect, the depressive disorder is major depressive disorder (MDD) (also referred to as "major depression" or "clinical depression"). In another aspect, the depressive disorder is persistent depressive disorder (dysthymia). MDD and dysthymia are among the most common depressive disorders. Other depressive disorders that can be treated include, but are not limited to, psychotic depression, postpartum depression, seasonal affective disorder (SAD), a mood disorder; depression due to another medical condition such as cancer, chronic pain, chronic stress, post-traumatic stress disorder, or a bipolar disorder.

A depressive condition is characterized by one or more depressive symptoms. "Depressive symptoms" may include feelings of persistent anxiousness, sadness, helplessness, hopelessness, worthlessness, or pessimism; low energy; low mood; restlessness; irritability; fatigue; loss of interest in pleasurable activities or hobbies; aversion to activity; poor concentration or indecisiveness; excessive guilt; insomnia; excessive sleepiness; overeating; loss of appetite; thoughts of suicide; and suicide attempts.

The presence, severity, frequency, and duration of depressive symptoms vary on a case to case basis. In some embodiments, a patient may have at least one, at least two, at least three, at least four, or at least five of these symptoms. Depressive symptoms may occur in the context of depressive disorders, bipolar disorders, mood disorders due to a general medical condition, substance-induced mood disorders, and other unspecified mood disorders. In addition, depressive symptoms may also be present in association with other psychiatric disorders, including, but not limited to, psychotic disorders, cognitive disorders, eating disorders, anxiety disorders and personality disorders. The longitudinal course of the disorder, the history, and type of symptoms, and etiologic factors help distinguish the various forms of mood disorders from each other.

A "depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, The Quick Inventory of Depressive-Symptomatology Self-Report (QIDS-SR16), the 17-Item Hamilton Rating Scale of Depression (HRSD17), the 30-Item Inventory of Depressive Symptomatology (IDS-C30), or The Montgomery-Asperg Depression Rating Scale (MADRS). Such ratings scales may involve patient self-report or be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale (for instance, less than or equal to 7 on the HRSD17; or less than or equal to 5 on the QIDS-SR16; or less than or equal to 10 on the MADRS). Such a score generally corresponds to minimal symptoms and therefore a clinically desired outcome.

Accordingly, in some embodiments, the disclosure provides a method for treating a symptom of depression, comprising administering to a subject in need thereof a therapeutically effective amount of a chemical entity of Formula (I). In one aspect, the chemical entity is a compound of Formula (I), or a pharmaceutically acceptable salt thereof. In preferred embodiments, the subject is a human. In one aspect, a therapeutically effective amount is an amount effective to achieve remission on a depression symptoms rating scale. In one aspect, the rating scale is HRSD17, QIDS-R16, or MADRS. In another aspect, a therapeutically effective amount is an amount effective to decrease symptoms, wherein a decrease in depressive symptoms is at least a 50% reduction of symptoms identified on a depression symptom rating scale, or a score less than or equal to 7 on the HRSD17, or less than or equal to 5 on the QID-SR16, or less than or equal to 10 on the MADRS.

In some embodiments, the methods of the present disclosure can be used to treat major depressive disorder. Major depressive disorder is typically defined as the presence of one or more major depressive episodes that are not better accounted for by psychotic disorder or bipolar disorder. For major depressive disorder, an essential feature is a period of at least 2 weeks during which there is either depressed mood or the loss of interest or pleasure is nearly all activities, and for persistent depressive disorder, an essential feature is a depressed mood that occurs for most of the day, for more days that not, for at least 2 years, or at least 1 year for children and adolescents. See, American Psychiatry Association Diagnostic and Statistical Manual of Mental Disorders (5th edition).

In connection with treatment, "recovery" means that remission, as defined herein, has sufficiently been sustained, e.g., for 4 months or more, without a "relapse" (such that continued well-being is expected). A relapse means that the patient has experienced a return of the same index major depressive episode (e.g., severe major depression) before reaching achieving the criteria for recovery. A "recurrence" refers to the development of a new major depressive disorder following recovery.

Accordingly, in some embodiments, chemical entities of the present invention are useful in methods (or in the manufacture of a medicament or composition for use in such methods) of treating major depressive disorder, comprising administering to a subject in need thereof a therapeutically effective amount of a chemical entity or composition of the present disclosure. In one aspect, the chemical entity is a compound of Formula (I), or a pharmaceutically acceptable salt thereof. In some embodiments, treatment results in recovery without a relapse. In some embodiments, treatment prevents relapse in subjects who previously achieved symptom remission. In some embodiments, treatment prevents recurrence in subjects who previously attained recovery from an initial major depressive disorder. In some embodiments, treatment prevents recurrence for a period of 6 months, 1 year, 2 years, or longer.

In some embodiments, the methods of the present disclosure can be used to treat treatment resistant (or "treatment refractory") depression. A treatment resistant patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs. A treatment-resistant patient may also be identified as one who is unwilling or unable to tolerate the side effects of one or more standard pharmacological or non-pharmacological treatment.

Accordingly, in certain embodiments, the invention relates to methods for treating treatment-resistant depression by administering to a subject in need thereof an effective amount of a compound of Formula (I) or composition of the present disclosure. In some embodiments, the treatment-resistant depression is unipolar depression, including major depression, including unipolar major depression. In some embodiments, the treatment-resistant depression is bipolar depression, including a major depressive episode associated with a bipolar disorder. In some embodiments, methods of treating depression are contemplated when a patient has suffered depression for e.g., 5, 6, 7, 8 or more weeks, or for a month or more. In a specific aspect, the chemical entity is a compound of Formula (I), or a pharmaceutically acceptable salt thereof.

In some embodiments, the disclosure provides methods of treating suicidal ideation. Suicidal ideations is generally associated with depressive and other mood disorder. In addition, it also can be associated with other mental disorders, life events, and family events, all of which may increase the risk of suicidal ideation. For example, many individuals with borderline personality disorder exhibit recurrent suicidal behavior and suicidal thoughts. Ketamine (and its metabolites) can offer a therapeutic option in patients at imminent risk of suicide. See, e.g., Ballard et al., *J Psych. Res.* 2014, 58, 161-166; Wilkinson and Sanacora, *Depress. Anxiety* 2016, 33, 711-717.

Accordingly, in specific embodiments, the disclosure provides a method of treating suicidal ideation, comprising administering to a subject in need thereof an effective amount of a chemical entity of Formula (I) or composition of the present disclosure. In a specific aspect, the chemical entity is a compound of Formula (I), or a pharmaceutically acceptable salt thereof. In a specific aspect, suicidal ideation is associated with a depressive disorder.

In some embodiments, the present disclosure provides methods for rapidly treating a depressive disorder or condition. Current antidepressants generally take several weeks or more to produce a response. Recent research, however, suggests that a single low-dose of ketamine can act as a novel, rapid-acting antidepressant with minimal side effects. Naughton et al., *J. Affect. Dis* 2014, 156, 24-35; Muller et al., *Ther. Adv. Psychopharmacol.* 2016, 6, 185-192. Moreover, recent work indicates that the metabolism of (R,S)-ketamine to HNK is essential for its antidepressant effects, and that the (2R,6R)-HNK enantiomer exerts behavioral, electroencephalographic, electrophysiological and cellular antidepressant-related actions in mice. Zanos et al., *Nature* 2016, 533, 481-486. These results underscore favorable physiochemical properties for HNK that are pertinent in the development of rapid acting agents in depression—with particular importance to treatment-resistant depressive disorders and depressive disorders with suicidal ideation. See, e.g., DiazGranados et al., *J Clin Psychiatry* 2010, 71, 1605-1611; Cusin et al., *Am. J. Psych.* 2012, 169, 868-869; Larkin et al., *Int. J Neuropsych.* 14, 1127-1131; Abdallah et al., *Depress. Anxiety* 2016, 33, 689-697.

Obsessive Compulsive Disorders

In some embodiments, the disclosure provides methods of treating an obsessive-compulsive disorder (OCD). Without being limited by mechanisms, several lines of neurochemical and genetic evidence suggest that glutamate dysregulation may contribute to obsessive-compulsive disorder (OCD) and that targeting glutamate may be beneficial in treating refractory disease. Kariuki-Nyuthe et al., *Curr. Opin. Psych.* 2014, 27, 32-37; Rodriguez et al., *Neuropsychopharmacology.* 2013, 38, 2475-2483; Pittenger, *Psychiatr. Ann.* 2015, 45, 308-315. OCD may there therefore be amenable to treatment by modulators of glutamate signaling, which can include chemical entities of the present disclosure.

Accordingly, in certain embodiments, the disclosure provides methods for treating OCD, comprising administering to a subject in need thereof an effective amount of a chemical entity of Formula (I) or composition of the present disclosure. In a specific aspect, the chemical entity is a compound of Formula (I), or a pharmaceutically acceptable salt thereof.

Anxiety

In some embodiments, the disclosure provides methods of treating an anxiety disorder, comprising administering to a subject in need thereof an effective amount of a chemical entity of Formula (I) or composition of the present disclosure. In a specific aspect, the chemical entity is a compound of Formula (I), or a pharmaceutically acceptable salt thereof.

In a specific embodiment, chemical entities, including compounds, of the present disclosure are used as anti-anxiety (anxiolytic) agents to treat an anxiety disorder.

Bipolar Disorders

In some embodiments, the disclosure provides methods of treating a bipolar disorder, comprising administering to a subject in need thereof an effective amount of a chemical entity of Formula (I) or composition of the present disclosure. In a specific aspect, the chemical entity is a compound of Formula (I), or a pharmaceutically acceptable salt thereof.

In a specific embodiment, the bipolar disorder is bipolar I disorder, bipolar II disorder, cyclothymic disorder, or other bipolar and related disorders.

Trauma- and Stressor-Related Disorders

In some embodiments, the disclosure provides methods of treating trauma- and stressor-related disorders, comprising administering to a subject in need thereof an effective amount of a chemical entity of Formula (I) or composition of the present disclosure. In a specific aspect, the chemical entity is a compound of Formula (I), or a pharmaceutically acceptable salt thereof. Trauma- and stressor-related disorders involve exposure to a traumatic or stressful event. See, e.g., Zhang et al., *Psychopharmacology* 2015, 232, 663-672. In one embodiment, the disorder is post-traumatic stress disorder (PTSD), including chronic PTSD. See, e.g., Feder et al., *JAMA Psychiatry* 2014, 71, 681-688. In another embodiment, the disorder is acute stress disorder (ASD).

In some embodiments, the disclosure provides methods of treating pain. For example, sub-anesthetic does of (R,S)-ketamine have demonstrated efficacy in treating neuropathic and chronic pain, including the treatment of patients suffering from complex regional pain syndrome (CRPS). Goldberg et al., *Pain Physician* 2010, 13, 379-387. Moreover, analysis of plasma samples obtained from CRPS patients receiving (R,S)-ketamine as a 5-day continuous infusion reveals that the primary drug, (R,S)-ketamine, is not primarily responsible for the therapeutic response and instead that the active agents responsible for the therapeutic response may include HNK metabolites. Moaddel et al., *Talanta* 2010, 15, 1892-1904. More generally, ketamine may be useful as an effective analgesic in treating postoperative pain, chronic pain, intractable cancer pain, uncontrolled severe pain, acute and subacute pain in opioid-tolerant patients, and pain in palliative care patients. See, e.g., Hirota and Lambert, *Br. J. Anaesth.* 2001, 107, 123-126; Lossignol et al., *Support Care Cancer* 2005, 13, 188-93; Chazan et al., *J Opioid Manag.* 2008, 4, 173-180; Carstensen and Møllerand, *Br. J. Anaesth.* 2010, 104, 410-406; Beaudoin et al., *Acad. Emerg. Med.* 2014, 11, 1193-1202.

Accordingly, in certain embodiments, the disclosure provides methods for treating pain, comprising administering to a subject in need thereof an effective amount of a chemical entity of Formula (I). In a specific aspect, the chemical entity is a compound of Formula (I), or a pharmaceutically acceptable salt thereof.

In some embodiments, an effective amount is an amount effective to decrease painful symptoms, wherein a decrease in painful symptom is at least a 50% reduction of painful symptoms on a pain rating scale.

In some embodiments, pain is associated with a neurological disorder. In particular embodiments, pain is associated with complex regional pain syndrome (CRPS). In some embodiments, pain is associated with chronic fatigue syndrome or fibromyalgia, and may include muscle pain, myofascial pain, temporal summation, and referred pain. See, e.g., Graven-Nielsen et al., *Pain.* 2000, 85, 483-491; Bennett, *Curr. Opin. Rheumatol.* 1998, 10, 95-103.

In some embodiments, the pain is chronic pain, acute pain, subacute pain, neuropathic pain, post-operative pain, cancer pain, inflammatory pain, visceral pain, migraine pain, headache, and menstrual pain. In a specific embodiment, the pain is migraine pain. See, e.g., Kaube et al., *Neurology* 2000, 55, 139-141. In a specific embodiment, the pain is a headache, including a cluster headache. See, e.g., Krusz et al., *J. Pain* 2010, 11, S43; Granata et al., *Schmerz* 2016, 30, 286-288. In a specific embodiment, the pain is menstrual pain. See, e.g., U.S. Patent Appl. No. 2015-0313892; Udoji and Ness, *Pain Manag.* 2013, 3, 387-394.

Other Indications

Studies have reported that glutamate receptor subunits are expressed in cells found in many different tumors and cancers, such as glioma, colorectal and gastric cancer, oral squamous cell carcinoma, prostate cancer, melanoma, and osteosarcoma. See, e.g., Stepulak et al., *Histochem. Cell Biol.* 2009, 132, 435-445. Accordingly, in certain embodiments, the disclosure provides methods for treating cancer, comprising administering to a subject in need thereof an effective amount of a chemical entity of Formula (I). In a specific aspect, the chemical entity is a compound of Formula (I), or a pharmaceutically acceptable salt thereof.

Several studies indicate that ketamine action is associated with anti-inflammatory effects in vivo and in some clinical settings. See, e.g., Roytblat et al., *Anesth. Analg.* 1998, 87, 266-271; Mazar et al., *Anesthesiology.* 2005, 102, 1174-1181; Suliburk et al., *Surgery* 2005, 138, 134-140; De Kock et al., *CNS Neurosci. Ther.* 2013, 19, 403-410. Accordingly, in certain embodiments, the disclosure provides methods for treating various inflammatory conditions, such as autoimmune, acquired immune, or drug-induced immune conditions, or inflammation caused by another condition, comprising administering to a subject in need thereof an effective amount of a chemical entity of Formula (I). In a specific aspect, the chemical entity is a compound of Formula (I), or a pharmaceutically acceptable salt thereof.

Studies suggest that intermittent ketamine infusions can suppress compulsive behavior in eating disorders. See, e.g., Mills et al., *QJM* 1998, 91, 493-503. Accordingly, in certain embodiments, the disclosure provides methods for treating an eating disorder, comprising administering to a subject in need thereof a therapeutically effective amount of a chemical entity of Formula (I). In a specific aspect, the chemical entity is a compound of Formula (I), or a pharmaceutically acceptable salt thereof.

In some embodiment, the present disclosure provides a method of treating a seizure. See, e.g., Sheth et al., *Neurology* 1998, 51, 1765-1766. Accordingly, in certain embodiments, the disclosure provides methods for treating a seizure, comprising administering to a subject in need thereof a therapeutically effective amount of a chemical entity of Formula (I). In a specific aspect, the chemical entity is a compound of Formula (I), or a pharmaceutically acceptable salt thereof.

Cognitive Enhancement and Performance

Chemical entities of Formula (I) are also useful in enhancing learning and memory, as well as other cognitive functions that involve glutamatergic signaling, including attention and alertness. For example, AMPA Receptor trafficking underlies numerous experience-driven phenomena that range from forming neuronal circuits to modifying behavior. See, e.g., Kessels and Malinow, *Neuron* 2009, 12, 340-350; Anggono and Hugnair, *Curr. Opin. Neurobiol.* 2012, 22, 461-469; Henley and Wilkinson, *Dialogs in Clinical Neuroscience* 2013, 15, 11-27.

In addition, AMPA Receptor modulation has been implicated in human cognitive performance, alertness, and recovery sleep. Boyle et al., *J. Psychopharm.* 2012, 26, 1047-1057; Partin, *Curr. Opin. Pharmacol.* 2015, 20, 46-53; Hagewoud et al., *J. Sleep. Res.* 2010, 19, 280-288. Accordingly, in some embodiments, the disclosure provides methods of enhancing memory and cognition, as well as treating memory and other cognitive deficits associated with normal aging and age-related neurological disorders, comprising administering to a subject in need thereof an effective amount of a chemical entity of Formula (I). In a specific aspect, the chemical entity is a compound of Formula (I), or a pharmaceutically acceptable salt thereof.

In other embodiments, the disclosure provides a method of modulating sleep, comprising administering to a subject in need thereof an effective amount of a chemical entity of Formula (I). In some embodiments, the method of modulating sleep is promoting sleep recovery after sleep deprivation. In a specific aspect, the chemical entity is a compound of Formula (I), or a pharmaceutically acceptable salt thereof.

In some embodiments, chemical entities of the present invention are useful in methods (or in the manufacture of a medicament or composition for use in such methods) of enhancing the efficacy of cognitive behavioral therapy (CBT) for a neurological disorder. CBT is a psychosocial intervention that is a widely used for treating mental disorders. See, e.g., Hofmann et al., *J. Cognit. Ther. Res.* 2012, 36, 427-440. CBT focuses on the development of personal coping strategies that target solving current problems and changing unhelpful patterns in cognitions (e.g., thoughts, beliefs, and attitudes), behaviors, and emotional regulation. Although originally designed to treat depression, CBT can be used for a number of neurological disorders, including obsessive compulsive disorder, generalized anxiety disorder, and trauma- and stressor-related disorders, such as PTSD.

In some embodiments, chemical entities of the present invention are useful in methods (or in the manufacture of a medicament or composition for use in such methods) of enhancing the efficacy of dialectical behavior therapy (DBT) for a neurological disorder. DBT is a specific type of cognitive-behavioral psychotherapy designed to help people change patterns of behavior that are not helpful, such as self-harm, suicidal thinking, and substance abuse. Since its development, it has also been used for the treatment of other kinds of mental health disorders.

Accordingly, in some embodiments, the present disclosure provides a method of administering to a subject undergoing CBT or DBT for a neurological disorder a therapeutically effective amount of a chemical entity of Formula (I). In a specific aspect, the chemical entity is a compound of Formula (I), or a pharmaceutically acceptable salt thereof. In a specific aspect, the neurological disorder is depression. In another aspect, the neurological disorder is obsessive compulsive disorder. In another aspect, the neurological disorder is generalized anxiety disorder. In another aspect, the neurological disorder is selected from trauma- and stressor disorders, such as PTSD.

Treatment Combinations

In some embodiments, a compound of Formula (I) is administered with another active agent to treat an indication disclosed herein. In specific embodiments, the combination is administered to treat depression, schizophrenia, Alzheimer's disease, migraine variants with or without pain, Lou Gehrig's disease (also called amyotrophic lateral sclerosis or ALS), or pain. Such administration may be simultaneously or sequentially.

Exemplary agents for treating depression include selective serotonin reuptake inhibitors (SSRIs), such as sertraline, fluoxetine, citalopram, escitalopram, paroxetine, fluvoxamine. and trazodone; serotonin and norepinephrine reuptake inhibitors (SNRIs), such as desvenlafaxine, duloxetine, levomilnacipran, and venlafaxine; tricyclic antidepressants (TCAs), such as amitriptyline, amoxapine, clomipramine, desipramine, doxepin, imipramine, nortriptyline, protriptyline, and trimipramine; monoamine oxidase inhibitors (MAOIs), such as isocarboxazid, phenelzine, selegiline, and tranylcypromine; and other classes of drugs, such as maprotiline, bupropion, vilazodone, nefazodone, trazodone, vortioxetine, and mirtazapine.

Exemplary agents for treating schizophrenia include: clozapine, aripiprazole, brexpiprazole, cariprazine, lurasidone, paliperidone, quetiapine, risperidone, olanzapine, ziprasidone, and iloperidone.

Exemplary agents for treating Alzheimer's Dementia include, but are not limited to, donepezil, rivastigmine, galantamine, marijuana-like cannabinoids, and memantine.

Exemplary agents for treating Migraines include, but are not limited to, caffeine; acetaminophen; nonsteroidal anti-inflammatory drugs (NSAIDs), such as aspirin, ibuprofen, naproxen, ketoprofen, tolmetin, etodolac, nabumetone, piroxicam, and droxican; cyclo-oxygenease-2 (Cox-2) inhibitors such as celcoxib; topiramate; amitriptyline; sumatriptan; frovatriptan; rizatriptan; naratriptan; almotriptan; eletriptan; botulinum toxin; narcotic pain medications such as codeine, fentanyl, hydrocodone, hydromorphone, meperidine, methadone, morphine, and oxycodone; centrally acting analgesics, such as tramadol; and other classes of drugs, such as certain anticonvulsants, antidepressants, psychostimulants, marijuana-like cannabinoids, and corticosteroids.

Exemplary agents for treating ALS include riluzole.

Exemplary agents for treating pain include, but are not limited to, acetaminophen; nonsteroidal anti-inflammatory drugs (NSAIDs), such as aspirin, ibuprofen, naproxen, ketoprofen, tolmetin, etodolac, nabumetone, piroxicam, and droxican; cyclo-oxygenease-2 (Cox-2) inhibitors such as celcoxib; narcotic pain medications such as codeine, fentanyl, hydrocodone, hydromorphone, meperidine, methadone, morphine, and oxycodone; centrally acting analgesics, such as tramadol; and other classes of drugs, such as certain anticonvulsants, antidepressants, psychostimulants, marijuana-like cannabinoids, and corticosteroids.

The preceding list of additional active agents is meant to be exemplary rather than fully inclusive. Additional active agents not included in the above list may be administered in combination with a compound of Formula (I). The additional active agent will be dosed according to its approved prescribing information, though in some embodiments the additional active agent will be dosed at less the typically prescribed dose and in some instances less than the minimum approved dose.

EXAMPLES

The present disclosure is further illustrated by the following non-limiting Examples. These Examples are understood to be exemplary only, and they are not to be construed as limiting the scope of the present disclosure.

Exemplary compounds can be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −100° C. and the reflux temperature of the solvent. Reactions may be heated employing conventional heating or microwave heating. Reactions may also be conducted in sealed pressure vessels above the normal reflux temperature of the solvent.

Synthetic Schemes

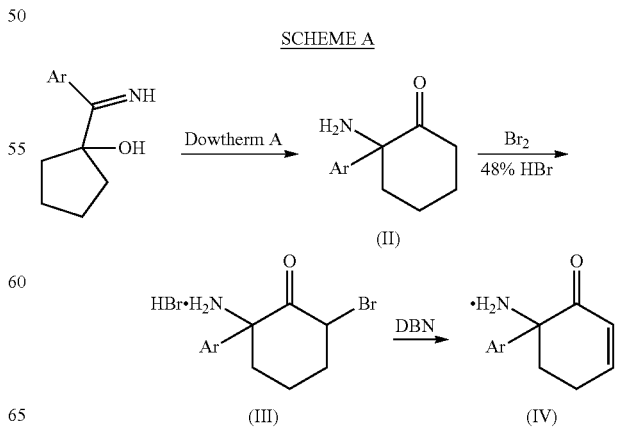

SCHEME A

In accordance with Scheme A, hydroxylimine compounds can undergo a thermal rearrangement to give 2-aminocyclohexanones when heated in the presence of a heat transfer fluid such as Dowtherm-A at temperatures ranging from 100 to 240° C.

Subsequent halogenation, under conditions known to one skilled in the art, provides the haloketone. For example, treatment of compounds of formula (II) with bromine in 48% hydrobromic acid at temperatures ranging from 40 to 100° C. affords bromoketones of formula (III) as the hydrobromide salt.

Subsequent dehalogenation under basic conditions known to one skilled in the art affords the enone. For example, treatment of compounds of formula (III) in the presence of a base such as DBN, DBU and the like, in a solvent such as ACN, at reflux, affords compounds of formula (IV).

like, in a solvent, such as THF, and at temperatures between −78° C. and 22° C. affords the corresponding trimethylsilyl enol ether.

Oxidation with an oxidizing agent, such as mCPBA, in the presence of a base, such as $Na_2CO_3$, and a solvent, such as hexanes, at room temperature affords the hydroxyketone of formula (VII).

Subsequent treatment with BSTFA in the presence of a base, such as pyridine or the like, in a solvent, such as DCM, chloroform or the like, at temperatures ranging from 30 to 80° C. affords the trimethylsilyl ether.

Deprotection of the carbamate protecting group and of the trimethylsilyl ether affords compounds of formula (IX). For example, treatment of trimethylsilyl ether (VIII) with TMSI in a solvent, such as DCM, chloroform or the like, and methanol at room temperature affords the amino alcohol of formula (IX).

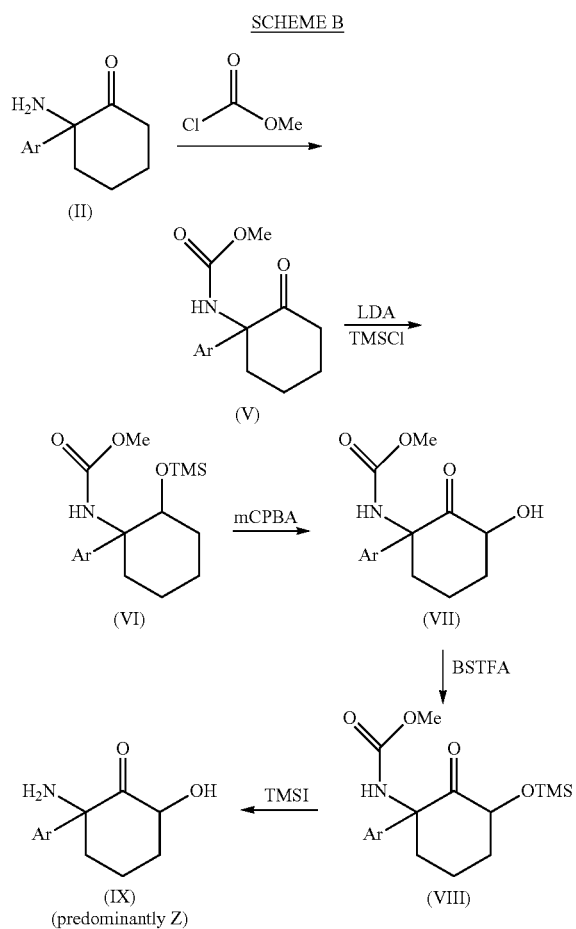

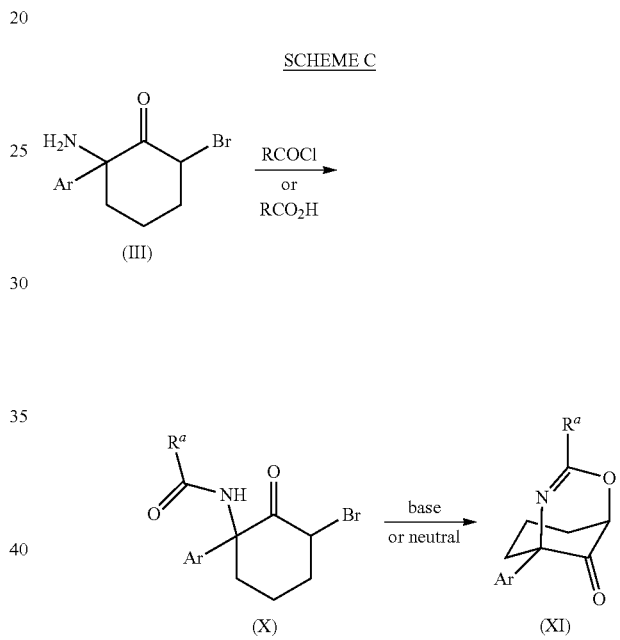

In accordance with Scheme B, compounds of formula (IX) can be synthesized in five steps from a compound of formula (II):

Treatment of compounds of formula (II) with an alkyl chloroformate, under basic conditions known to one skilled in the art, provides compounds of formula (V). For instance, treatment of the 2-aminocyclohexanone of formula (II) with methyl chloroformate in the presence of a base, such as $Na_2CO_3$ or the like, in a solvent such a benzene, toluene, or the like, at temperatures ranging from 65-110° C., affords the methyl carbamate of formula (V).

Subsequent treatment with a base, such as LDA or the like, followed by a silylating agent such as TMSCl, or the In accordance with Scheme C, imidates of Formula (XI) can be synthesized in two steps from a 2-amino-6-bromocyclohexanone of formula (III):

Treatment of compounds of formula (III) with an acid chloride in the presence of a base, under conditions known to one skilled in the art, provides compounds of formula (X). Alternatively, treatment of the 2-amino-6-bromocyclohexanone with a carboxylic acid and a coupling reagent, in the presence of a base, under conditions known to one skilled in the art, also provides the amide of formula (X). For example, treatment of compounds of formula (III) with an acid chloride, in the presence of a base, such as TEA or the like, in a solvent such as chloroform, DCM or the like affords an amide of formula (X).

Subsequent treatment with a base, such as NaH or the like, in a solvent such as DMF, DMA or the like, affords an imidate of formula (XI), wherein, $R^a$=—H, —$C_{1-6}$alkyl, —$C_{1-6}$haloalkyl, —$C_{3-8}$alkenyl, —$C_{3-8}$alkynyl, —$(CH_2)_n$aryl, —$(CH_2)_n$heteroaryl, —$(CH_2)_n$cycloalkyl, —$(CH_2)_n$heterocycloalkyl, —$COR^2$, —$CONR^3R^4$, —$CR^5R^6NR^7R^8$, —$CHR^9R^{10}$, or —$C(OH)R^{11}R^{12}$.

SCHEME D

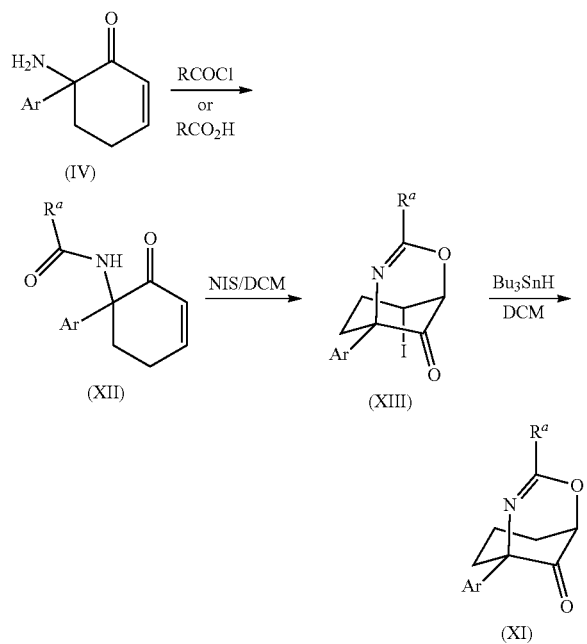

In accordance with Scheme D, imidates of Formula (XI) can be synthesized in three steps from a 6-aminocyclohex-2-enone of Formula (IV):

Treatment of compounds of formula (IV) with an acid chloride in the presence of a base, under conditions known to one skilled in the art, provides the amide of Formula (XII). Alternatively, treatment of the 6-aminocyclohex-2-enone with a carboxylic acid and a coupling reagent, in the presence of a base, under conditions known to one skilled in the art, also provides the amide of Formula (XII). For example, treatment of compounds of formula (IV) with an acid chloride, in the presence of a base, such as TEA or the like, in a solvent such as chloroform, DCM or the like, affords an amide of formula (XII).

Subsequent treatment with a halogenation reagent, such as NIS or the like, in the presence of a base, such as Et₃N or the like, in a solvent, such as DCM or chloroform, affords the iodinated imidate of formula (XIII).

Subsequent treatment with Bu₃SnH in a solvent, such as DCM or the like, at temperatures ranging from 20 to 60° C. provides an imidate of formula (XI), wherein, $R^a$=—H, —$C_{1-6}$alkyl, —$C_{1-6}$haloalkyl, —$C_{3-8}$alkenyl, —$C_{3-8}$alkynyl, —$(CH_2)_n$aryl, —$(CH_2)_n$heteroaryl, —$(CH_2)_n$cycloalkyl, —$(CH_2)_n$heterocycloalkyl, —$COR^2$, —$CONR^3R^4$, —$CR^5R^6NR^7R^8$, —$CHR^9R^{10}$, or —$C(OH)R^{11}R^{12}$.

SCHEME E

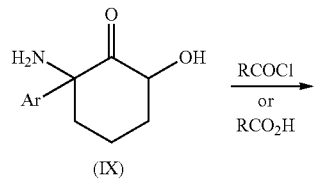

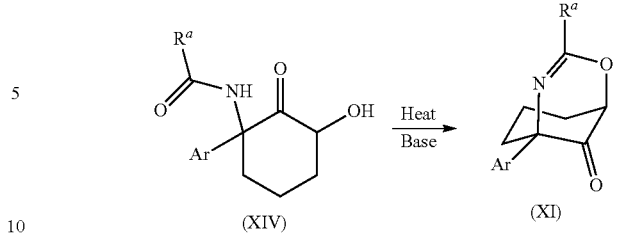

In accordance with Scheme E, imidates of Formula (XI) can be synthesized in two steps from a 2-amino-6-hydroxy-cyclohexanone of Formula (IX).

Treatment of compounds of formula (IX) with an acid chloride in the presence of a base, under conditions known to one skilled in the art, provides the amide of Formula (XIV). Alternatively, treatment of the 2-amino-6-hydroxy-cyclohexanone derivative with a carboxylic acid and a coupling reagent, in the presence of a base, under conditions known to one skilled in the art, also provides the amide of Formula (IX). For example, treatment of the 2-amino-6-hydroxy-2-(2-chlorophenyl)cyclohexanone of Formula (IX) with an acid chloride, in the presence of a base, such as TEA or the like, in a solvent such as chloroform, DCM or the like affords an amide of formula (XIV).

Subsequent treatment with ethylene glycol in the presence of a base, such as NaOH or the like, at temperatures ranging from 150-220° C. provides an imidate of formula (XI), wherein, $R^a$=—H, —$C_{1-6}$alkyl, —$C_{1-6}$haloalkyl, —$C_{3-8}$alkenyl, —$C_{3-8}$alkynyl, —$(CH_2)_n$aryl, —$(CH_2)_n$heteroaryl, —$(CH_2)_n$cycloalkyl, —$(CH_2)_n$heterocycloalkyl, —$COR^2$, —$CONR^3R^4$, —$CR^5R^6NR^7R^8$, —$CHR^9R^{10}$, or —$C(OH)R^{11}R^{12}$. Alternatively, heating intermediates of formula (XIV) at a temperature ranging between 180-250° C. and a pressure less than 0.5 mmHg for a period of 1-5 h, followed by cooling to room temperature then treatment with a solution of tetraethylammonium hydroxide in a solvent, such as DCM or the like, then subsequent removal of solvent and heating again at reduced pressure as previously described, affords imidate compounds of formula (XI).

SCHEME F

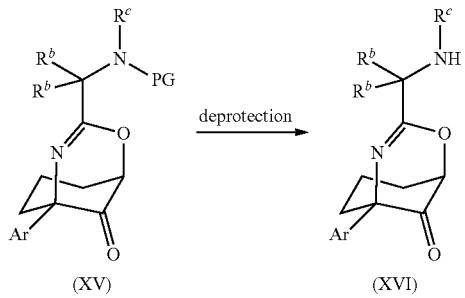

In accordance with Scheme E, deprotection of a nitrogen protecting group is performed under the appropriate conditions known to one skilled in the art, depending on which protecting group is used. In one instance, deprotection of carbamate intermediates of formula (XV), wherein the carbamate protecting group is 9-fluorenylmethyl carbamate (Fmoc), 2-trimethylsilylethyl carbamate (TeOC), t-butyl carbamate (Boc), allyl carbamate (Alloc), benzyl carbamate (Cbz) or the like, can be achieved under conditions known to one skilled in the art. For example, FMC deprotection with piperidine provides a compounds of formula (XVI), wherein each $R^b$ independently =—H, -halo, —$NH_2$, —$C_{1-8}$ alkyl, —$C_{1-8}$haloalkyl, —$(CH_2)_n$ $CONH_2$, —$(CH_2)_n$ COOH, —$(CH_2)_n$aryl, —$(CH_2)_n$heteroaryl, —$(CH_2)_n$cycloalkyl, and —$(CH_2)_n$heterocycloalkyl, each optionally substituted, wherein n is independently an integer selected from 0, 1, 2, 3, and 4; and $R^c$=—H, —$C_{1-4}$alkyl, and —$C_{1-4}$haloalkyl. Alternatively, deprotection of sulfonamide intermediates of formula (XV), wherein the sulfonamide protecting group is p-toluenesulfonyl (Ts), trifluoromethanesulfonyl, trimethylsilylethanesulfonamide (SES), tert-butylsulfonyl (Bus) or the like, can be achieved under conditions known to one skilled in the art. For example, treatment of a Ts protected compound of formula (XV) with a strong acid, such as HBr or the like, in a solvent, such as acetic acid or the like, provides a compound of formula (XVI), wherein $R^b$ and $R^c$ are described above.

Chemistry:

In some embodiments, the following experimental and analytical protocols, unless otherwise indicated, can be used to obtain the resulting compounds.

Unless otherwise stated, reaction mixtures are magnetically stirred at room temperature (rt) under an atmosphere of nitrogen. Where solutions are "dried," they are generally dried over a drying agent such as $Na_2SO_4$ or $MgSO_4$. Where mixtures, solutions, and extracts are "concentrated," they are typically concentrated on a rotary evaporator under reduced pressure.

Reactions under microwave irradiation conditions are carried out in a CEM Discover-SP with Activent microwave reaction apparatus, model number 909150, or Biotage Initiator, model number 355302.

Normal-phase flash column chromatography (FCC) is performed on Silica ($SiO_2$) using packed or prepackaged cartridges, eluting with the indicated solvents.

Analytical LC/MS is obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors. Alternatively, LC-MS is performed on a Waters Acquity UPLC-MS instrument equipped with a Acquity UPLC BEH $C_{18}$ column (1.7 μm, 2.1×50 mm) and the solvent system A: 0.1% HCOOH in $H_2O$ and B: 0.1% HCOOH in ACN. Column temperature is 45° C.

Analytical SFC-MS is performed on a Waters $UPC^2$-MS instrument equipped with a Acquity $UPC^2$BEH 2-ethylpyridine column (1.7 μm, 2.1×50 mm) and the solvent system A: $CO_2$ and B: 0.1% $NH_4OH$ in MeOH. Column temperature is 55° C. All compounds are run using the same elution gradient, i.e., 3% to 35% solvent B in 0.75 min with a flow rate of 2.5 mL/min.

Preparative HPLC is performed on a Shimadzu SIL-10AP system using a Waters SunFire™ OBD 30 mm×100 mm×2.5 μm (particle size) $C^{18}$ column with a 15-minute gradient of 10-100% acetonitrile in water and 0.05% trifluoroacetic acid added as a modifier to both phases. Elution profiles are monitored by UV at 254 and 220 nm. Alternatively, preparative HPLC is performed on a Waters Fractionlynx system equipped with a)(Bridge Prep $C_{18}$ OBD column (5 μm, 19×50 mm) and the solvent system: $H_2O$:ACN and 2% TFA in $H_2O$. Specific elution gradients are based on retention times obtained with an analytical UPLC-MS, however, in general all elution gradients of $H_2O$ and ACN are run over a 5.9 min run time with a flow rate of 40 mL/min. An autoblend method is used to ensure a concentration of 0.1% TFA throughout each run.

Preparative SFC-MS is run on a Waters Prep100 SFC-MS system equipped with a Viridis 2-ethylpyridine OBD column (5 μm, 30×100 mm) and the solvent system: $CO_2$: MeOH and 1% $NH_4OH$ in MeOH. Specific elution gradients are based on retention times obtained with an analytical $UPC^2$-MS; however, in general all elution gradients of $CO_2$ and MeOH are run over a 3.6 min run time with a flow rate of 100 mL/min and a column temperature of 55° C. An autoblend method is used to ensure a concentration of 0.2% $NH_4OH$ throughout each run.

Nuclear magnetic resonance (NMR) spectra can be obtained in a Varian 400 MHz or Bruker 400 MHz NMR.

Chemical names can be generated using ChemBioDraw Ultra 12.0 (CambridgeSoft Corp., Cambridge, Mass.) or ChemAxon (Budapest, Hungary).

Intermediate 1.
2-amino-6-bromo-2-(2-chlorophenyl)cyclohexanone hydrobromide

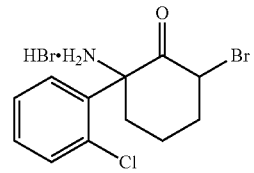

This compound may be prepared in the manner described in *J. Org. Chem.*, 1981, 46, 5055-5060, for example, in accordance with the following:

Step 1. 2-Amino-2-(2-chlorophenyl)cyclohexanone. A solution of 655 g (2.93 mol) of 1-((2-chlorophenyl)(imino) methyl)cyclopentanol in 750 mL of i-PrOH is saturated with anhydrous HCl and then diluted to 1.5 L with anhydrous $Et_2O$. The crystals that form are removed by filtration and dried to give 1-((2-chlorophenyl)(imino)methyl)cyclopentanol as the hydrochloride salt. To 3 L of Dowtherm-A at 200° C. is added 379 g (1.46 mol) of 1-((2-chlorophenyl)(imino) methyl)cyclopentanol (hydrochloride salt) which causes the temperature to fall to 180° C., where it is maintained for 7 min. The reaction mixture is cooled to 10° C., and the solid is removed by filtration and dissolved in $H_2O$. The filtrate is diluted to 3 L with $Et_2O$ and extracted with $H_2O$. The combined aqueous fractions are washed with $Et_2O$, made basic with 50% aqueous NaOH, and extracted with $Et_2O$. The ether layer is washed with water, dried, de-colorized with charcoal, filtered through Celite, and concentrated. The residue is distilled to give the title compound.

Step 2: 2-Bromo-6-amino-6-(2-chlorophenyl)cyclohexanone Hydrobromide. A solution of 298 g (1.33 mol) of 2-Amino-2-(2-chlorophenyl)cyclohexanone in 1.2 L of 48% aqueous HBr is heated to 70° C., and 216 g (1.35 mol) of bromine is added dropwise. The mixture is stirred for 10 min after the addition is complete and cooled to 5° C. The crystals are removed by filtration, washed copiously with acetone, and dried to give 408 g of the title compound, mp 142-145° C. A second crop (30 g, mp 142-145° C.) is obtained by decolorizing and concentrating the acetone washes. An NMR is run in $D_2O$ and shows the presence of excess protons in the HOD peak. The entire yield of 441 g is azeotroped in 500 mL of xylene, with the recovery being 420 g (82%; mp 209-210° C.) and the water collected in a Dean-Stark trap corresponding to a monohydrate.

Intermediate 2.
1-amino-2'-chloro-5,6-dihydro-2(1H)-one hydrobromide

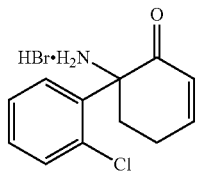

This compound may be prepared in the manner described in *J. Org. Chem.*, 1981, 46, 5055-5060, for example, in accordance with the following:

6-Amino-6-(2-chlorophenyl)-2-cyclohexen-1-one. A solution of 35 g (0.28 mol) of 1,5-diazabicyclo[3.3.1]non-5-ene, 200 mL of acetonitrile, and 74 g (0.25 mol) of 2-Bromo-6-amino-6-(2-chlorophenyl)cyclohexanone (free base) is refluxed for 20 h. The solvent is evaporated and the residue diluted with ether and 5% aqueous NaOH. The layers are separated, and the organic layer is extracted with 5% aqueous HCl. The combined acid-water layers are decolorized with charcoal, filtered through Celite, and made basic with 50% aqueous NaOH. The crystalline precipitate is removed by filtration, is washed with water, and is dried to give 31 g (57%) of the title compound, mp 120-123° C.

Intermediate 3.
2-amino-2-(2-chlorophenyl)-6-hydroxycyclohexanone

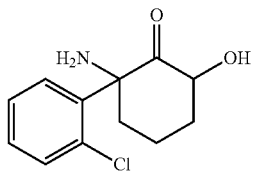 [SMILES: NC1(c2ccccc2Cl)CCCC(O)C1=O]

This compound may be prepared in the manner described in *J. Med. Chem.*, 1986, 29, 2396-2399, for example, in accordance with the follows:

Step 1. 2-(o-Chlorophenyl)-2-[(methoxycarbonyl)-aminocyclohexanone. To a mixture of 2-amino-2-(2-chlorophenyl)cyclohexanone (3.0 g, 14 mmol) in anhydrous benzene (100 mL) and $Na_2CO_3$ (4.5 g) is added a solution of methyl chloroformate (3.0 mL, 40 mmol) in anhydrous benzene (10 mL). After heating under reflux for 3 h, the reaction mixture is cooled to room temperature and washed in turn with $H_2O$, 10% $Na_2CO_3$, and $H_2O$ again. The product is diluted with either, dried ($MgSO_4$), and concentrated under reduced pressure, wherein the title compound precipitates as a white solid.

Step 2. 2-(o-Chlorophenyl)-2-[(methoxycarbonyl)amino]-6-hydroxycyclohexanone. To a cooled (0° C.) mixture of diisopropylamine (4 mL, 28 mmol) and dry THF (30 mL) is added a solution of n-butyllithium in hexane (1.6 M, 17 mL, 28 mmol). The reaction mixture is stirred at 0° C. for 1 h, cooled to −78° C., and treated dropwise with a solution of 2-(o-Chlorophenyl)-2-[(methoxycarbonyl)-aminocyclohexanone (3.2 g, 11 mmol) in dry THF (20 mL). After stirring for a period of 2 h, $Me_3SiCl$ (4 mL, 28 mmol) is added, and the reaction mixture is stirred for 20 min before warming to room temperature over 45 min. Hexane is then added, and the resulting solution is washed with 10% $NaHCO_3$ and $H_2O$ and dried ($MgSO_4$), and the solvent is removed in vacuo to afford the crude product as a yellow oil. Purification by column chromatography on silica gel (75 g, 70-325 mesh, EtOAc as eluent) gives methyl (2'-chloro-6-((trimethylsilyl)oxy)-1,2,3,4-tetrahydro-[1,1'-biphenyl]-1-yl)carbamate as a clear yellow oil, yield 4.5 g (100%). To a mixture of methyl (2'-chloro-6-((trimethylsilyl)oxy)-1,2,3,4-tetrahydro-[1,1'-biphenyl]-1-yl)carbamate (4.46 g, 12.6 mmol) in hexane (60 mL) and $Na_2CO_3$ (2.5 g) is added mCPBA (4.5 g, 20.8 mmol). The reaction mixture is stirred at room temperature for 3 h, and the product is washed (10% $Na_2SO_3$, then $H_2O$), dried ($MgSO_4$), and evaporated to give a white solid. Column chromatography on silica gel (75 g, 70-325 mesh, 5% $CH_3CN$ in $CH_2Cl_2$ as eluent) gives the title compound as an oil.

Step 3. 2-(o-Chlorophenyl)-2-amino-6-hydroxycyclohexanone (6-Hydroxynorketamine). To a solution of 2-(o-Chlorophenyl)-2-[(methoxycarbonyl)amino]-6-hydroxycyclohexanone (3.5 g, 12 mmol) in anhydrous $CH_2Cl_2$ (80 mL) is added BSTFA (4 mL, 15 mmol) and dry pyridine (0.2 mL). The mixture is heated under reflux for 1 h, and excess reagents are removed in vacuo to give methyl (1-(2-chlorophenyl)-2-oxo-3-((trimethylsilyl)oxy)cyclohexyl)carbamate as a white solid: A solution of methyl (1-(2-chlorophenyl)-2-oxo-3-((trimethylsilyl)oxy)cyclohexyl)carbamate (4.5 g, 12 mmol) in dry $CH_2Cl_2$ (80 mL) is treated dropwise with $Me_3SiI$ (3 mL, 17 mmol), and the resulting mixture is stirred at room temperature for 30 min. Methanol (80 mL) is then added, the mixture is washed (10% $Na_2SO_3$, then $H_2O$) and dried ($Na_2SO_4$), and the solvent is evaporated to give the crude product as a yellow oil (1.0 g). Column chromatography on silica gel (10 g, 70-325 mesh, EtOAc as eluent) gives the title compounds as a pure oil.

Intermediate 4. N-(3-bromo-1-(2-chlorophenyl)-2-oxocyclohexyl)formamide

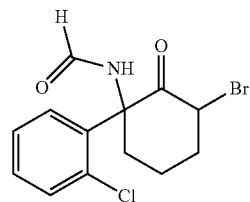 [SMILES: O=CNC1(c2ccccc2Cl)CCCC(Br)C1=O]

To a suspension of 2-amino-6-bromo-2-(2-chlorophenyl)cyclohexanone hydrobromide (Intermediate 1, 1.0 equiv) in DMF (0.2 M) is added DIEA (3 equiv.), HATU (1.2 equiv) and formic acid (1.5 equiv.) then the reaction mixture is stirred at room temperature for 2 h, and then the reaction is quenched with a saturated solution of $NaHCO_3$. The aqueous layer is extracted with EtOAc (3×). The combined organic layer is dried ($Na_2SO_4$) and evaporated. The residue is purified to give the title compound.

Intermediate 5. (1S,5R,8S)-5-(2-chlorophenyl)-8-iodo-3-(1-((4-methoxybenzyl)oxy)ethyl)-2-oxa-4-azabicyclo[3.3.1]non-3-en-9-one

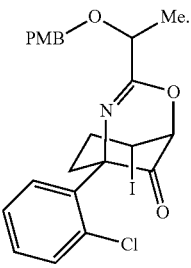

This compound may be prepared by methods known in the art, such as that described in *Molecules,* 2011, 16, 7691-7705.

Step 1. To a suspension of 1-amino-2'-chloro-5,6-dihydro-[1,1'-biphenyl]-2(1H)-one hydrobromide (Intermediate 2, 1.0 equiv.) in $CHCl_3$ (0.26 M) is added $Et_3N$ (2 equiv.) and 2-((4-methoxybenzyl)oxy)propanoyl chloride (1.15 equiv.) and the reaction mixture is stirred at room temperature for 2 h, and then washed with $H_2O$ two times. The aqueous layer is extracted with EtOAc three times. The combined organic layer is dried ($Na_2SO_4$) and evaporated, and the residue is recrystallized to give N—((R)-2'-chloro-6-oxo-1,2,3,6-tetrahydro-[1,1'-biphenyl]-1-yl)-2-(4-methoxybenzyl)oxy)propanamide.

Step 2. A solution of N—((R)-2'-chloro-6-oxo-1,2,3,6-tetrahydro-[1, 1'-biphenyl]-1-yl)-2-((4-methoxybenzyl)oxy) propanamide (1.0 equiv) in $CH_2Cl_2$ (0.13 M) is treated with NIS (1.0 equiv) and subsequently stirred for 14 h at room temperature. When the reaction is complete, the mixture is washed with 10% NaOH solution three times. The aqueous solution is extracted with $CH_2Cl_2$ three times and the combined organic phase is dried ($Na_2SO_4$) and evaporated to give the title compound.

Intermediate 6. N-(1-(2-chlorophenyl)-3-hydroxy-2-oxocyclohexyl)acetamide

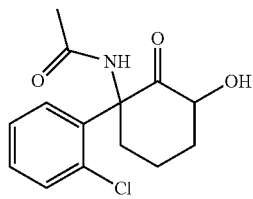 [SMILES: CC(=O)NC1(c2ccccc2Cl)CCCC(O)C1=O]

This compound may be prepared in a manner analogous to that described in *J. Med. Chem,* 2007, 50, 5311-5323, for example, as follows.

To a solution of 2-amino-2-(2-chlorophenyl)-6-hydroxycyclohexanone (Intermediate 3, 1.0 equiv) in methanol (0.05 M) is added acetic anhydride (1.1 equiv.) and the reaction mixture is stirred at room temperature for 4 h. Upon completion of the reaction, the solution is neutralized with a 10% sodium bicarbonate solution (pH=8) then made basic with a 10% ammonia solution (pH=10). The organic layer is extracted with dichloromethane, washed with brine, dried ($Na_2SO_4$) and then the solvent is evaporated. The crude residue is purified by column chromatography to give the title compound.

Example 1. (1R,5R)-5-(2-chlorophenyl)-2-oxa-4-azabicyclo[3.3.1]non-3-en-9-one

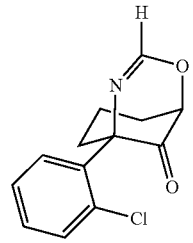 [SMILES: O=C1C2CCCC1(c1ccccc1Cl)N=CO2]

This compound may be prepared in a manner analogous to that described in *J. Org. Chem.,* 2007, 72, 8656-8670, *J. Org. Chem.,* 2011, 76, 680-683, and *Org. Lett.,* 2016, 18, 948-951, for example, as follows.

A solution of N-(3-bromo-1-(2-chlorophenyl)-2-oxocyclohexyl)formamide (Intermediate 4, 1.0 equiv) in dry DMF (0.06 M) is treated with NaH (1.0 equiv) at 0° C. The reaction mixture is stirred at 0° C. for 15 min and then at room temperature until TLC or LCMS reveals the disappearance of the starting material. Next, the reaction mixture is quenched with $H_2O$ and extracted three times with $Et_2O$. The combined organic layers are washed with $H_2O$ three times and dried over $Na_2SO_4$. Flash chromatography on silica gel affords the desired compound.

Example 2. (1R,5R)-5-(2-chlorophenyl)-3-(1-hydroxyethyl)-2-oxa-4 azabicyclo[3.3.1]non-3-en-9-one

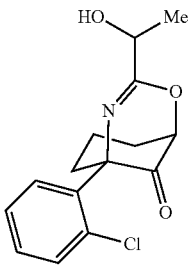 [SMILES: CC(O)C1=NC2(c3ccccc3Cl)CCCC(O1)C2=O]

This compound may be prepared in a manner analogous to that described in *Molecules,* 2011, 16, 7691-7705, as follows.

Step 1. $Bu_3SnH$ (2.1 equiv.) is added to a solution of (1S,5R,8S)-5-(2-chlorophenyl)-8-iodo-3-(1-((4-methoxybenzyl)oxy)ethyl)-2-oxa-4-azabicyclo[3.3.1]non-3-en-9-one (Intermediate 5, 1.0 equiv) in dry $CH_2Cl_2$ (0.1 M) under Ar. After stirring for 20 h at 40° C., the solvent is evaporated off and the residue is purified by column chromatography on silica gel (n-hexane:EtOAc 10:1) to afford (1R,5R)-5-(2-chlorophenyl)-3-(1-(((4-methoxybenzyl)oxy)ethyl)-2-oxa-4-azabicyclo[3.3.1]non-3-en-9-one.

Step 2. To a solution of (1R,5R)-5-(2-chlorophenyl)-3-(1-((4-methoxybenzyl)oxy)ethyl)-2-oxa-4-azabicyclo[3.3.1]non-3-en-9-one (1.0 equiv) in a mixture of dichloromethane/ water (100:1, 0.06 M) at 0° C. is added DDQ (1.2 equiv) and the resulting mixture is stirred at room temperature for several hours. Upon completion of the reaction, the reaction mixture is washed with a 40% aqueous sodium hydrogencarbonate solution, followed by brine. The organic layer is dried (Na$_2$SO$_4$) and solvent is removed under reduced pressure. The crude product is purified to give the title compound.

Example 3. (1R,5R)-5-(2-chlorophenyl)-3-methyl-2-oxa-4-azabicyclo[3.3.1]non-3-en-9-one

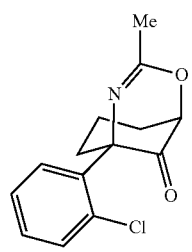 [SMILES: CC1=NC2(c3ccccc3Cl)CCCC(O1)C2=O]

This compound may be prepared in a manner analogous to that described in *J Med. Chem.*, 2007, 50, 5311-5323, as follows.

Step 1. To a suspension of N-(1-(2-chlorophenyl)-3-hydroxy-2-oxocyclohexyl)acetamide (Intermediate 6, 1.0 equiv) in freshly distilled ethylene glycol (0.02 M) is added sodium hydroxide (0.2 equiv). After heating at 215° C. for 6 h, the mixture is then made basic with a 10% ammonia solution (pH=10) and extracted with dichloromethane. The organic layer is dried over Na$_2$SO$_4$ and filtered, and the solvent is evaporated to give the title compound.

The compounds of Examples 4-61, corresponding to the (1R,5R) enantiomers, may each be prepared in a manner analogous to those of Examples 1-3, with appropriate starting material substitutions and protection or deprotection steps as would be appreciated by those of skill in the art. In addition, the corresponding (1S,5S) enantiomers of Examples 1-61 can be synthesized in a manner similar to that described using the appropriate starting material substitutions and synthetic procedures as known to one skilled in the art.

Example 4. (1R,5R)-3-((S)-1-amino-2-methylpropyl)-5-(2-chlorophenyl)-2-oxa-4-azabicyclo[3.3.1]non-3-en-9-one

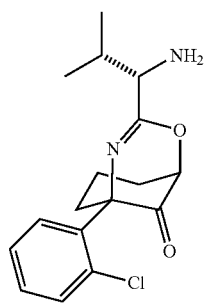

Example 5. (1R,5R)-3-(aminomethyl)-5-(2-chlorophenyl)-2-oxa-4-azabicyclo[3.3.1]non-3-en-9-one

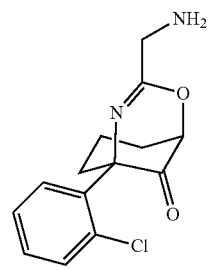 [SMILES: NCC1=NC2(c3ccccc3Cl)CCCC(O1)C2=O]

Example 6. (1R,5R)-5-(2-chlorophenyl)-3-fluorocarbonyl-2-oxa-4-azabicyclo[3.3.1]non-3-en-9-one

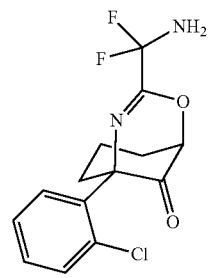 [SMILES: NC(F)(F)C1=NC2(c3ccccc3Cl)CCCC(O1)C2=O]

Example 7. (1R,5R)-5-(2-chlorophenyl)-3-((S)-1,5-diaminopentyl)-2-oxa-4-azabicyclo[3.3.1]non-3-en-9-one

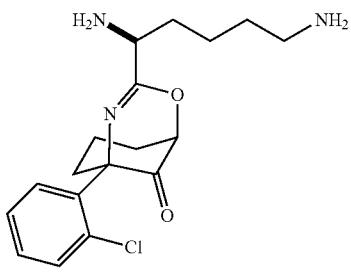 [SMILES: NCCCC[C@H](N)C1=NC2(c3ccccc3Cl)CCCC(O1)C2=O]

Example 8. (1R,5R)-3-((S)-1-aminoethyl)-5-(2-chlorophenyl)-2-oxa-4-azabicyclo[3.3.1]non-3-en-9-one

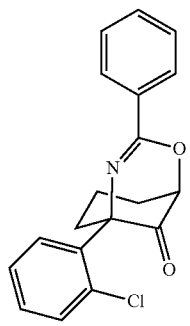 [SMILES: O=C1C2CCCC1(c1ccccc1Cl)N=C(c1ccccc1)O2]

Example 9. (1R,5R)-5-(2-chlorophenyl)-3-phenyl-2-oxa-4-azabicyclo[3.3.1]non-3-en-9-one Example 10. (1R,5R)-3-((1S,2R)-1-amino-2-methylbutyl)-5-(2-chlorophenyl)-2-oxa-4-azabicyclo[3.3.1]non-3-en-9-one

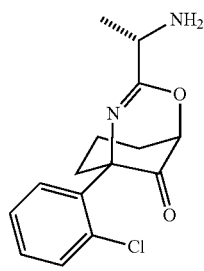 [SMILES: C[C@H](N)C1=NC2(c3ccccc3Cl)CCCC(O1)C2=O]

Example 11. (1R,5R)-3-((S)-1-amino-3-methylbutyl)-5-(2-chlorophenyl)-2-oxa-4-azabicyclo[3.3.1]non-3-en-9-one

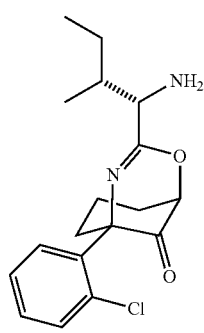 [SMILES: CCC(C)[C@H](N)C1=NC2(c3ccccc3Cl)CCCC(O1)C2=O]

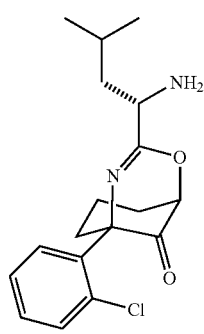 [SMILES: CC(C)C[C@H](N)C1=NC2(c3ccccc3Cl)CCCC(O1)C2=O]

Example 12. (1R,5R)-3-((S)-1-amino-2-phenylethyl)-5-(2-chlorophenyl)-2-oxa-4-azabicyclo[3.3.1]non-3-en-9-one

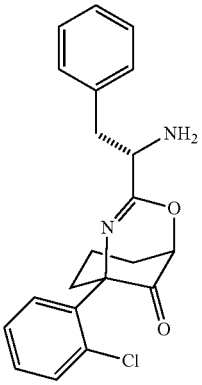 [SMILES: N[C@@H](Cc1ccccc1)C1=NC2(c3ccccc3Cl)CCCC(O1)C2=O]

Example 13. (1R,5R)-3-((S)-1-amino-2-(4-hydroxyphenyl)ethyl)-5-(2-chlorophenyl)-2-oxa-4-azabicyclo[3.3.1]non-3-en-9-one

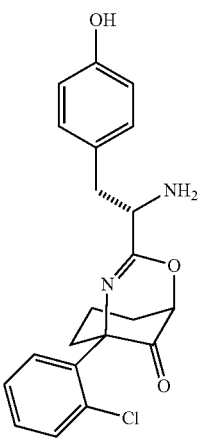 [SMILES: N[C@@H](Cc1ccc(O)cc1)C1=NC2(c3ccccc3Cl)CCCC(O1)C2=O]

Example 14. (1R,5R)-3-((S)-1-amino-2-(1H-indol-3-yl)ethyl)-5-(2-chlorophenyl)-2-oxa-4-azabicyclo[3.3.1]non-3-en-9-one

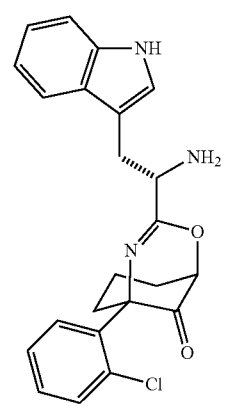

Example 15. (1R,5R)-3-((S)-1-amino-2-(1H-imidazol-4-yl)ethyl)-5-(2-chlorophenyl)-2-oxa-4-azabicyclo[3.3.1]non-3-en-9-one

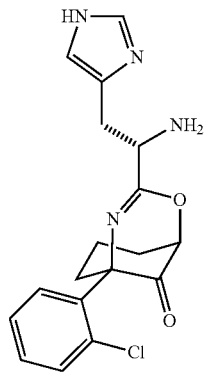 [SMILES: N[C@@H](Cc1c[nH]cn1)C1=NC2(c3ccccc3Cl)CCCC(O1)C2=O]

Example 16. (1R,5R)-5-(2-chlorophenyl)-3-(pyrrolidin-2-yl)-2-oxa-4-azabicyclo[3.3.1]non-3-en-9-one

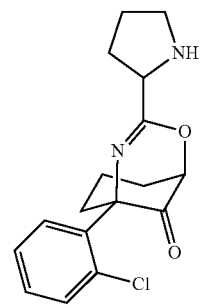 [SMILES: O=C1C2CCCC1(c1ccccc1Cl)N=C(C1CCCN1)O2]

Example 17. (S)-3-amino-3-((1R,5R)-5-(2-chlorophenyl)-9-oxo-2-oxa-4-azabicyclo[3.3.1]non-3-en-3-yl)propanoic acid

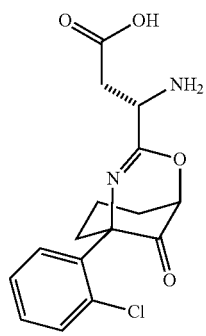 [SMILES: N[C@@H](CC(=O)O)C1=NC2(c3ccccc3Cl)CCCC(O1)C2=O]

Example 18. (S)-4-amino-4-((1R,5R)-5-(2-chlorophenyl)-9-oxo-2-oxa-4-azabicyclo[3.3.1]non-3-en-3-yl)butanoic acid

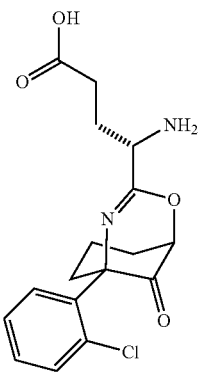 [SMILES: N[C@@H](CCC(=O)O)C1=NC2(c3ccccc3Cl)CCCC(O1)C2=O]

Example 19. (S)-4-amino-4-((1R,5R)-5-(2-chlorophenyl)-9-oxo-2-oxa-4-azabicyclo[3.3.1]non-3-en-3-yl)butanamide

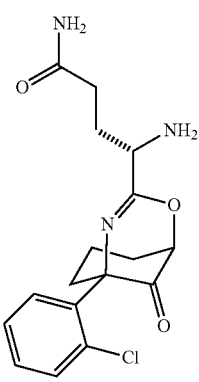

Example 20. (S)-3-amino-3-((1R,5R)-5-(2-chlorophenyl)-9-oxo-2-oxa-4-azabicyclo[3.3.1]non-3-en-3-yl)propanamide

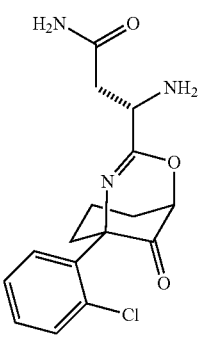

Example 21. (1R,5R)-3-((S)-1-amino-3-(methylthio)propyl)-5-(2-chlorophenyl)-2-oxa-4-azabicyclo[3.3.1]non-3-en-9-one

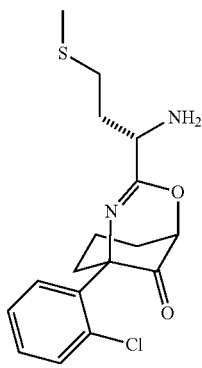

Example 22. (1R,5R)-3-((R)-1-amino-2-mercaptoethyl)-5-(2-chlorophenyl)-2-oxa-4-azabicyclo[3.3.1]non-3-en-9-one

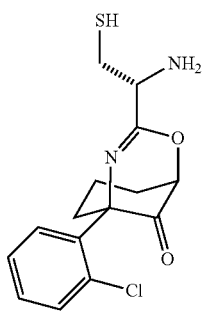

Example 23. (1R,5R)-3-((S)-1-amino-2-hydroxyethyl)-5-(2-chlorophenyl)-2-oxa-4-azabicyclo[3.3.1]non-3-en-9-one

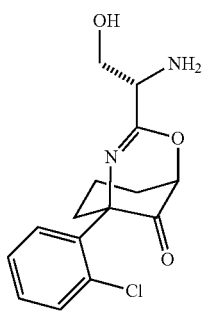

Example 24. (1R,5R)-3-((S)-1-amino-2-methoxyethyl)-5-(2-chlorophenyl)-2-oxa-4-azabicyclo[3.3.1]non-3-en-9-one

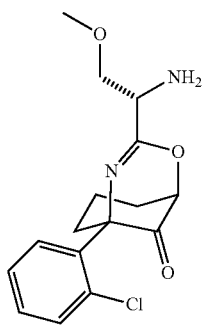

Example 25. 1-((S)-4-amino-4-((1R,5R)-5-(2-chlorophenyl)-9-oxo-2-oxa-4-azabicyclo[3.3.1]non-3-en-3-yl)butyl)guanidine

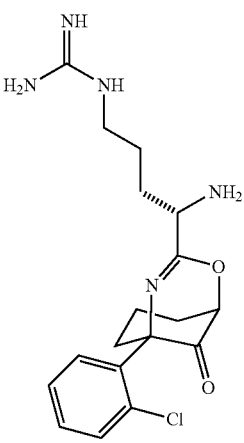

Example 26. (1R,5R)-5-(2-chlorophenyl)-3-ethyl-2-oxa-4-azabicyclo[3.3.1]non-3-en-9-one

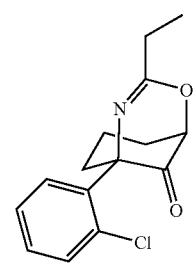 [SMILES: CCC1=NC2(c3ccccc3Cl)CCCC(O1)C2=O]

Example 27. 3-((1R,5R)-5-(2-chlorophenyl)-9-oxo-2-oxa-4-azabicyclo[3.3.1]non-3-en-3-yl)-2-hydroxypropanoic acid

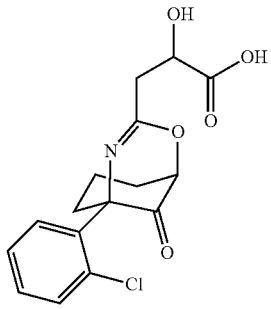 [SMILES: O=C(O)C(O)CC1=NC2(c3ccccc3Cl)CCCC(O1)C2=O]

Example 28. 2-(((1R,5R)-5-(2-chlorophenyl)-9-oxo-2-oxa-4-azabicyclo[3.3.1]non-3-en-3-yl)methyl)-2-hydroxysuccinic acid

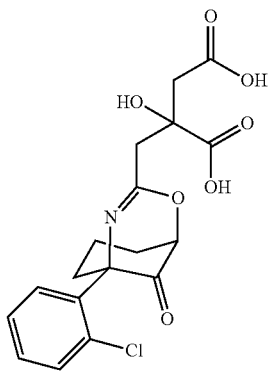 [SMILES: O=C(O)CC(O)(CC1=NC2(c3ccccc3Cl)CCCC(O1)C2=O)C(=O)O]

Example 29. 5-((1R,5R)-5-(2-chlorophenyl)-9-oxo-2-oxa-4-azabicyclo[3.3.1]non-3-en-3-yl)pentanoic acid

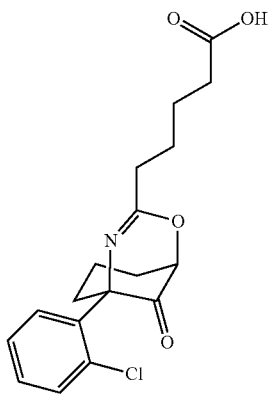 [SMILES: O=C(O)CCCCC1=NC2(c3ccccc3Cl)CCCC(O1)C2=O]

Example 30. 3-((1R,5R)-5-(2-chlorophenyl)-9-oxo-2-oxa-4-azabicyclo[3.3.1]non-3-en-3-yl)-2,3-dihydroxypropanoic acid

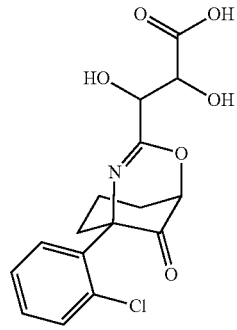 [SMILES: O=C(O)C(O)C(O)C1=NC2(c3ccccc3Cl)CCCC(O1)C2=O]

Example 31. 3-((1R,5R)-5-(2-chlorophenyl)-9-oxo-2-oxa-4-azabicyclo[3.3.1]non-3-en-3-yl)propanoic acid

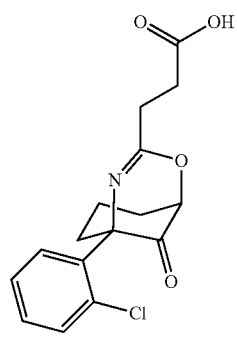 [SMILES: O=C(O)CCC1=NC2(c3ccccc3Cl)CCCC(O1)C2=O]

Example 32. (1R,5R)-5-(2-chlorophenyl)-3-heptyl-2-oxa-4-azabicyclo[3.3.1]non-3-en-9-one

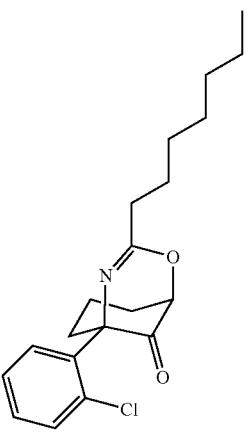 [SMILES: CCCCCCCC1=NC2(c3ccccc3Cl)CCCC(O1)C2=O]

Example 33. (1R,5R)-3-(1-amino-2-hydroseleno-ethyl)-5-(2-chlorophenyl)-2-oxa-4-azabicyclo[3.3.1]non-3-en-9-one

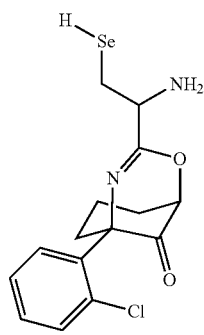 [SMILES: NC(C[SeH])C1=NC2(c3ccccc3Cl)CCCC(O1)C2=O]

Example 34. (1R,5R)-5-(2-chlorophenyl)-3-(2-(methylamino)ethyl)-2-oxa-4-azabicyclo[3.3.1]non-3-en-9-one

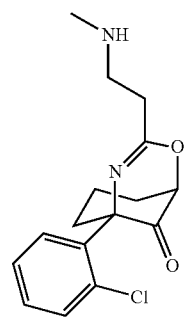 [SMILES: CNCCC1=NC2(c3ccccc3Cl)CCCC(O1)C2=O]

Example 35. (1R,5R)-5-(2-chlorophenyl)-3-(1,2-diaminoethyl)-2-oxa-4-azabicyclo[3.3.1]non-3-en-9-one

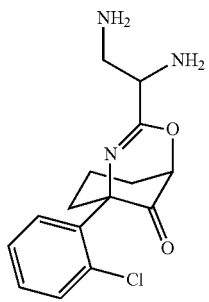 [SMILES: NCC(N)C1=NC2(c3ccccc3Cl)CCCC(O1)C2=O]

Example 36. (1R,5R)-3-(2-amino-1-hydroxyethyl)-5-(2-chlorophenyl)-2-oxa-4-azabicyclo[3.3.1]non-3-en-9-one

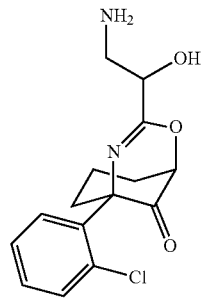 [SMILES: NCC(O)C1=NC2(c3ccccc3Cl)CCCC(O1)C2=O]

Example 37. (1R,5R)-3-(3-aminopropyl)-5-(2-chlorophenyl)-2-oxa-4-azabicyclo[3.3.1]non-3-en-9-one

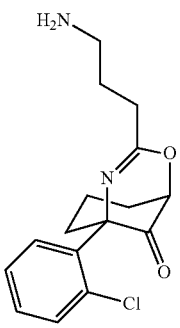 [SMILES: NCCCC1=NC2(c3ccccc3Cl)CCCC(O1)C2=O]

Example 38. (1R,5R)-3-(4-aminobutyl)-5-(2-chlorophenyl)-2-oxa-4-azabicyclo[3.3.1]non-3-en-9-one

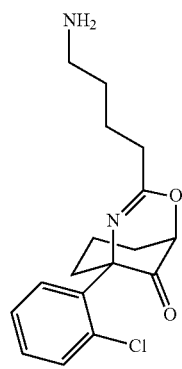 [SMILES: NCCCCC1=NC2(c3ccccc3Cl)CCCC(O1)C2=O]

Example 39. (1R,5R)-3-(3-aminopentyl)-5-(2-chlorophenyl)-2-oxa-4-azabicyclo[3.3.1]non-3-en-9-one

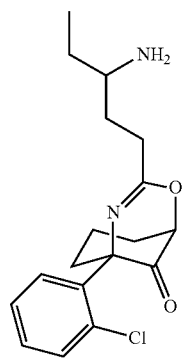 [SMILES: CCC(N)CCC1=NC2(c3ccccc3Cl)CCCC(O1)C2=O]

Example 40. (1R,5R)-3-(1-amino-3-hydroxypropyl)-5-(2-chlorophenyl)-2-oxa-4-azabicyclo[3.3.1]non-3-en-9-one

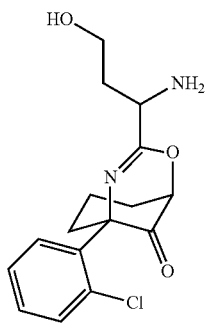 [SMILES: NC(CCO)C1=NC2(c3ccccc3Cl)CCCC(O1)C2=O]

Example 41. (1R,5R)-5-(2-chlorophenyl)-3-(1,4-diaminobutyl)-2-oxa-4-azabicyclo[3.3.1]non-3-en-9-one

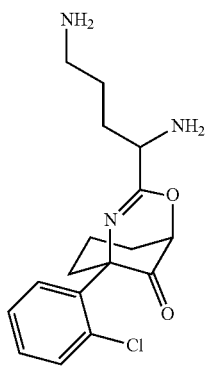 [SMILES: NCCCC(N)C1=NC2(c3ccccc3Cl)CCCC(O1)C2=O]

Example 42. 4-amino-4-((1R,5R)-5-(2-chlorophenyl)-9-oxo-2-oxa-4-azabicyclo[3.3.1]non-3-en-3-yl)-N-ethylbutanamide

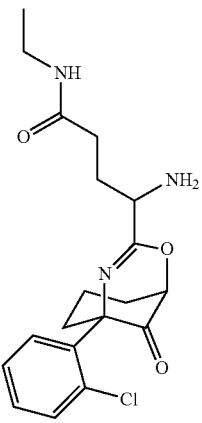 [SMILES: CCNC(=O)CCC(N)C1=NC2(c3ccccc3Cl)CCCC(O1)C2=O]

Example 43. (1R,5R)-5-(2-chlorophenyl)-3-(1,5-diamino-4-hydroxypentyl)-2-oxa-4-azabicyclo[3.3.1]non-3-en-9-one

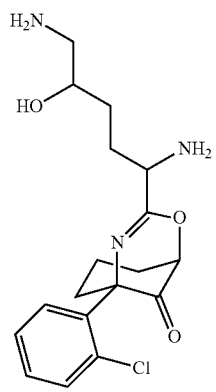 [SMILES: NCC(O)CCC(N)C1=NC2(c3ccccc3Cl)CCCC(O1)C2=O]

Example 44. 1-(4-amino-4-((1R,5R)-5-(2-chlorophenyl)-9-oxo-2-oxa-4-azabicyclo[3.3.1]non-3-en-3-yl)butyl)urea

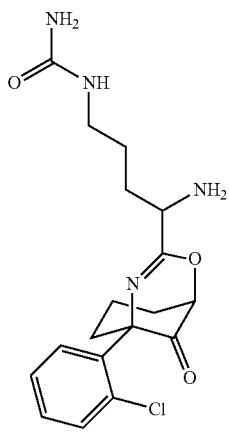 [SMILES: NC(=O)NCCCC(N)C1=NC2(c3ccccc3Cl)CCCC(O1)C2=O]

Example 45. 1-(5-amino-5-((1R,5R)-5-(2-chlorophenyl)-9-oxo-2-oxa-4-azabicyclo[3.3.1]non-3-en-3-yl)pentyl)urea

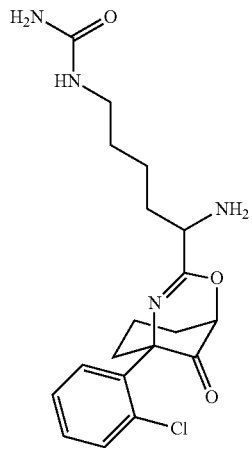 [SMILES: NC(=O)NCCCCC(N)C1=NC2(c3ccccc3Cl)CCCC(O1)C2=O]

Example 46. 1-(5-amino-5-((1R,5R)-5-(2-chlorophenyl)-9-oxo-2-oxa-4-azabicyclo[3.3.1]non-3-en-3-yl)pentyl)guanidine

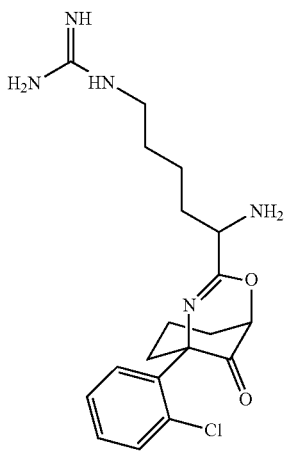 [SMILES: N=C(N)NCCCCC(N)C1=NC2(c3ccccc3Cl)CCCC(O1)C2=O]

Example 47. 1-(2-((1R,5R)-5-(2-chlorophenyl)-9-oxo-2-oxa-4-azabicyclo[3.3.1]non-3-en-3-yl)ethyl)guanidine

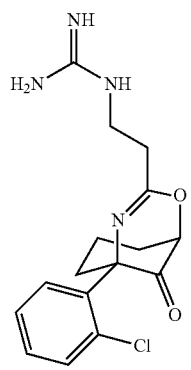

Example 48. (1R,5R)-3-(1-amino-2-methylbutyl)-5-(2-chlorophenyl)-2-oxa-4-azabicyclo[3.3.1]non-3-en-9-one

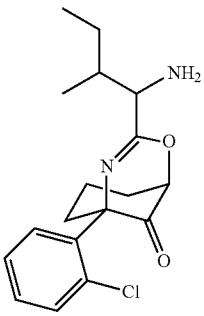 [SMILES: CCC(C)C(N)C1=NC2(c3ccccc3Cl)CCCC(O1)C2=O]

Example 49. (1R,5R)-3-(1-amino-2-(5-hydroxy-1H-indol-3-yl)ethyl)-5-(2-chlorophenyl)-2-oxa-4-azabicyclo[3.3.1]non-3-en-9-one

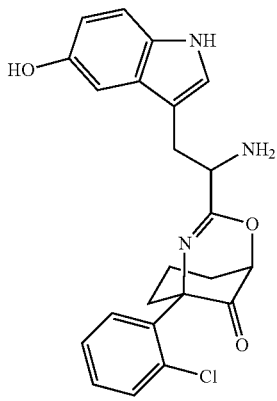 [SMILES: NC(Cc1c[nH]c2ccc(O)cc12)C1=NC2(c3ccccc3Cl)CCCC(O1)C2=O]

Example 50. (1R,5R)-3-(1-amino-2-(5-methyl-1H-indol-3-yl)ethyl)-5-(2-chlorophenyl)-2-oxa-4-azabicyclo[3.3.1]non-3-en-9-one

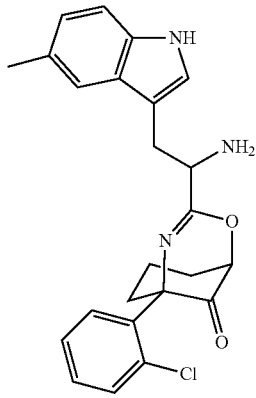 [SMILES: Cc1ccc2[nH]cc(CC(N)C3=NC4(c5ccccc5Cl)CCCC(O3)C4=O)c2c1]

Example 51. (1R,5R)-3-(2-(1H-indol-3-yl)-1-(methylamino)ethyl)-5-(2-chlorophenyl)-2-oxa-4-azabicyclo[3.3.1]non-3-en-9-one

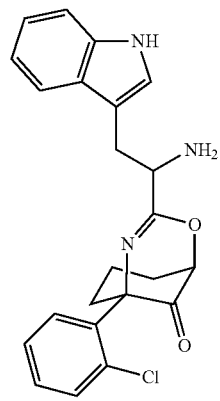 [SMILES: NC(Cc1c[nH]c2ccccc12)C1=NC2(c3ccccc3Cl)CCCC(O1)C2=O]

Example 52. (1R,5R)-5-(2-chlorophenyl)-3-(4-hydroxypyrrolidin-2-yl)-2-oxa-4-azabicyclo[3.3.1]non-3-en-9-one

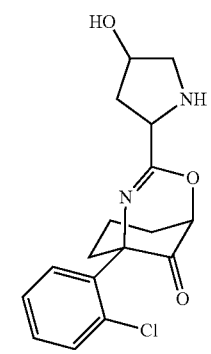 [SMILES: O=C1C2CCCC1(c1ccccc1Cl)N=C(C1CC(O)CN1)O2]

Example 53. (1R,5R)-3-(1-amino-2-hydroxy-3-methylbutyl)-5-(2-chlorophenyl)-2-oxa-4-azabicyclo[3.3.1]non-3-en-9-one

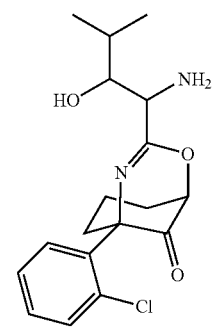 [SMILES: CC(C)C(O)C(N)C1=NC2(c3ccccc3Cl)CCCC(O1)C2=O]

Example 54. (1R,5R)-5-(2-chlorophenyl)-3-(1-(methylamino)ethyl)-2-oxa-4-azabicyclo[3.3.1]non-3-en-9-one

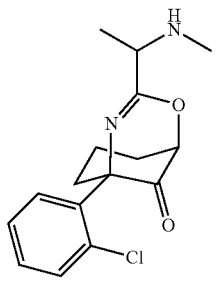 [SMILES: CNC(C)C1=NC2(c3ccccc3Cl)CCCC(O1)C2=O]

Example 55. (1R,5R)-3-(2-aminopropyl)-5-(2-chlorophenyl)-2-oxa-4-azabicyclo[3.3.1]non-3-en-9-one

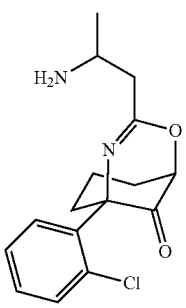 [SMILES: CC(N)CC1=NC2(c3ccccc3Cl)CCCC(O1)C2=O]

Example 56. N-(5-amino-5-((1R,5R)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide

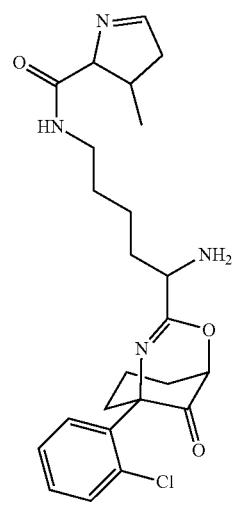 [SMILES: CC1CC=NC1C(=O)NCCCCC(N)C1=NC2(c3ccccc3Cl)CCCC(O1)C2=O]

Example 57. (1R,5R)-3-(1-amino-3-hydroxy-2-methylbutyl)-5-(2-chlorophenyl)-2-oxa-4-azabicyclo[3.3.1]non-3-en-9-one

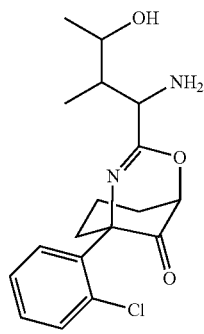 [SMILES: CC(O)C(C)C(N)C1=NC2(c3ccccc3Cl)CCCC(O1)C2=O]

Example 58. (1R,5R)-3-(1-amino-2,2-dimethylpropyl)-5-(2-chlorophenyl)-2-oxa-4-azabicyclo[3.3.1]non-3-en-9-one

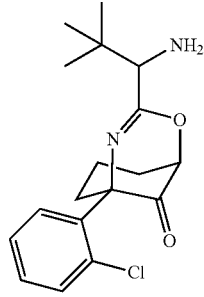 [SMILES: CC(C)(C)C(N)C1=NC2(c3ccccc3Cl)CCCC(O1)C2=O]

Example 59. (1R,5R)-3-(amino(3-amino-4-hydroxyphenyl)methyl)-5-(2-chlorophenyl)-2-oxa-4-azabicyclo[3.3.1]non-3-en-9-one

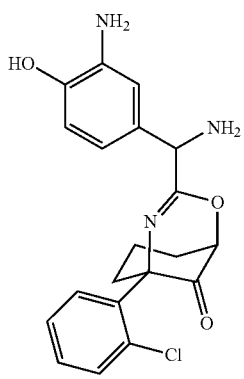 [SMILES: Nc1cc(C(N)C2=NC3(c4ccccc4Cl)CCCC(O2)C3=O)ccc1O]

Example 60. (1R,5R)-3-(1-amino-2-hydroxy-2-phenylethyl)-5-(2-chlorophenyl)-2-oxa-4-azabicyclo[3.3.1]non-3-en-9-one

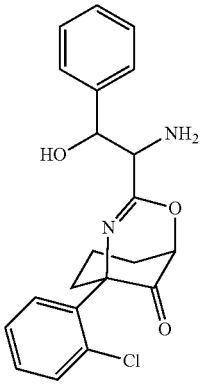 [SMILES: NC(C1=NC2(c3ccccc3Cl)CCCC(O1)C2=O)C(O)c1ccccc1]

Example 61. (1R,5R)-3-(1-amino-2-(4-methoxyphenyl)ethyl)-5-(2-chlorophenyl)-2-oxa-4-azabicyclo[3.3.1]non-3-en-9-one

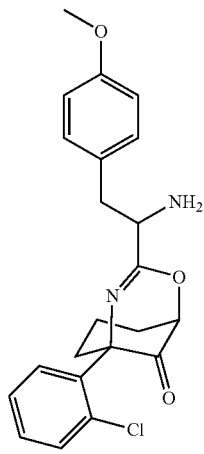 [SMILES: COc1ccc(CC(N)C2=NC3(c4ccccc4Cl)CCCC(O2)C3=O)cc1]

Models for Evaluating Anti-Depressant Activity

In this prophetic example, animal behavioral tests known in the art are used to evaluate the antidepressant efficacy of exemplary compounds of Formula (I). Such tests may be based on various attributes of depression, such as behavioral despair (e.g., Forced Swim), anxiety (e.g., Novelty Suppressed Feeding test), or exposure to uncontrollable stressors (e.g., Learned Helplessness).

Forced Swim Test

The Forced Swim Test (FST) is a widely used tool in depression research—particularly for evaluating the acute efficacy of candidate antidepressants. In the FST, mice are placed in an inescapable transparent tank filled with water and are evaluated for their escape related mobility behavior. See, e.g., Can et al., 2012, J. Vis. Exp. 59, e3638.

In some embodiments, mice are administered exemplary compounds of Formula (I) and exhibit a longer duration of escape-directed behaviors in the FST, compared to vehicle-administered controls.

Novelty Suppressed Feeding Test:

The Novelty Suppressed Feeding Test (NSFT) is based on the rationale that feeding to novelty is an anxiety symptom in rodents that can be evoked by novel environmental features, including novel food, novel testing area, and novel food containers. See, e.g., Santarelli et al., 2003, Science 301, 805-809. The test reflects the anti-anxiety effects of antidepressants, with a response measured after administration with candidate antidepressants.

In some embodiments, mice are administered exemplary compounds of Formula (I) and exhibit a decreased latency to feed in the NSFT, compared to vehicle-administered controls.

Learned Helplessness:

The learned helplessness test (LHT) is based on the observation that animals develop deficits in escape, cognitive and rewarded behaviors when subjected to repeated unavoidable and uncontrollable shocks. See, e.g., J. B. Overmier and Seligman, 1967, J. Comp. Physiol. Psychol. 63, 28-33; Chourbaji et al., 2005, Brain Res. Brain Res. Protoc. 16, 70-78; Zanos et al., 2016, Nature 533, 481-486.

In some embodiments, mice are administered exemplary compounds of Formula (I) and exhibit reduced deficits in the LHT, compared to vehicle-administered controls.

Pharmacokinetic Studies

In this prophetic example, pharmacokinetic profiles of Formula (I) compounds are obtained by standard means known in the art. For example, the pharmacokinetic profiles can be obtained from animals, such as mammals, including primates (e.g., monkeys such as Rhesus Macaques (*Macaca mulatta*), or humans).

Comparisons between pharmaceutical compositions can be readily achieved through the examination of pharmacokinetic profiles and/or parameters measured after administration of a composition. Generally, a blood baseline drug concentration is obtained prior to administration.

Post-administration, blood is drawn at various time points for drug analysis. Typically, serum or plasma is isolated from the blood samples and analyzed to determine the concentrations of the therapeutic agent. Drug concentrations in plasma (or serum) samples are analyzed by liquid chromatography-mass spectroscopy using appropriate parameters for each compound.

Typically, a graph is created of the time (x-axis) versus drug concentration (y-axis) and from this graph various pharmacokinetic parameters can be derived. Alternately, the data can be entered into a software program that will derive the pharmacokinetic parameters and fit them to a graph of the measured values.

Useful pharmacokinetic parameters in which to compare formulations include maximal blood therapeutic concentration ($C_{max}$), time to reach $C_{max}$ ($T_{max}$), time to reach a blood concentration of ½ of $C_{max}$ (T½), and bioavailability (BA). Typically, BA is measured by determining an area under the curve (AUC) of a blood therapeutic concentration versus time graph. For comparative analysis between pharmaceutical compositions, the pharmacokinetic parameters can be compared individually, or in various combinations. Numerous, but non-limiting, pharmacokinetic software programs can be used in practicing the teachings of the present disclosure, such Phoenix WinNonlin software, version 5.2.

Exemplary compounds of the present disclosure are tested for oral bioavailability. For such studies, the compounds can be dissolved in various vehicles (e.g. PEG 400 solution and CMC suspension) for intravenous and oral dosing in the rats. Following administration, plasma samples are obtained and extracted. The plasma concentrations of the starting compound and HNK metabolite are determined by high performance liquid chromatography/tandem mass spectrometry (LC/MS/MS) methods. Pharmacokinetic analyses are performed based on the plasma concentration data.

In some embodiments, pharmacokinetic data are analyzed, and significant levels of HNK metabolite are observed following oral administration of formula (I) compounds. Without being limited by mechanism, conversion of exemplary compounds of Formula (I) to the HNK may include one or more of a physiochemical, metabolic, or enzymatic process.

Therapeutic Administration of Formula (I) Compositions

The ability of compounds of the present disclosure to treat the disorders described herein can be evaluated using a suitably designed clinical study, such as that summarized below for a depressive disorder.

In this prophetic example, a clinical trial comprises a randomized, double-blind, placebo-controlled, multiple (21-day) dose study in twenty otherwise-healthy male and female patients with moderate-to-severe, major depressive disorder (as defined by the American Psychiatry Association Diagnostic and Statistical Manual of Mental Disorders (5th edition) and confirmed by the Mini International Neuropsychiatric Interview) of severity (as assessed by the Montgomery-Åsberg Depression Rating Scale).

The patients are randomized into 2 cohorts. Subjects in cohort 1 receive single doses of a Formula (I) solid dosage formulation on days 1-21. Subject in cohort 2 are identical to those for cohort 1, except that they receive single doses of placebo on days 1-21.

For each cohort, multiple parameters, including pharmacokinetics (PK), safety, and pharmacodynamics (PD) data are evaluated. In addition, cognitive function in Cohorts 1 and 2 is assessed using the CogState testing method, which comprises a customizable range of computerized cognitive tasks able to measure baseline and change in all cognitive domains. Specialized tasks in CogState can assess attention, memory, executive function, as well as language and social-emotional cognition.

Under the dosing duration of 3 weeks (21 days), there is evidence of Formula (I) compound-induced changes on PD endpoints that indicate an antidepressant effect. There is also evidence of a rapid onset of antidepressant effects, in some cases following a single dose. In addition, there is evidence of compound-induced changes in cognitive domain function.

In another prophetic example, comparable results are obtained from a similarly-designed clinical trial evaluating the efficacy of Formula (I) compounds in treating male and female patients with treatment-resistant depression (as defined by the American Psychiatry Association Diagnostic and Statistical Manual of Mental Disorders (5th Edition).

Conversion of Formula (I) Compositions

In this prophetic example, exemplary compounds of Formula (I) yield HNK upon administration to a subject, such as a patient in a clinical trial, in one or more steps. For example, in one possible pathway illustrated in the following schematic, exemplary compounds of Formula (I) may yield HNK in a two-step process, consisting of hydrolysis in Step 1 under acid conditions, such as those in the stomach, and subsequent enzymatic conversion by esterase action.

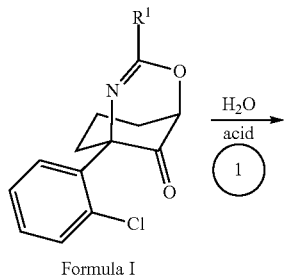

Formula I

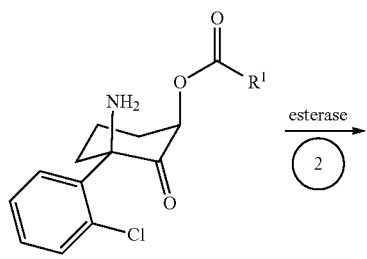

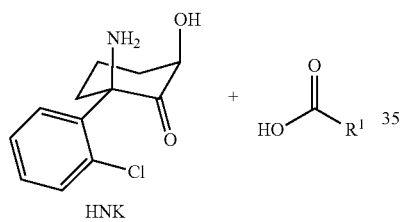

HNK

As a more specific example, a compound of Example 2 may give rise to HNK and lactic acid by the proposed two-step process, as illustrated in the following schematic.

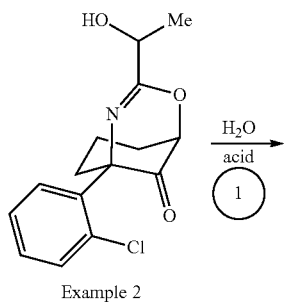

Example 2

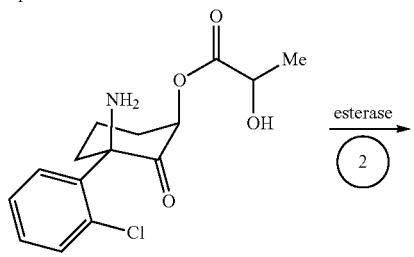

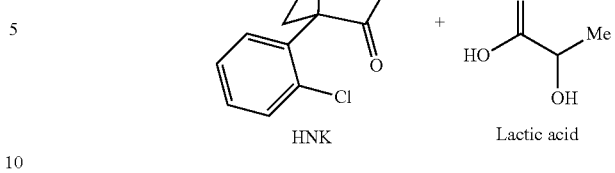

HNK · · · · · · · · · · · · · · · Lactic acid

The preceding schematics are for illustration purposes only and not intended to be limited to a particular mechanism or pathway, as other scenarios are also possible.

While certain embodiments are described herein, it is understood that the described embodiments are not intended to limit the scope of the disclosure as defined by the appended claims. On the contrary, the present disclosure is intended to cover alternatives, modifications and equivalents that may be included within the spirit and scope of the invention as defined by the appended claims. Furthermore, certain details in the present disclosure are provided to convey a thorough understanding of the invention defined by the appended claims. However, it will be apparent to those skilled in the art that certain embodiments may be practiced without these details. In certain instances, well-known methods, procedures, or other specific details have not been described to avoid unnecessarily obscuring aspects of the invention defined by the appended claims.

What is claimed is:

1. A compound, or pharmaceutically acceptable salt thereof, of Formula (I):

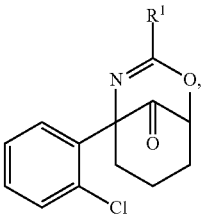

Formula (I)

wherein:
$R^1$ is —H; or
$R^1$ is —$C_{1-6}$alkyl, optionally substituted with one or more members, each independently selected from the group consisting of: -halo, -hydroxy, -alkoxy, -amino and -carboxyl; or
$R^1$ is —$C_{3-8}$alkenyl or —$C_{3-8}$alkynyl, each optionally substituted with one or more members, each independently selected from the group consisting of: -halo, -hydroxy, —$C_{1-4}$ alkyl, —$C_{1-4}$alkoxy, and amino; or
$R^1$ is —$(CH_2)_n$aryl, —$(CH_2)_n$heteroaryl, —$(CH_2)_n$cycloalkyl, or —$(CH_2)_n$heterocycloalkyl, each optionally substituted with one or more members, each independently selected from the group consisting of: -halo, -hydroxy, —$C_{1-4}$ alkyl, —$C_{1-4}$alkoxy, and -amino, wherein n is independently an integer selected from 0, 1, 2, 3, and 4; or
$R^1$ is —$COR^2$, —$CONR^3R^4$, —$CR^5R^6NR^7R^8$, —$CHR^9R^{10}$, or —$C(OH)R^{11}R^{12}$,
wherein $R^2$, $R^3$, $R^4$, $R^7$ and $R^8$ are each independently selected from the group consisting of: —H, —$C_{1-8}$ alkyl, and —$C_{1-8}$haloalkyl;

$R^5$ and $R^6$ are each independently selected from the group consisting of: —H, -halo, —NH$_2$, —C$_{1-8}$alkyl, —C$_{1-8}$haloalkyl, —(CH$_2$)$_n$ CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, —(CH$_2$)$_n$CONR$^{1A}$R$^{1B}$, —(CH$_2$)$_n$NHC(=O)R$^{1A}$, —(CH$_2$)$_n$NR$^{1A}$R$^{1B}$, —(CH$_2$)$_n$OR$^{1C}$, —(CH$_2$)$_n$ SR$^{1C}$ and —(CH$_2$)$_n$ SeR$^{1C}$, wherein n is independently an integer selected from 0, 1, 2, 3, and 4;

each R$^{1A}$ is independently selected from the group consisting of: —H, —C$_{1-8}$ alkyl, —(CH$_2$)$_n$ CONH$_2$, and (CH$_2$)$_n$heterocycloalkyl, wherein n is independently an integer selected from 0, 1, 2, 3, and 4;

each R$^{1B}$ is independently selected from the group consisting of: —H, —C$_{1-8}$alkyl, and —(CH$_2$)$_n$CONH$_2$, wherein n is independently an integer selected from 0, 1, 2, 3, and 4;

each R$^{1C}$ is independently selected from the group consisting of: —H—C$_{1-8}$alkyl, —C$_{1-8}$haloalkyl, —(CH$_2$)$_n$ CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, wherein n is independently an integer selected from 0, 1, 2, 3, and 4;

R$^9$ and R$^{10}$ are each independently selected from the group consisting of: —H, —C$_{1-8}$alkyl, and —C$_{1-8}$haloalkyl, said alkyl optionally substituted with up to 3 members, each independently selected from the group consisting of: -amino, -hydroxy and -carboxyl; or optionally R$^9$ and R$^{10}$ taken together with the carbon to which they are attached form an optionally substituted five membered heteroaryl or heterocycloalkyl ring; and R$^{11}$ and R$^{12}$ are independently selected from the group consisting of: —H, —C$_{1-6}$alkyl, and —C$_{1-6}$haloalkyl, said —C$_{1-6}$alkyl, and —C$_{1-6}$haloalkyl optionally substituted with up to 3 members, each independently selected from the group consisting of: -hydroxy and amino.

2. The compound, or pharmaceutically acceptable salt thereof, of claim 1, wherein:

R$^1$ is —H; or

R$^1$ is —C$_{1-6}$alkyl, optionally substituted with one or more members, each independently selected from the group consisting of: -halo, -hydroxy, -alkoxy, -amino and -carboxyl; or R$^1$ is —C$_{3-8}$alkenyl or —C$_{3-8}$alkynyl, each optionally substituted with one or more members, each independently selected from the group consisting of: -halo, -hydroxy, —C$_{1-4}$ alkyl, —C$_{1-4}$alkoxy, and amino; or R$^1$ is —(CH$_2$)$_n$aryl, —(CH$_2$)$_n$heteroaryl, —(CH$_2$)$_n$cycloalkyl, or —(CH$_2$)$_n$heterocycloalkyl, each optionally substituted with one or more members, each independently selected from the group consisting of: -halo, -hydroxy, —C$_{1-4}$ alkyl, —C$_{1-4}$alkoxy, and -amino, wherein n is independently an integer selected from 0, 1, 2, 3, and 4; or R$^1$ is —CR$^5$R$^6$NR$^7$R$^8$, —CHR$^9$R$^{10}$, or —C(OH)R$^{11}$R$^{12}$, wherein R$^7$ and R$^8$ are independently selected from the group consisting of: —H, —C$_{1-8}$alkyl, and —C$_{1-8}$haloalkyl;

R$^5$ and R$^6$ are each independently selected from the group consisting of: —H, -halo, —NH$_2$, —C$_{1-8}$alkyl, —C$_{1-8}$haloalkyl, —(CH$_2$)$_n$ CONH$_2$, —(CH$_2$)$_n$ COOH, —(CH$_2$)$_n$aryl, —(CH$_2$)$_n$heteroaryl, —(CH$_2$)$_n$cycloalkyl, and —(CH$_2$)$_n$heterocycloalkyl, each optionally substituted with one or more members, each independently selected from the group consisting of: -guanidyl, -urea, -halo, -alkyl, -hydroxy, -amino, -alkoxy, -2,3-dihydro-1H-pyrrole-1-carboxamide, —(CH$_2$)$_n$ NR$^{1A}$R$^{1B}$, —(CH$_2$)$_n$OR$^{1C}$, —(CH$_2$)$_n$ SR$^{1C}$ and —(CH$_2$)$_n$SeR$^{1C}$, wherein n is independently an integer selected from 0, 1, 2, 3, and 4;

each R$^{1A}$ is independently selected from the group consisting of: —H—C$_{1-8}$alkyl, and —(CH$_2$)$_n$heterocycloalkyl, wherein n is independently an integer selected from 0, 1, 2, 3, and 4;

each R$^{1B}$ is independently selected from the group consisting of: —H—C$_{1-8}$alkyl, wherein n is independently an integer selected from 0, 1, 2, 3, and 4;

each R$^{1C}$ is independently selected from the group consisting of: —H—C$_{1-8}$alkyl, —C$_{1-8}$haloalkyl, —(CH$_2$)$_n$aryl, —(CH$_2$)$_n$heteroaryl, —(CH$_2$)$_n$cycloalkyl, and —(CH$_2$)$_n$heterocycloalkyl, wherein n is independently an integer selected from 0, 1, 2, 3, and 4;

R$^9$ and R$^{10}$ are each independently selected from the group consisting of: —H, —C$_{1-8}$alkyl, and —C$_{1-8}$haloalkyl, said alkyl optionally substituted with up to 3 members, each independently selected from the group consisting of -amino, -hydroxy, and -carboxyl; or optionally R$^9$ and R$^{10}$ taken together with the carbon to which they are attached can form an optionally substituted five membered heteroaryl or heterocycloalkyl ring; and R$^{11}$ and R$^{12}$ are each independently selected from the group consisting of: —H, —C$_{1-6}$alkyl, and —C$_{1-6}$haloalkyl, said —C$_{1-6}$alkyl, and —C$_{1-6}$haloalkyl optionally substituted with up to 3 members, each independently selected from the group consisting of: -hydroxy and -amino.

3. The compound, or pharmaceutically acceptable salt thereof, of claim 1, wherein:

R$^1$ is —CR$^5$R$^6$NR$^7$R$^8$ or —CR$^9$R$^{10}$, wherein R$^5$ and R$^6$ are independently selected from the group consisting of: —H, —F, —Cl, —Br, —NH$_2$, -methyl, -ethyl, -n-propyl, -isopropyl, -butyl, -pentyl, —NH$_2$, —C$_{1-8}$haloalkyl, —(CH$_2$)$_n$ CONH$_2$, —(CH$_2$)$_n$ COOH, —(CH$_2$)$_n$aryl, —(CH$_2$)$_n$benzyl, —(CH$_2$)$_n$heteroaryl, —(CH$_2$)indole, —(CH$_2$)imidazole, —(CH$_2$)$_n$cycloalkyl, —(CH$_2$)$_n$heterocycloalkyl, —(CH$_2$)$_n$pyrrolidine, —(CH$_2$)furan, and —(CH$_2$)$_n$thiophene, optionally substituted with up to 3 members, each independently selected from the group consisting of: -guanidyl, -urea, -halo, -alkyl, -hydroxy, -amino, -alkoxy, -2,3-dihydro-1H-pyrrole-1-carboxamide, —(CH$_2$)$_n$ NR$^{1A}$R$^{1B}$, —(CH$_2$)$_n$OR$^{1C}$, —(CH$_2$)$_n$ SR$^{1C}$ and —(CH$_2$)$_n$SeR$^{1C}$, wherein n is independently an integer selected from 0, 1, 2, 3, and 4;

each R$^{1A}$ is independently selected from the group consisting of: —H, —C$_{1-8}$alkyl, and —(CH$_2$)$_n$heterocycloalkyl, wherein n is independently an integer selected from 0, 1, 2, 3, and 4;

each R$^{1B}$ is independently selected from the group consisting of: —H and C$_{1-8}$alkyl, wherein n is independently an integer selected from 0, 1, 2, 3, and 4;

each R$^{1C}$ is independently selected from the group consisting of: —H—C$_{1-8}$alkyl, —C$_{1-8}$haloalkyl, —(CH$_2$)$_n$aryl, —(CH$_2$)$_n$heteroaryl, —(CH$_2$)$_n$cycloalkyl, and —(CH$_2$)$_n$heterocycloalkyl, wherein n is independently an integer selected from 0, 1, 2, 3, and 4;

R⁷ and R⁸ are —H; and
R⁹ and R¹⁰ are independently selected from the group consisting of: —H, —$C_{1-8}$alkyl, and —$C_{1-8}$haloalkyl; or optionally R⁹ and R¹⁰ taken together with the carbon to which they are attached can form an optionally substituted five membered heteroaryl or heterocycloalkyl ring.

4. A compound selected from the group consisting of:
(1R,5R)-5-(2-chlorophenyl)-2-oxa-4-azabicyclo[3.3.1]non-3-en-9-one;
(1R,5R)-5-(2-chlorophenyl)-3-methyl-2-oxa-4-azabicyclo[3.3.1]non-3-en-9-one;
(1R,5R)-5-(2-chlorophenyl)-3-(1-hydroxyethyl)-2-oxa-4-azabicyclo[3.3.1]non-3-en-9-one;
(1R,5R)-3-((S)-1-amino-2-methylpropyl)-5-(2-chlorophenyl)-2-oxa-4-azabicyclo[3.3.1]non-3-en-9-one;
(1R,5R)-3-(aminomethyl)-5-(2-chlorophenyl)-2-oxa-4-azabicyclo[3.3.1]non-3-en-9-one;
(1R,5R)-5-(2-chlorophenyl)-3-fluorocarbonyl-2-oxa-4-azabicyclo[3.3.1]non-3-en-9-one;
(1R,5R)-5-(2-chlorophenyl)-3-((S)-1,5-diaminopentyl)-2-oxa-4-azabicyclo[3.3.1]non-3-en-9-one;
(1R,5R)-3-((S)-1-aminoethyl)-5-(2-chlorophenyl)-2-oxa-4-azabicyclo[3.3.1]non-3-en-9-one;
(1R,5R)-5-(2-chlorophenyl)-3-phenyl-2-oxa-4-azabicyclo[3.3.1]non-3-en-9-one;
(1R,5R)-3-((1S,2R)-1-amino-2-methylbutyl)-5-(2-chlorophenyl)-2-oxa-4-azabicyclo[3.3.1]non-3-en-9-one;
(1R,5R)-3-((S)-1-amino-3-methylbutyl)-5-(2-chlorophenyl)-2-oxa-4-azabicyclo[3.3.1]non-3-en-9-one;
(1R,5R)-3-((S)-1-amino-2-phenylethyl)-5-(2-chlorophenyl)-2-oxa-4-azabicyclo[3.3.1]non-3-en-9-one;
(1R,5R)-3-((S)-1-amino-2-(4-hydroxyphenyl)ethyl)-5-(2-chlorophenyl)-2-oxa-4-azabicyclo[3.3.1]non-3-en-9-one;
(1R,5R)-3-((S)-1-amino-2-(1H-indol-3-yl)ethyl)-5-(2-chlorophenyl)-2-oxa-4-azabicyclo[3.3.1]non-3-en-9-one;
(1R,5R)-3-((S)-1-amino-2-(1H-imidazol-4-yl)ethyl)-5-(2-chlorophenyl)-2-oxa-4-azabicyclo[3.3.1]non-3-en-9-one;
(1R,5R)-5-(2-chlorophenyl)-3-(pyrrolidin-2-yl)-2-oxa-4-azabicyclo[3.3.1]non-3-en-9-one;
(S)-3-amino-3-((1R,5R)-5-(2-chlorophenyl)-9-oxo-2-oxa-4-azabicyclo[3.3.1]non-3-en-3-yl)propanoic acid;
(S)-4-amino-4-((1R,5R)-5-(2-chlorophenyl)-9-oxo-2-oxa-4-azabicyclo[3.3.1]non-3-en-3-yl)butanoic acid;
(S)-4-amino-4-((1R,5R)-5-(2-chlorophenyl)-9-oxo-2-oxa-4-azabicyclo[3.3.1]non-3-en-3-yl)butanamide;
(S)-3-amino-3-((1R,5R)-5-(2-chlorophenyl)-9-oxo-2-oxa-4-azabicyclo[3.3.1]non-3-en-3-yl)propanamide;
(1R,5R)-3-((S)-1-amino-3-(methylthio)propyl)-5-(2-chlorophenyl)-2-oxa-4-azabicyclo[3.3.1]non-3-en-9-one;
(1R,5R)-3-((R)-1-amino-2-mercaptoethyl)-5-(2-chlorophenyl)-2-oxa-4-azabicyclo[3.3.1]non-3-en-9-one;
(1R,5R)-3-((S)-1-amino-2-hydroxyethyl)-5-(2-chlorophenyl)-2-oxa-4-azabicyclo[3.3.1]non-3-en-9-one;
(1R,5R)-3-((S)-1-amino-2-methoxyethyl)-5-(2-chlorophenyl)-2-oxa-4-azabicyclo[3.3.1]non-3-en-9-one;
1-((S)-4-amino-4-((1R,5R)-5-(2-chlorophenyl)-9-oxo-2-oxa-4-azabicyclo[3.3.1]non-3-en-3-yl)butyl)guanidine;
(1R,5R)-5-(2-chlorophenyl)-3-ethyl-2-oxa-4-azabicyclo[3.3.1]non-3-en-9-one;
3-((1R,5R)-5-(2-chlorophenyl)-9-oxo-2-oxa-4-azabicyclo[3.3.1]non-3-en-3-yl)-2-hydroxypropanoic acid;
2-(((1R,5R)-5-(2-chlorophenyl)-9-oxo-2-oxa-4-azabicyclo[3.3.1]non-3-en-3-yl)methyl)-2-hydroxysuccinic acid;
5-((1R,5R)-5-(2-chlorophenyl)-9-oxo-2-oxa-4-azabicyclo[3.3.1]non-3-en-3-yl)pentanoic acid;
3-((1R,5R)-5-(2-chlorophenyl)-9-oxo-2-oxa-4-azabicyclo[3.3.1]non-3-en-3-yl)-2,3-dihydroxypropanoic acid;
3-((1R,5R)-5-(2-chlorophenyl)-9-oxo-2-oxa-4-azabicyclo[3.3.1]non-3-en-3-yl)propanoic acid;
(1R,5R)-5-(2-chlorophenyl)-3-heptyl-2-oxa-4-azabicyclo[3.3.1]non-3-en-9-one;
(1R,5R)-3-(1-amino-2-hydroselenoethyl)-5-(2-chlorophenyl)-2-oxa-4-azabicyclo[3.3.1]non-3-en-9-one;
(1R,5R)-5-(2-chlorophenyl)-3-(2-(methylamino)ethyl)-2-oxa-4-azabicyclo[3.3.1]non-3-en-9-one;
(1R,5R)-5-(2-chlorophenyl)-3-(1,2-diaminoethyl)-2-oxa-4-azabicyclo[3.3.1]non-3-en-9-one;
(1R,5R)-3-(2-amino-1-hydroxyethyl)-5-(2-chlorophenyl)-2-oxa-4-azabicyclo[3.3.1]non-3-en-9-one;
(1R,5R)-3-(3-aminopropyl)-5-(2-chlorophenyl)-2-oxa-4-azabicyclo[3.3.1]non-3-en-9-one;
(1R,5R)-3-(4-aminobutyl)-5-(2-chlorophenyl)-2-oxa-4-azabicyclo[3.3.1]non-3-en-9-one;
(1R,5R)-3-(3-aminopentyl)-5-(2-chlorophenyl)-2-oxa-4-azabicyclo[3.3.1]non-3-en-9-one;
(1R,5R)-3-(1-amino-3-hydroxypropyl)-5-(2-chlorophenyl)-2-oxa-4-azabicyclo[3.3.1]non-3-en-9-one;
(1R,5R)-5-(2-chlorophenyl)-3-(1,4-diaminobutyl)-2-oxa-4-azabicyclo[3.3.1]non-3-en-9-one;
4-amino-4-((1R,5R)-5-(2-chlorophenyl)-9-oxo-2-oxa-4-azabicyclo[3.3.1]non-3-en-3-yl)-N-ethylbutanamide;
(1R,5R)-5-(2-chlorophenyl)-3-(1, 5-diamino-4-hydroxypentyl)-2-oxa-4-azabicyclo[3.3.1]non-3-en-9-one;
1-(4-amino-4-((1R,5R)-5-(2-chlorophenyl)-9-oxo-2-oxa-4-azabicyclo[3.3.1]non-3-en-3-yl)butyl)urea;
1-(5-amino-5-((1R,5R)-5-(2-chlorophenyl)-9-oxo-2-oxa-4-azabicyclo[3.3.1]non-3-en-3-yl)pentyl)urea;
1-(5-amino-5-((1R,5R)-5-(2-chlorophenyl)-9-oxo-2-oxa-4-azabicyclo[3.3.1]non-3-en-3-yl)pentyl)guanidine;
1-(2-((1R,5R)-5-(2-chlorophenyl)-9-oxo-2-oxa-4-azabicyclo[3.3.1]non-3-en-3-yl)ethyl)guanidine;
(1R,5R)-3-(1-amino-2-methylbutyl)-5-(2-chlorophenyl)-2-oxa-4-azabicyclo[3.3.1]non-3-en-9-one;
(1R,5R)-3-(1-amino-2-(5-hydroxy-1H-indol-3-yl)ethyl)-5-(2-chlorophenyl)-2-oxa-4-azabicyclo[3.3.1]non-3-en-9-one;
(1R,5R)-3-(1-amino-2-(5-methyl-1H-indol-3-yl)ethyl)-5-(2-chlorophenyl)-2-oxa-4-azabicyclo[3.3.1]non-3-en-9-one;
(1R,5R)-3-(2-(1H-indol-3-yl)-1-(methylamino)ethyl)-5-(2-chlorophenyl)-2-oxa-4-azabicyclo[3.3.1]non-3-en-9-one;
(1R,5R)-5-(2-chlorophenyl)-3-(4-hydroxypyrrolidin-2-yl)-2-oxa-4-azabicyclo[3.3.1]non-3-en-9-one;
(1R,5R)-3-(1-amino-2-hydroxy-3-methylbutyl)-5-(2-chlorophenyl)-2-oxa-4-azabicyclo[3.3.1]non-3-en-9-one;
(1R,5R)-5-(2-chlorophenyl)-3-(1-(methylamino)ethyl)-2-oxa-4-azabicyclo[3.3.1]non-3-en-9-one;
(1R,5R)-3-(2-aminopropyl)-5-(2-chlorophenyl)-2-oxa-4-azabicyclo[3.3.1]non-3-en-9-one;
N-(5-amino-5-((1R,5R)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;
(1R,5R)-3-(1-amino-3-hydroxy-2-methylbutyl)-5-(2-chlorophenyl)-2-oxa-4-azabicyclo[3.3.1]non-3-en-9-one;

(1R,5R)-3-(1-amino-2,2-dimethylpropyl)-5-(2-chlorophenyl)-2-oxa-4-azabicyclo[3.3.1]non-3-en-9-one;
(1R,5R)-3-(amino(3-amino-4-hydroxyphenyl)methyl)-5-(2-chlorophenyl)-2-oxa-4-azabicyclo[3.3.1]non-3-en-9-one;
(1R,5R)-3-(1-amino-2-hydroxy-2-phenylethyl)-5-(2-chlorophenyl)-2-oxa-4-azabicyclo[3.3.1]non-3-en-9-one;
(1R,5R)-3-(1-amino-2-(4-methoxyphenyl)ethyl)-5-(2-chlorophenyl)-2-oxa-4-azabicyclo[3.3.1]non-3-en-9-one;
(1S,5S)-5-(2-chlorophenyl)-2-oxa-4-azabicyclo[3.3.1]non-3-en-9-one;
(1S,5S)-5-(2-chlorophenyl)-3-methyl-2-oxa-4-azabicyclo[3.3.1]non-3-en-9-one;
(1S,5S)-5-(2-chlorophenyl)-3-(1-hydroxyethyl)-2-oxa-4-azabicyclo[3.3.1]non-3-en-9-one;
(1S,5S)-3-((S)-1-amino-2-methylpropyl)-5-(2-chlorophenyl)-2-oxa-4-azabicyclo[3.3.1]non-3-en-9-one;
(1S,5S)-3-(aminomethyl)-5-(2-chlorophenyl)-2-oxa-4-azabicyclo[3.3.1]non-3-en-9-one;
(1S,5S)-5-(2-chlorophenyl)-3-fluorocarbonyl-2-oxa-4-azabicyclo[3.3.1]non-3-en-9-one;
(1S,5S)-5-(2-chlorophenyl)-3-((S)-1, 5-diaminopentyl)-2-oxa-4-azabicyclo[3.3.1]non-3-en-9-one;
(1S,5S)-3-((S)-1-aminoethyl)-5-(2-chlorophenyl)-2-oxa-4-azabicyclo[3.3.1]non-3-en-9-one;
(1S,5S)-5-(2-chlorophenyl)-3-phenyl-2-oxa-4-azabicyclo[3.3.1]non-3-en-9-one;
(1S,5S)-3-((1S,2R)-1-amino-2-methylbutyl)-5-(2-chlorophenyl)-2-oxa-4-azabicyclo[3.3.1]non-3-en-9-one;
(1S,5S)-3-((S)-1-amino-3-methylbutyl)-5-(2-chlorophenyl)-2-oxa-4-azabicyclo[3.3.1]non-3-en-9-one;
(1S,5S)-3-((S)-1-amino-2-phenylethyl)-5-(2-chlorophenyl)-2-oxa-4-azabicyclo[3.3.1]non-3-en-9-one;
(1S,5S)-3-((S)-1-amino-2-(4-hydroxyphenyl)ethyl)-5-(2-chlorophenyl)-2-oxa-4-azabicyclo[3.3.1]non-3-en-9-one;
(1S,5S)-3-((S)-1-amino-2-(1H-indol-3-yl)ethyl)-5-(2-chlorophenyl)-2-oxa-4-azabicyclo[3.3.1]non-3-en-9-one;
(1S,5S)-3-((S)-1-amino-2-(1H-imidazol-4-yl)ethyl)-5-(2-chlorophenyl)-2-oxa-4-azabicyclo[3.3.1]non-3-en-9-one;
(1S,5S)-5-(2-chlorophenyl)-3-(pyrrolidin-2-yl)-2-oxa-4-azabicyclo[3.3.1]non-3-en-9-one;
(S)-3-amino-3-((1S,5S)-5-(2-chlorophenyl)-9-oxo-2-oxa-4-azabicyclo[3.3.1]non-3-en-3-yl)propanoic acid;
(S)-4-amino-4-((1S,5S)-5-(2-chlorophenyl)-9-oxo-2-oxa-4-azabicyclo[3.3.1]non-3-en-3-yl)butanoic acid;
(S)-4-amino-4-((1S,5S)-5-(2-chlorophenyl)-9-oxo-2-oxa-4-azabicyclo[3.3.1]non-3-en-3-yl)butanamide;
(S)-3-amino-3-((1S,5S)-5-(2-chlorophenyl)-9-oxo-2-oxa-4-azabicyclo[3.3.1]non-3-en-3-yl)propanamide;
(1S,5S)-3-((S)-1-amino-3-(methylthio)propyl)-5-(2-chlorophenyl)-2-oxa-4-azabicyclo[3.3.1]non-3-en-9-one;
(1S,5S)-3-((R)-1-amino-2-mercaptoethyl)-5-(2-chlorophenyl)-2-oxa-4-azabicyclo[3.3.1]non-3-en-9-one;
(1S,5S)-3-((S)-1-amino-2-hydroxyethyl)-5-(2-chlorophenyl)-2-oxa-4-azabicyclo[3.3.1]non-3-en-9-one;
(1S,5S)-3-((S)-1-amino-2-methoxyethyl)-5-(2-chlorophenyl)-2-oxa-4-azabicyclo[3.3.1]non-3-en-9-one;
1-((S)-4-amino-4-((1S,5S)-5-(2-chlorophenyl)-9-oxo-2-oxa-4-azabicyclo[3.3.1]non-3-en-3-yl)butyl)guanidine;
(1S,5S)-5-(2-chlorophenyl)-3-ethyl-2-oxa-4-azabicyclo[3.3.1]non-3-en-9-one;
3-((1S,5S)-5-(2-chlorophenyl)-9-oxo-2-oxa-4-azabicyclo[3.3.1]non-3-en-3-yl)-2-hydroxypropanoic acid;
2-(((1S,5S)-5-(2-chlorophenyl)-9-oxo-2-oxa-4-azabicyclo[3.3.1]non-3-en-3-yl)methyl)-2-hydroxysuccinic acid;
5-((1S,5S)-5-(2-chlorophenyl)-9-oxo-2-oxa-4-azabicyclo[3.3.1]non-3-en-3-yl)pentanoic acid;
3-((1S,5S)-5-(2-chlorophenyl)-9-oxo-2-oxa-4-azabicyclo[3.3.1]non-3-en-3-yl)-2,3-dihydroxypropanoic acid;
3-((1S,5S)-5-(2-chlorophenyl)-9-oxo-2-oxa-4-azabicyclo[3.3.1]non-3-en-3-yl)propanoic acid;
(1S,5S)-5-(2-chlorophenyl)-3-heptyl-2-oxa-4-azabicyclo[3.3.1]non-3-en-9-one;
(1S,5S)-3-(1-amino-2-hydroselenoethyl)-5-(2-chlorophenyl)-2-oxa-4-azabicyclo[3.3.1]non-3-en-9-one;
(1S,5S)-5-(2-chlorophenyl)-3-(2-(methylamino)ethyl)-2-oxa-4-azabicyclo[3.3.1]non-3-en-9-one;
(1S,5S)-5-(2-chlorophenyl)-3-(1,2-diaminoethyl)-2-oxa-4-azabicyclo[3.3.1]non-3-en-9-one;
(1S,5S)-3-(2-amino-1-hydroxyethyl)-5-(2-chlorophenyl)-2-oxa-4-azabicyclo[3.3.1]non-3-en-9-one;
(1S,5S)-3-(3-aminopropyl)-5-(2-chlorophenyl)-2-oxa-4-azabicyclo[3.3.1]non-3-en-9-one;
(1S,5S)-3-(4-aminobutyl)-5-(2-chlorophenyl)-2-oxa-4-azabicyclo[3.3.1]non-3-en-9-one;
(1S,5S)-3-(3-aminopentyl)-5-(2-chlorophenyl)-2-oxa-4-azabicyclo[3.3.1]non-3-en-9-one;
(1S,5S)-3-(1-amino-3-hydroxypropyl)-5-(2-chlorophenyl)-2-oxa-4-azabicyclo[3.3.1]non-3-en-9-one;
(1S,5S)-5-(2-chlorophenyl)-3-(1,4-diaminobutyl)-2-oxa-4-azabicyclo[3.3.1]non-3-en-9-one;
4-amino-4-((1S,5S)-5-(2-chlorophenyl)-9-oxo-2-oxa-4-azabicyclo[3.3.1]non-3-en-3-yl)-N-ethylbutanamide;
(1S,5S)-5-(2-chlorophenyl)-3-(1,5-diamino-4-hydroxypentyl)-2-oxa-4-azabicyclo[3.3.1]non-3-en-9-one;
1-(4-amino-4-((1S,5S)-5-(2-chlorophenyl)-9-oxo-2-oxa-4-azabicyclo[3.3.1]non-3-en-3-yl)butyl)urea;
1-(5-amino-5-((1S,5S)-5-(2-chlorophenyl)-9-oxo-2-oxa-4-azabicyclo[3.3.1]non-3-en-3-yl)pentyl)urea;
1-(5-amino-5-((1S,5S)-5-(2-chlorophenyl)-9-oxo-2-oxa-4-azabicyclo[3.3.1]non-3-en-3-yl)pentyl)guanidine;
1-(2-((1S,5S)-5-(2-chlorophenyl)-9-oxo-2-oxa-4-azabicyclo[3.3.1]non-3-en-3-yl)ethyl)guanidine;
(1S,5S)-3-(1-amino-2-methylbutyl)-5-(2-chlorophenyl)-2-oxa-4-azabicyclo[3.3.1]non-3-en-9-one;
(1S,5S)-3-(1-amino-2-(5-hydroxy-1H-indol-3-yl)ethyl)-5-(2-chlorophenyl)-2-oxa-4-azabicyclo[3.3.1]non-3-en-9-one;
(1S,5S)-3-(1-amino-2-(5-methyl-1H-indol-3-yl)ethyl)-5-(2-chlorophenyl)-2-oxa-4-azabicyclo[3.3.1]non-3-en-9-one;
(1S,5S)-3-(2-(1H-indol-3-yl)-1-(methylamino)ethyl)-5-(2-chlorophenyl)-2-oxa-4-azabicyclo[3.3.1]non-3-en-9-one;
(1S,5S)-5-(2-chlorophenyl)-3-(4-hydroxypyrrolidin-2-yl)-2-oxa-4-azabicyclo[3.3.1]non-3-en-9-one;
(1S,5S)-3-(1-amino-2-hydroxy-3-methylbutyl)-5-(2-chlorophenyl)-2-oxa-4-azabicyclo[3.3.1]non-3-en-9-one;
(1S,5S)-3-(1-(methylamino)ethyl)-5-(2-chlorophenyl)-2-oxa-4-azabicyclo[3.3.1]non-3-en-9-one;
(1S,5S)-3-(2-aminopropyl)-5-(2-chlorophenyl)-2-oxa-4-azabicyclo[3.3.1]non-3-en-9-one;
N-(5-amino-5-((1S,5S)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;

(1S,5S)-3-(1-amino-3-hydroxy-2-methylbutyl)-5-(2-chlorophenyl)-2-oxa-4-azabicyclo[3.3.1]non-3-en-9-one;

(1S,5S)-3-(1-amino-2,2-dimethylpropyl)-5-(2-chlorophenyl)-2-oxa-4-azabicyclo[3.3.1]non-3-en-9-one;

(1S,5S)-3-(amino(3-amino-4-hydroxyphenyl)methyl)-5-(2-chlorophenyl)-2-oxa-4-azabicyclo[3.3.1]non-3-en-9-one;

(1S,5S)-3-(1-amino-2-hydroxy-2-phenylethyl)-5-(2-chlorophenyl)-2-oxa-4-azabicyclo[3.3.1]non-3-en-9-one; and (1S,5S)-3-(1-amino-2-(4-methoxyphenyl)ethyl)-5-(2-chlorophenyl)-2-oxa-4-azabicyclo[3.3.1]non-3-en-9-one;

or pharmaceutically acceptable salts thereof.

5. The compound of claim 4, selected from the group consisting of:

(1R,5R)-5-(2-chlorophenyl)-2-oxa-4-azabicyclo[3.3.1]non-3-en-9-one;

(1R,5R)-5-(2-chlorophenyl)-3-methyl-2-oxa-4-azabicyclo[3.3.1]non-3-en-9-one;

(1R,5R)-5-(2-chlorophenyl)-3-(1-hydroxyethyl)-2-oxa-4-azabicyclo[3.3.1]non-3-en-9-one;

(1R,5R)-3-((S)-1-amino-2-methylpropyl)-5-(2-chlorophenyl)-2-oxa-4-azabicyclo[3.3.1]non-3-en-9-one;

(1R,5R)-3-(aminomethyl)-5-(2-chlorophenyl)-2-oxa-4-azabicyclo[3.3.1]non-3-en-9-one;

(1R,5R)-5-(2-chlorophenyl)-3-fluorocarbonyl-2-oxa-4-azabicyclo[3.3.1]non-3-en-9-one;

(1R,5R)-5-(2-chlorophenyl)-3-((S)-1,5-diaminopentyl)-2-oxa-4-azabicyclo[3.3.1]non-3-en-9-one;

(1R,5R)-3-((S)-1-aminoethyl)-5-(2-chlorophenyl)-2-oxa-4-azabicyclo[3.3.1]non-3-en-9-one;

(1R,5R)-5-(2-chlorophenyl)-3-phenyl-2-oxa-4-azabicyclo[3.3.1]non-3-en-9-one;

(1R,5R)-3-((1S,2R)-1-amino-2-methylbutyl)-5-(2-chlorophenyl)-2-oxa-4-azabicyclo[3.3.1]non-3-en-9-one;

(1R,5R)-3-((S)-1-amino-3-methylbutyl)-5-(2-chlorophenyl)-2-oxa-4-azabicyclo[3.3.1]non-3-en-9-one;

(1R,5R)-3-((S)-1-amino-2-phenylethyl)-5-(2-chlorophenyl)-2-oxa-4-azabicyclo[3.3.1]non-3-en-9-one;

(1R,5R)-3-((S)-1-amino-2-(4-hydroxyphenyl)ethyl)-5-(2-chlorophenyl)-2-oxa-4-azabicyclo[3.3.1]non-3-en-9-one;

(1R,5R)-3-((S)-1-amino-2-(1H-indol-3-yl)ethyl)-5-(2-chlorophenyl)-2-oxa-4-azabicyclo[3.3.1]non-3-en-9-one;

(1R,5R)-3-((S)-1-amino-2-(1H-imidazol-4-yl)ethyl)-5-(2-chlorophenyl)-2-oxa-4-azabicyclo[3.3.1]non-3-en-9-one;

(1R,5R)-5-(2-chlorophenyl)-3-(pyrrolidin-2-yl)-2-oxa-4-azabicyclo[3.3.1]non-3-en-9-one;

(S)-3-amino-3-((1R,5R)-5-(2-chlorophenyl)-9-oxo-2-oxa-4-azabicyclo[3.3.1]non-3-en-3-yl)propanoic acid;

(S)-4-amino-4-((1R,5R)-5-(2-chlorophenyl)-9-oxo-2-oxa-4-azabicyclo[3.3.1]non-3-en-3-yl)butanoic acid;

(S)-4-amino-4-((1R,5R)-5-(2-chlorophenyl)-9-oxo-2-oxa-4-azabicyclo[3.3.1]non-3-en-3-yl)butanamide;

(S)-3-amino-3-((1R,5R)-5-(2-chlorophenyl)-9-oxo-2-oxa-4-azabicyclo[3.3.1]non-3-en-3-yl)propanamide;

(1R,5R)-3-((S)-1-amino-3-(methylthio)propyl)-5-(2-chlorophenyl)-2-oxa-4-azabicyclo[3.3.1]non-3-en-9-one;

(1R,5R)-3-((R)-1-amino-2-mercaptoethyl)-5-(2-chlorophenyl)-2-oxa-4-azabicyclo[3.3.1]non-3-en-9-one;

(1R,5R)-3-((S)-1-amino-2-hydroxyethyl)-5-(2-chlorophenyl)-2-oxa-4-azabicyclo[3.3.1]non-3-en-9-one; and (1R,5R)-3-((S)-1-amino-2-methoxyethyl)-5-(2-chlorophenyl)-2-oxa-4-azabicyclo[3.3.1]non-3-en-9-one;

or pharmaceutically acceptable salts thereof.

6. The compound of claim 4, selected from the group consisting of:

(1R,5R)-5-(2-chlorophenyl)-2-oxa-4-azabicyclo[3.3.1]non-3-en-9-one;

(1R,5R)-5-(2-chlorophenyl)-3-methyl-2-oxa-4-azabicyclo[3.3.1]non-3-en-9-one;

(1R,5R)-5-(2-chlorophenyl)-3-(1-hydroxyethyl)-2-oxa-4-azabicyclo[3.3.1]non-3-en-9-one;

(1R,5R)-3-((S)-1-amino-2-methylpropyl)-5-(2-chlorophenyl)-2-oxa-4-azabicyclo[3.3.1]non-3-en-9-one;

(1R,5R)-3-(aminomethyl)-5-(2-chlorophenyl)-2-oxa-4-azabicyclo[3.3.1]non-3-en-9-one;

(1R,5R)-5-(2-chlorophenyl)-3-fluorocarbonyl-2-oxa-4-azabicyclo[3.3.1]non-3-en-9-one;

(1R,5R)-5-(2-chlorophenyl)-3-((S)-1,5-diaminopentyl)-2-oxa-4-azabicyclo[3.3.1]non-3-en-9-one; and (1R,5R)-3-((S)-1-aminoethyl)-5-(2-chlorophenyl)-2-oxa-4-azabicyclo[3.3.1]non-3-en-9-one;

or pharmaceutically acceptable salts thereof.

7. The compound of claim 4, selected from the group consisting of:

(1R,5R)-3-(1-amino-2-hydroselenoethyl)-5-(2-chlorophenyl)-2-oxa-4-azabicyclo[3.3.1]non-3-en-9-one;

(1R,5R)-5-(2-chlorophenyl)-3-(2-(methylamino)ethyl)-2-oxa-4-azabicyclo[3.3.1]non-3-en-9-one;

(1R,5R)-5-(2-chlorophenyl)-3-(1,2-diaminoethyl)-2-oxa-4-azabicyclo[3.3.1]non-3-en-9-one;

(1R,5R)-3-(2-amino-1-hydroxyethyl)-5-(2-chlorophenyl)-2-oxa-4-azabicyclo[3.3.1]non-3-en-9-one;

(1R,5R)-3-(3-aminopropyl)-5-(2-chlorophenyl)-2-oxa-4-azabicyclo[3.3.1]non-3-en-9-one;

(1R,5R)-3-(4-aminobutyl)-5-(2-chlorophenyl)-2-oxa-4-azabicyclo[3.3.1]non-3-en-9-one;

(1R,5R)-3-(3-aminopentyl)-5-(2-chlorophenyl)-2-oxa-4-azabicyclo[3.3.1]non-3-en-9-one;

(1R,5R)-3-(1-amino-3-hydroxypropyl)-5-(2-chlorophenyl)-2-oxa-4-azabicyclo[3.3.1]non-3-en-9-one;

(1R,5R)-5-(2-chlorophenyl)-3-(1,4-diaminobutyl)-2-oxa-4-azabicyclo[3.3.1]non-3-en-9-one;

4-amino-4-((1R,5R)-5-(2-chlorophenyl)-9-oxo-2-oxa-4-azabicyclo[3.3.1]non-3-en-3-yl)-N-ethylbutanamide;

(1R,5R)-5-(2-chlorophenyl)-3-(1,5-diamino-4-hydroxypentyl)-2-oxa-4-azabicyclo[3.3.1]non-3-en-9-one;

1-(4-amino-4-((1R,5R)-5-(2-chlorophenyl)-9-oxo-2-oxa-4-azabicyclo[3.3.1]non-3-en-3-yl)butyl)urea;

1-(5-amino-5-((1R,5R)-5-(2-chlorophenyl)-9-oxo-2-oxa-4-azabicyclo[3.3.1]non-3-en-3-yl)pentyl)urea;

1-(5-amino-5-((1R,5R)-5-(2-chlorophenyl)-9-oxo-2-oxa-4-azabicyclo[3.3.1]non-3-en-3-yl)pentyl)guanidine;

1-(2-((1R,5R)-5-(2-chlorophenyl)-9-oxo-2-oxa-4-azabicyclo[3.3.1]non-3-en-3-yl)ethyl)guanidine;

(1R,5R)-3-(1-amino-2-methylbutyl)-5-(2-chlorophenyl)-2-oxa-4-azabicyclo[3.3.1]non-3-en-9-one;

(1R,5R)-3-(1-amino-2-(5-hydroxy-1H-indol-3-yl)ethyl)-5-(2-chlorophenyl)-2-oxa-4-azabicyclo[3.3.1]non-3-en-9-one;

(1R,5R)-3-(1-amino-2-(5-methyl-1H-indol-3-yl)ethyl)-5-(2-chlorophenyl)-2-oxa-4-azabicyclo[3.3.1]non-3-en-9-one;

(1R,5R)-3-(2-(1H-indol-3-yl)-1-(methylamino)ethyl)-5-(2-chlorophenyl)-2-oxa-4-azabicyclo[3.3.1]non-3-en-9-one;

(1R,5R)-5-(2-chlorophenyl)-3-(4-hydroxypyrrolidin-2-yl)-2-oxa-4-azabicyclo[3.3.1]non-3-en-9-one;

(1R,5R)-3-(1-amino-2-hydroxy-3-methylbutyl)-5-(2-chlorophenyl)-2-oxa-4-azabicyclo[3.3.1]non-3-en-9-one;
(1R,5R)-5-(2-chlorophenyl)-3-(1-(methylamino)ethyl)-2-oxa-4-azabicyclo[3.3.1]non-3-en-9-one;
(1R,5R)-3-(2-aminopropyl)-5-(2-chlorophenyl)-2-oxa-4-azabicyclo[3.3.1]non-3-en-9-one;
N-(5-amino-5-((1R,5R)-5-(2-chlorophenyl)-9-oxo-2-oxa-4-azabicyclo[3.3.1]non-3-en-3-yl)pentyl)-3-methyl-3,4-dihydro-2H-pyrrole-2-carboxamide;
(1R,5R)-3-(1-amino-3-hydroxy-2-methylbutyl)-5-(2-chlorophenyl)-2-oxa-4-azabicyclo[3.3.1]non-3-en-9-one;
(1R,5R)-3-(1-amino-2,2-dimethylpropyl)-5-(2-chlorophenyl)-2-oxa-4-azabicyclo[3.3.1]non-3-en-9-one;
(1R,5R)-3-(amino(3-amino-4-hydroxyphenyl)methyl)-5-(2-chlorophenyl)-2-oxa-4-azabicyclo[3.3.1]non-3-en-9-one;
(1R,5R)-3-(1-amino-2-hydroxy-2-phenylethyl)-5-(2-chlorophenyl)-2-oxa-4-azabicyclo[3.3.1]non-3-en-9-one; and
(1R,5R)-3-(1-amino-2-(4-methoxyphenyl)ethyl)-5-(2-chlorophenyl)-2-oxa-4-azabicyclo[3.3.1]non-3-en-9-one;
or pharmaceutically acceptable salts thereof.

8. The compound of claim 4, selected from the group consisting of:

(1R,5R)-5-(2-chlorophenyl)-3-ethyl-2-oxa-4-azabicyclo[3.3.1]non-3-en-9-one;
3-((1R,5R)-5-(2-chlorophenyl)-9-oxo-2-oxa-4-azabicyclo[3.3.1]non-3-en-3-yl)-2-hydroxypropanoic acid;
2-(((1R,5R)-5-(2-chlorophenyl)-9-oxo-2-oxa-4-azabicyclo[3.3.1]non-3-en-3-yl)methyl)-2-hydroxysuccinic acid;
5-((1R,5R)-5-(2-chlorophenyl)-9-oxo-2-oxa-4-azabicyclo[3.3.1]non-3-en-3-yl)pentanoic acid;
3-((1R,5R)-5-(2-chlorophenyl)-9-oxo-2-oxa-4-azabicyclo[3.3.1]non-3-en-3-yl)-2,3-dihydroxypropanoic acid;
3-((1R,5R)-5-(2-chlorophenyl)-9-oxo-2-oxa-4-azabicyclo[3.3.1]non-3-en-3-yl)propanoic acid; and
(1R,5R)-5-(2-chlorophenyl)-3-heptyl-2-oxa-4-azabicyclo[3.3.1]non-3-en-9-one;
or pharmaceutically acceptable salts thereof.

9. A pharmaceutical composition comprising: a therapeutically effective amount of a compound of claim 1, or pharmaceutically acceptable salt thereof and a pharmaceutically acceptable excipient.

10. A pharmaceutical composition comprising: a therapeutically effective amount of a compound of claim 4, or pharmaceutically acceptable salt thereof and a pharmaceutically acceptable excipient.

* * * * *